(12) United States Patent
Hwang et al.

(10) Patent No.: US 9,368,730 B2
(45) Date of Patent: Jun. 14, 2016

(54) HETEROCYCLIC COMPOUND AND ORGANIC LIGHT-EMITTING DEVICE COMPRISING THE SAME

(71) Applicant: SAMSUNG DISPLAY CO., LTD., Yongin, Gyeonggi-Do (KR)

(72) Inventors: Seok-Hwan Hwang, Yongin (KR); Young-Kook Kim, Yongin (KR); Hye-Jin Jung, Yongin (KR); Jun-Ha Park, Yongin (KR); Eun-Young Lee, Yongin (KR); Jin-O Lim, Yongin (KR); Sang-Hyun Han, Yongin (KR); Eun-Jae Jeong, Yongin (KR); Soo-Yon Kim, Yongin (KR); Jong-Hyuk Lee, Yongin (KR)

(73) Assignee: Samsung Display Co., Ltd., Yongin-si (KR)

( * ) Notice: Subject to any disclaimer, the term of this patent is extended or adjusted under 35 U.S.C. 154(b) by 342 days.

(21) Appl. No.: 14/038,290

(22) Filed: Sep. 26, 2013

(65) Prior Publication Data
US 2014/0361254 A1  Dec. 11, 2014

(30) Foreign Application Priority Data
Jun. 5, 2013 (KR) .................. 10-2013-0064961

(51) Int. Cl.
| H01L 51/00 | (2006.01) |
| H01L 27/32 | (2006.01) |
| C07D 403/14 | (2006.01) |
| C07F 5/02 | (2006.01) |
| H01L 51/50 | (2006.01) |

(52) U.S. Cl.
CPC .......... *H01L 51/0067* (2013.01); *C07D 403/14* (2013.01); *C07F 5/025* (2013.01); *H01L 51/0072* (2013.01); *H01L 51/0081* (2013.01); *H01L 51/0085* (2013.01); *H01L 51/0088* (2013.01); *H01L 51/5016* (2013.01)

(58) Field of Classification Search
None
See application file for complete search history.

(56) References Cited

U.S. PATENT DOCUMENTS 7,429,372 B2  9/2008  Pez et al.

FOREIGN PATENT DOCUMENTS

WO  WO 2012/023947 A1  2/2012

OTHER PUBLICATIONS

Baldo, M.A. et al., "Highly Efficient Phosphorescent Emission From Organic Electroluminescent Devices", Nature, Sep. 10, 1998, pp. 151-154, vol. 395, Macmillan Publishers Ltd.
Baldo, M.A. et al., "Very High-Efficiency Green Organic Light-Emitting Devices Based on Electrophosphorescence", Applied Physics Letters, Jul. 5, 1999, pp. 4-6, vol. 75, No. 1, American Institute of Physics.
Kwong, Raymond C. et al., "High Operational Stability of Electrophosphorescent Devices", Applied Physics Letters, Jul. 1, 2002, pp. 162-164, vol. 81, No. 1, American Institute of Physics.
Adachi, Chihaya et al., "High-Efficiency Organic Electrophosphorescent Devices With tris(2-phenylpyridine)iridium Doped Into Electron-Transporting Materials", Applied Physics Letters, Aug. 7, 2000, pp. 904-906, vol. 77, No. 6, American Institute of Physics.
Internet Article http://www.sigmaaldrich.com/catalog/product/aldrich/ph007423?lang=en&region=US, "4H-benzo[def]carbazole", viewed on Sep. 25, 2013, 1 page.
2009 Fall Assembly and Symposium, Gwangju Institute of Science and Technology, Oryong Hall, vol. 34, No. 2, Oct. 8-9, 2009, "A Novel Conjugated Polymer Based on 4H-benzo[def]carbazole backbone for OLED", 1 page.

*Primary Examiner* — J. L. Yang
(74) *Attorney, Agent, or Firm* — Lewis Roca Rothgerber Christie LLP

(57) ABSTRACT

A heterocyclic compound represented by Formula 1 below and an organic light-emitting device including the heterocyclic compound are provided:

Formula 1

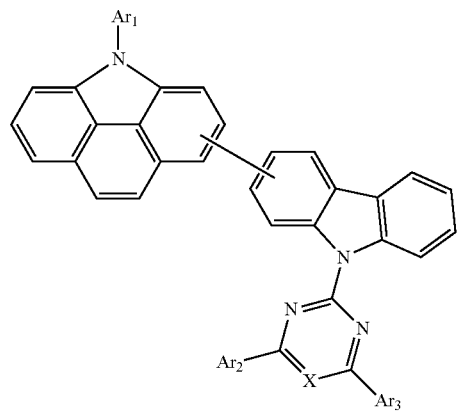

$Ar_1$, $Ar_2$, $Ar_3$ and X in Formula 1 are defined as in the specification.

20 Claims, 1 Drawing Sheet

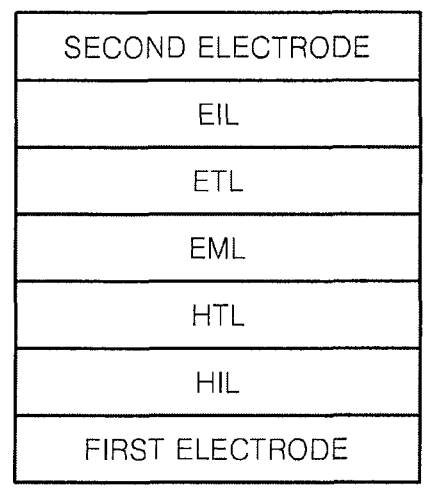

HETEROCYCLIC COMPOUND AND ORGANIC LIGHT-EMITTING DEVICE COMPRISING THE SAME

CROSS-REFERENCE TO RELATED APPLICATION

This application claims priority to and the benefit of Korean Patent Application No. 10-2013-0064961, filed on Jun. 5, 2013, in the Korean Intellectual Property Office, the disclosure of which is incorporated herein by reference.

BACKGROUND

1. Field

One or more embodiments of the present invention relate to a heterocyclic compound and an organic light-emitting device including the heterocyclic compound.

2. Description of the Related Art

Organic light-emitting devices (OLEDs), which are self-emitting devices, have advantages such as wide viewing angles, excellent contrast (e.g. high contrast), quick response, high brightness, excellent driving voltage characteristics (e.g. low driving voltage characteristics), and can provide multi-colored images.

A typical OLED has a structure including a substrate, and an anode, a hole transport layer (HTL), an emission layer (EML), an electron transport layer (ETL), and a cathode which are sequentially stacked on the substrate. In this regard, the HTL, the EML, and the ETL are organic thin films formed of organic compounds.

An operating principle of an OLED having the above-described structure is as follows.

When a voltage is applied between the anode and the cathode, holes injected from the anode move to the EML via the HTL, and electrons injected from the cathode move to the EML via the ETL. The holes and electrons recombine in the EML to generate excitons. When the excitons drop from an excited state to a ground state, light is emitted.

There is an ongoing demand for a material having improved electrical stability, high charge-transfer or emission capability, and a high glass transition temperature that is high enough to prevent crystallization, in regards to existing uni-molecular materials.

SUMMARY

One or more aspects of embodiments of the present invention are directed towards a novel compound that has improved electrical characteristics, improved charge transporting capability, improved emission capability, and glass transition temperatures (Tg) high enough to prevent crystallization, and thus is suitable, for example, as a light emitting material or an electron transporting material for fluorescent or phosphorescent devices of any color of red, green, blue, or white.

Additional aspects will be set forth in part in the description which follows and, in part, will be apparent from the description, or may be learned by practice of the presented embodiments.

According to one or more embodiments of the present invention, there is provided a heterocyclic compound represented by Formula 1 below:

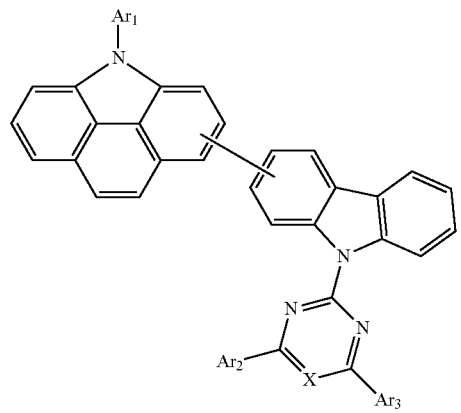

Formula 1 wherein, in Formula 1, $Ar_1$ to $Ar_3$ are each independently selected from a hydrogen atom, a deuterium atom, a substituted or unsubstituted C1-C60 alkyl group, a substituted or unsubstituted C3-C60 cycloalkyl group, a substituted or unsubstituted C1-C60 heteroaryl group, a substituted or unsubstituted C6-C60 aryl group, and a substituted or unsubstituted C6-C60 condensed polycyclic group; and X is N or CH.

According to one or more embodiments of the present invention, an organic light-emitting device includes: a first electrode; a second electrode; and an organic layer between the first electrode and the second electrode, the organic layer including the heterocyclic compound of Formula 1 above. In some embodiments, the organic layer is an organic film.

According to one or more embodiments of the present invention, a flat panel display device includes the above-described organic light-emitting device, the first electrode of the organic light-emitting device being electrically connected to a source electrode or a drain electrode of a thin-film transistor.

BRIEF DESCRIPTION OF THE DRAWING

These and/or other aspects will become apparent and more readily appreciated from the following description of the embodiments, taken in conjunction with the accompanying drawing of which:

The drawing is a schematic view of a structure of an organic light-emitting device according to an embodiment of the present invention.

DETAILED DESCRIPTION

Reference will now be made in detail to embodiments, examples of which are illustrated in the accompanying drawings, wherein like reference numerals refer to the like elements throughout. In this regard, the present embodiments may have different forms and should not be construed as being limited to the descriptions set forth herein. Accordingly, the embodiments are merely described below, by referring to the figures, to explain aspects of the present description. As used herein, the term "and/or" includes any and all combinations of one or more of the associated listed items. Expressions such as "at least one of," when preceding a list of elements, modify the entire list of elements and do not modify the individual elements of the list.

Further, the use of "may" when describing embodiments of the present invention refers to "one or more embodiments of the present invention."

Also, in the context of the present application, when a first element is referred to as being "on" a second element, it can be directly on the second element or be indirectly on the second element with one or more intervening elements interposed therebetween.

According to an aspect of the present invention, a heterocyclic compound represented by Formula 1 below is provided.

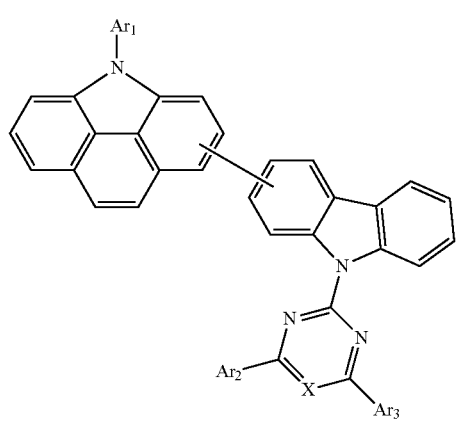

Formula 1

In Formula 1, $Ar_1$ to $Ar_3$ are each independently selected from a hydrogen atom, a deuterium atom, a substituted or unsubstituted C1-C60 alkyl group, a substituted or unsubstituted C3-C60 cycloalkyl group, a substituted or unsubstituted C1-C60 heteroaryl group, a substituted or unsubstituted C6-C60 aryl group, and a substituted or unsubstituted C6-C60 condensed polycyclic group; and X is N or CH.

In an organic light-emitting device using tris(2-phenylpyridine)iridium ($Ir(ppy)_3$) known as a typical phosphorescent material, its spectra appear to have the CIE coordinates of (0.30, 0.63). This organic light-emitting device has a power efficiency of 6% as quantum efficiency, but, despite functioning as an "electro-phosphorescent" device, does not satisfy high-quality display requirements of low efficiency, lifetime, and stability. Accordingly, there is a need for the development of phosphorescent materials with high efficiency at low voltage and long lifetime characteristics, and organic light-emitting devices using such phosphorescent materials.

The heterocyclic compound of Formula 1 above may be used as a light-emitting material or an electron transporting material in organic light-emitting devices. The heterocyclic compound of Formula 1 has a high glass transition temperature (Tg) or melting point due to an introduction of the heterocyclic group. Thus, the heterocyclic compound has high heat resistance against Joule heating generated in an organic layer, between organic layers, or between an organic layer and a metal electrode when light emission occurs, and has high durability in high-temperature environments. An organic light-emitting device manufactured using the heterocyclic compound of Formula 1 may have high durability when stored or operated.

The heterocyclic compound of Formula 1 may be a compound represented by Formula 2 or Formula 3 below:

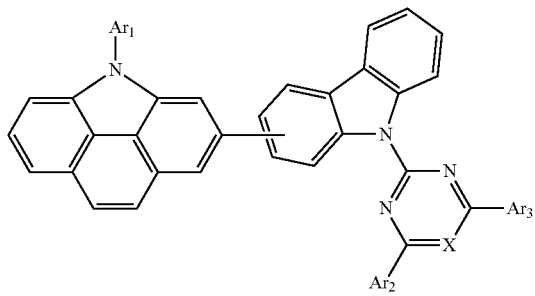

Formula 2

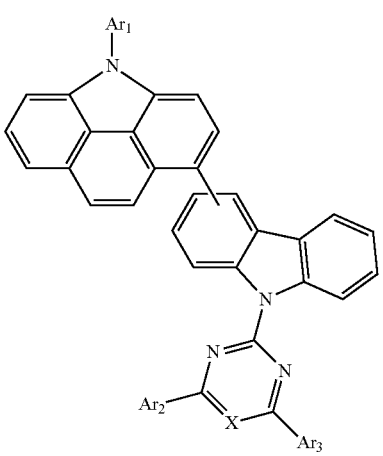

Formula 3

In Formula 2 and Formula 3, $Ar_1$ to $Ar_3$, and X are the same as defined in Formula 1 above.

Substituents in the heterocyclic compound of Formula 1 will now be described in detail.

In some embodiments, $Ar_1$ is selected from the group of compounds represented by Formulae 2a to 2c below.

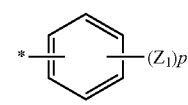

2a

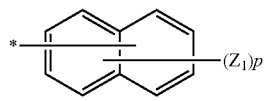

2b

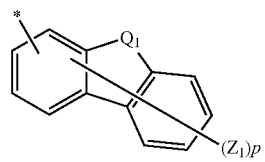

2c

In Formulae 2a to 2c above, $Q_1$ is O or S;

$Z_1$ is selected from a hydrogen atom, a deuterium atom, a substituted or unsubstituted C1-C20 alkyl group, a C1-C20 alkylsilyl group, a C1-C20 arylsilyl group, a substituted or unsubstituted C6-C20 aryl group, a substituted or unsubstituted C2-C20 heteroaryl group, or a substituted or unsubstituted C6-C20 condensed polycyclic group, an amino group substituted with at least one of a C6-C20 aryl group or a C2-C20 heteroaryl group, a halogen group, a cyano group, a nitro group, a hydroxy group, and a carboxy group, wherein a plurality of $Z_1$s may be the same or different;

p is an integer from 1 to 7; and * indicates a binding site.

In some embodiments, $Ar_2$ and $Ar_3$ are each independently selected from the group of compounds represented by Formulae 3a to 3c:

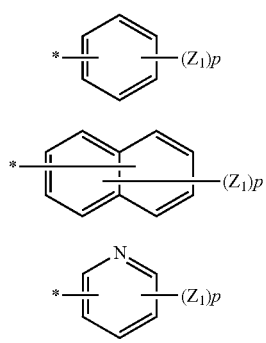

In Formulae 3a to 3c above, $Z_1$ is selected from a hydrogen atom, a deuterium atom, a substituted or unsubstituted C1-C20 alkyl group, C1-C20 alkylsilyl group, C1-C20 arylsilyl group, a substituted or unsubstituted C6-C20 aryl group, a substituted or unsubstituted C2-C20 heteroaryl group, or a substituted or unsubstituted C6-C20 condensed polycyclic group, an amino group substituted with at least one of a C6-C20 aryl group or a C2-C20 heteroaryl group, a halogen group, a cyano group, a nitro group, a hydroxy group, and a carboxy group, wherein a plurality of $Z_1$s may be the same or different;

p is an integer from 1 to 7; and * indicates a binding site.

Hereinafter, substituents described with reference to the formulae will now be described in detail. In this regard, the numbers of carbons in substituents are presented only for illustrative purposes and do not limit the characteristics of the substituents. The substituents not defined herein are construed as having the same meanings as understood by one of ordinary skill in the art.

The unsubstituted C1-C60 alkyl group used herein may be linear or branched. Examples of the alkyl group may include, but are not limited to, a methyl group, an ethyl group, a propyl group, an isobutyl group, a sec-butyl group, a pentyl group, an iso-amyl group, a hexyl group, a heptyl group, an octyl group, a nonanyl group, and a dodecyl group. The substituted C1-C60 alkyl group may refer to the unsubstituted C1-C60 alkyl group in which at least one hydrogen atom is substituted with any one selected from a deuterium atom, a halogen atom, a hydroxyl group, a nitro group, a cyano group, an amino group, an amidino group, hydrazine, hydrazone, a carboxyl group or a salt thereof, a sulfonic acid group or a salt thereof, a phosphoric acid group or a salt thereof, a C1-C10 alkyl group, a C1-C10 alkoxy group, a C2-C10 alkenyl group, a C2-C10 alkynyl group, a C6-C16 aryl group, or a C2-C16 heteroaryl group.

The unsubstituted C2-C60 alkenyl group may refer to an unsaturated alkyl groups having at least one carbon-carbon double bond at one or more positions along a carbon chain of the unsubstituted C2-C60 alkyl group. For example, the unsubstituted C2-C60 alkenyl group may include a terminal alkene and/or an internal alkene. Non-limiting examples of the alkenyl group are an ethenyl group, a propenyl group, a butenyl group, and the like. The substituted C2-C60 alkenyl group may refer to the unsubstituted C2-C60 alkenyl group in which at least one hydrogen atom is substituted with any one of the substituents described above in conjunction with the C1-C60 alkyl group.

The unsubstituted C2-C60 alkynyl group may refer to an alkyl group having at least one carbon-carbon triple bond at one or more positions along a carbon chain of the unsubstituted C2-C60 alkyl group. For example, the unsubstituted C2-C60 alkynyl group may include a terminal alkyne and/or an internal alkyne. Non-limiting examples of the unsubstituted C2-C20 alkynyl group are acetylene, propylene, phenylacetylene, naphthylacetylene, isopropylacetylene, t-butylacetylene, and diphenylacetylene. The substituted C2-C60 alkynyl group may refer to the unsubstituted C2-C60 alkynyl group in which at least one hydrogen atom is substituted with any one of the substituents described above in conjunction with the C1-C60 alkyl group.

The unsubstituted C3-C60 cycloalkyl group may refer to a C3-C60 cyclic alkyl group. The substituted C3-C60 cycloalkyl group may refer to the unsubstituted C3-C60 cycloalkyl group in which at least one hydrogen atom is substituted with any one of the substituents described above in conjunction with the C1-C60 alkyl group.

The unsubstituted C1-C60 alkoxy group may refer to a group having a structure of —OA wherein A is the unsubstituted C1-C60 alkyl group as described above. Non-limiting examples of the unsubstituted C1-C60 alkoxy group are a methoxy group, an ethoxy group, a propoxy group, an isopropyloxy group, a butoxy group, and a pentoxy group. The substituted C1-C60 alkoxy group may refer to the unsubstituted C1-C60 alkoxy group in which at least one hydrogen atom is substituted with any one of the substituents such as those described above in conjunction with the C1-C60 alkyl group.

The unsubstituted C6-C60 aryl group may refer to a carbocyclic aromatic system containing at least one ring. At least two rings may be fused to each other or linked to each other by a single bond. The term 'aryl' refers to an aromatic system, such as phenyl, naphthyl, or anthracenyl. The substituted C6-C60 aryl group may refer to the unsubstituted C6-C60 aryl group in which at least one hydrogen atom is substituted with any one of the substituents described above in conjunction with the C1-C60 alkyl group.

Non-limiting examples of the substituted or unsubstituted C6-C60 aryl group are a phenyl group, a C1-C10 alkylphenyl group (for example, an ethylphenyl group), a biphenyl group, a C1-C10 alkyl biphenyl group, a C1-C10 alkoxybiphenyl group, a o-, m-, or p-toryl group, an o-, m-, or p-cumenyl group, a mesityl group, a phenoxyphenyl group, a (α,α-dimethylbenzene)phenyl group, a (N,N'-dimethyl)aminophenyl group, a (N,N'-diphenyl)aminophenyl group, a pentalenyl group, an indenyl group, a naphthyl group, a C1-C10 alkylnaphthyl group (for example, a methylnaphthyl group), a C1-C10 alkoxynaphthyl group (for example, a methoxynaphthyl group), an anthracenyl group, an azulenyl group, a heptalenyl group, an acenaphthylenyl group, a phenalenyl group, a fluorenyl group, an anthraquinolyl group, a methylanthryl group, a phenanthryl group, a triphenylene group, a pyrenyl group, a chrycenyl group, an ethyl-chrysenyl group, a picenyl group, a perylenyl group, a pentaphenyl group, a pentacenyl group, a tetraphenylenyl group, a hexaphenyl group, a hexacenyl group, a rubicenyl group, a coroneryl group, a trinaphthylenyl group, a heptaphenyl group, a heptacenyl group, a pyranthrenyl group, and an ovalenyl group.

The unsubstituted C1-C60 heteroaryl group used herein may refer to a carbocyclic aromatic system containing at least one ring including one or more heteroatoms selected from N, O, P and S as the ring atoms, with carbon atoms as the remaining ring atoms. At least two rings may be fused to each other or linked to each other by a single bond. Non-limiting examples of the unsubstituted C1-C60 heteroaryl group are a pyrazolyl group, an imidazolyl group, an oxazolyl group, a thiazolyl group, a triazolyl group, a tetrazolyl group, an oxadiazolyl group, a pyridinyl group, a pyridazinyl group, a pyrimidinyl group, a triazinyl group, a carbazol group, an indol group, a quinolyl group, an isoquinolyl group, and a dibenzothiophene group. The substituted C1-C60 heteroaryl group may refer to the unsubstituted C1-C60 heteroaryl group in which at least one hydrogen atom is substituted with any one of the substituents described above in conjunction with the C1-C60 alkyl group.

The unsubstituted C5-C60 aryloxy group may refer to a group represented by —$OA_1$, wherein $A_1$ may be a C6-C60 aryl group. A non-limiting example of the unsubstituted C5-C60 aryloxy group is a phenoxy group. The substituted C5-C60 aryloxy group may refer to the unsubstituted C5-C60 aryloxy group in which at least one hydrogen atom is substituted with any one of the substituents described above in conjunction with the C1-C60 alkyl group.

The unsubstituted C5-C60 arylthio group may refer to a group represented by —$SA_1$, wherein $A_1$ may be a C6-C60 aryl group. Non-limiting examples of the unsubstituted C5-C60 arylthio group are a benzenethio group and a naphthylthio group. The substituted C5-C60 arylthio group may refer to the unsubstituted C5-C60 arylthio group in which at least one hydrogen atom is substituted with any one of the substituents described above in conjunction with the C1-C60 alkyl group.

The unsubstituted C6-C60 condensed polycyclic group used herein may refer to either: i) a substituent including at least two rings wherein at least one aromatic ring and/or at least one non-aromatic ring are fused to each other, or ii) a substituent having an unsaturated group in a ring but unable to form a conjugated structure. The unsubstituted C6-C60 condensed polycyclic group is distinct from an aryl group or a heteroaryl group as it has a non-aromatic component.

Non-limiting examples of the compound represented by Formula 1 are Compounds 1 to 80 represented below:

1

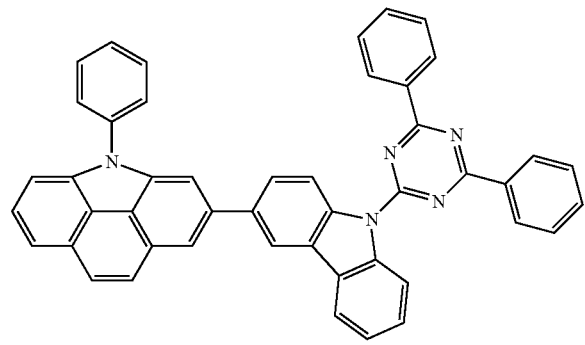

2

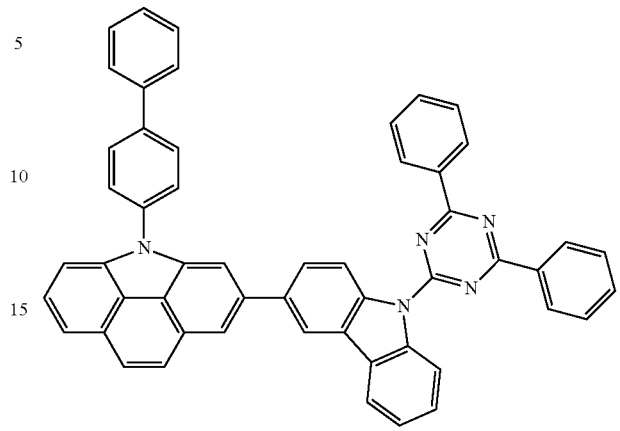

3

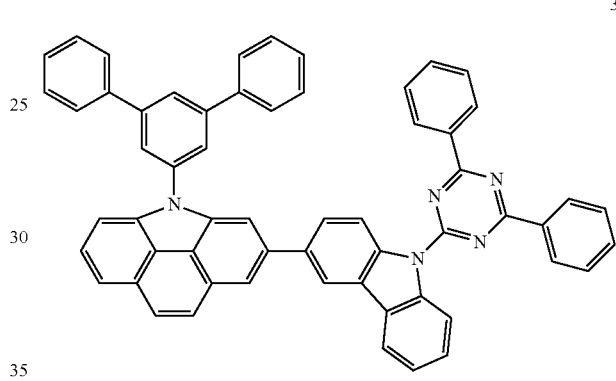

4

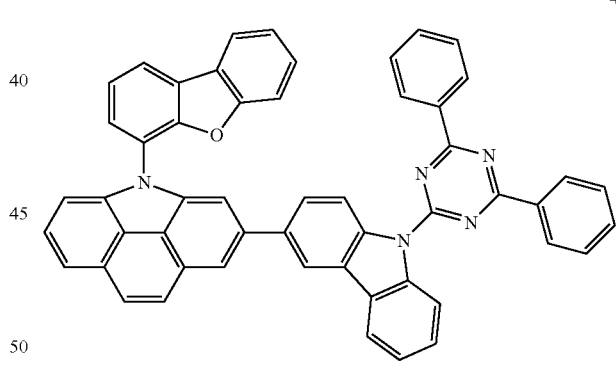

5

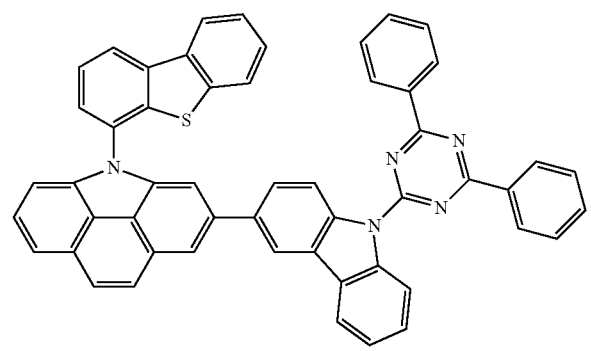

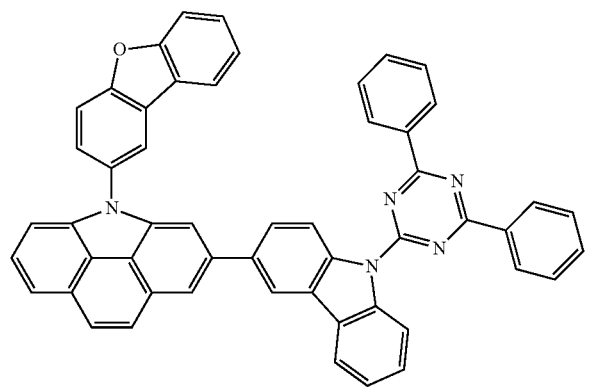
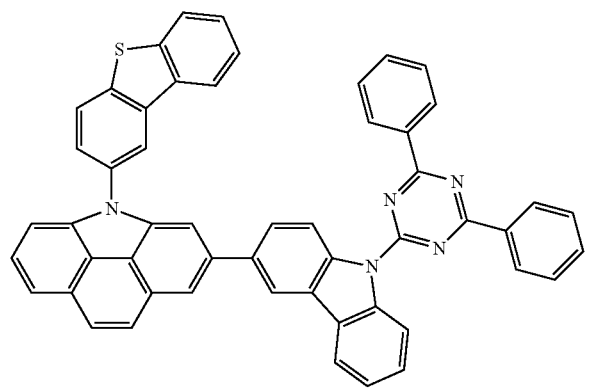
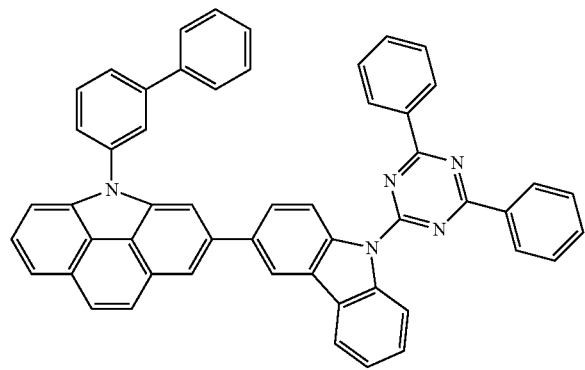
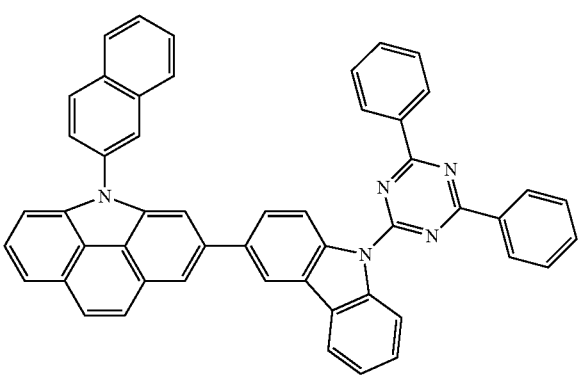
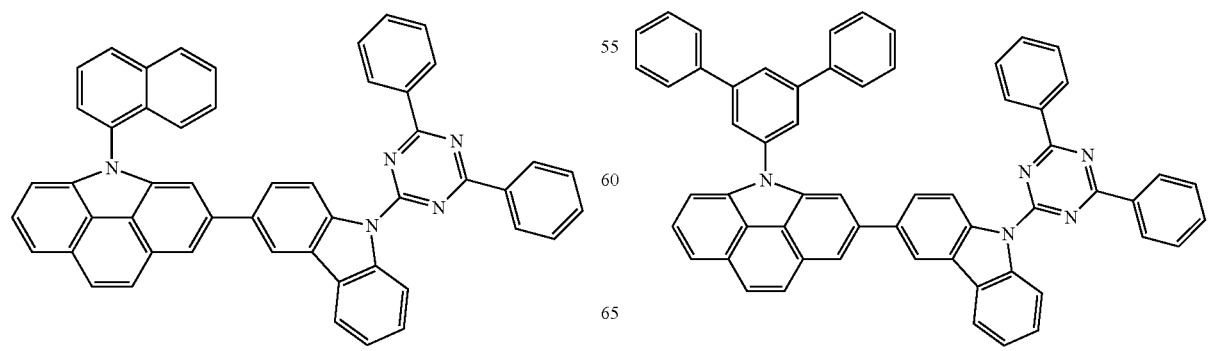

14
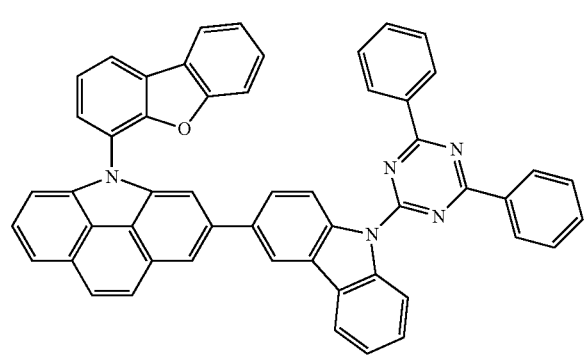
15
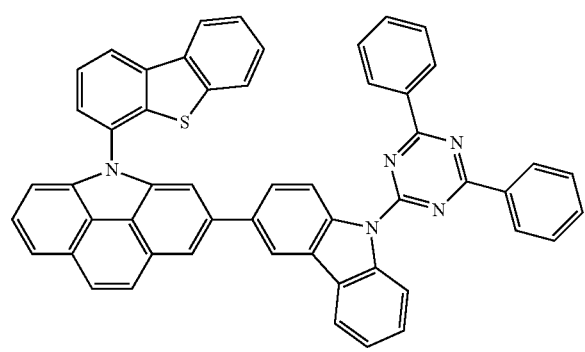
16
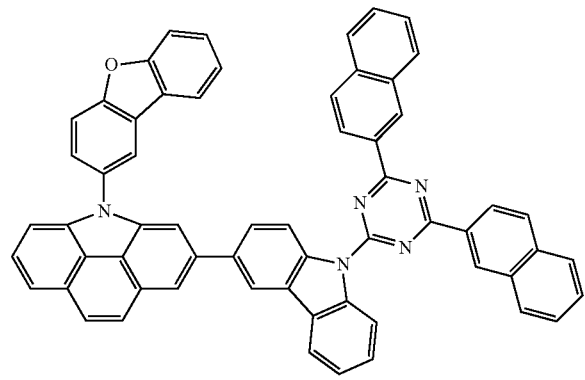
17
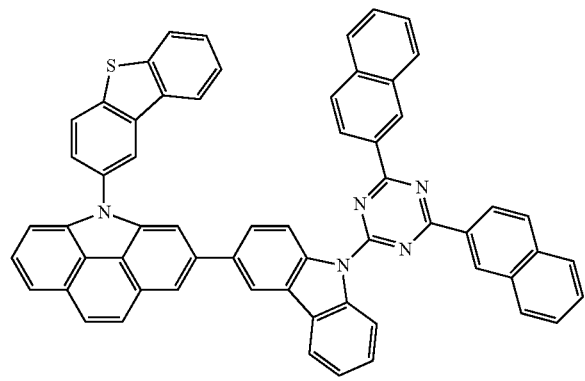
18
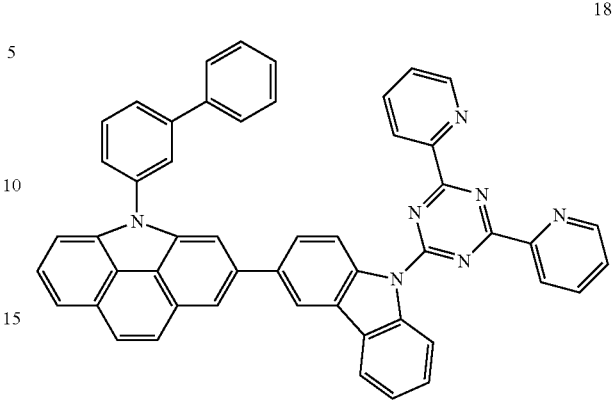
19
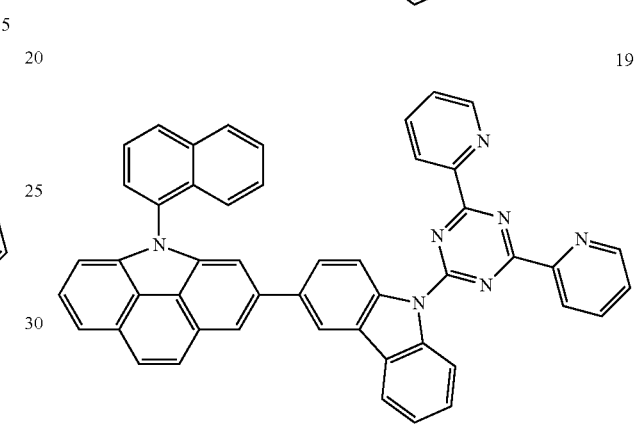
20
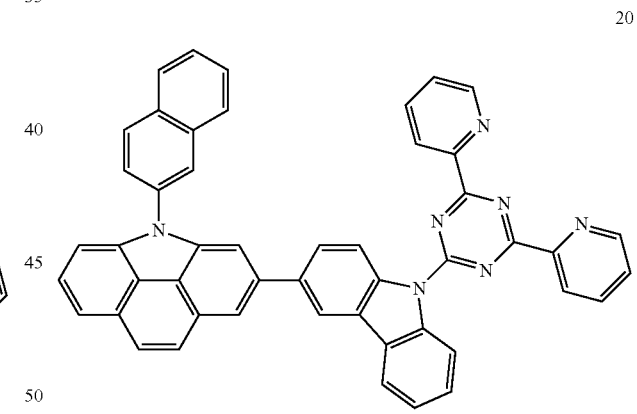
21
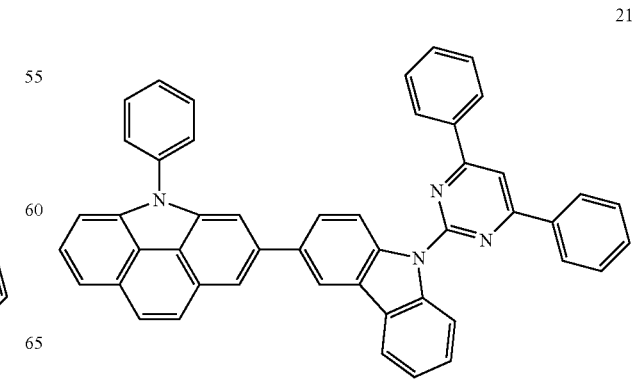

22
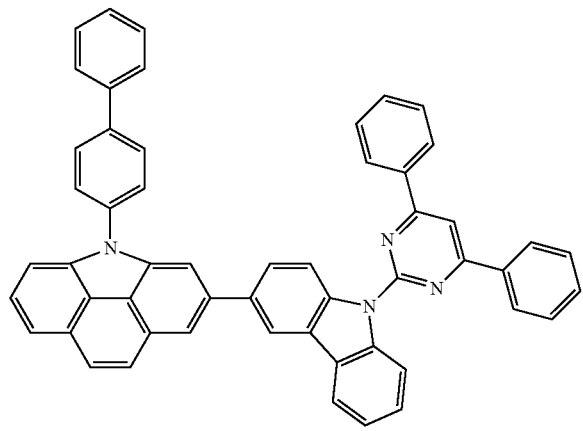
23
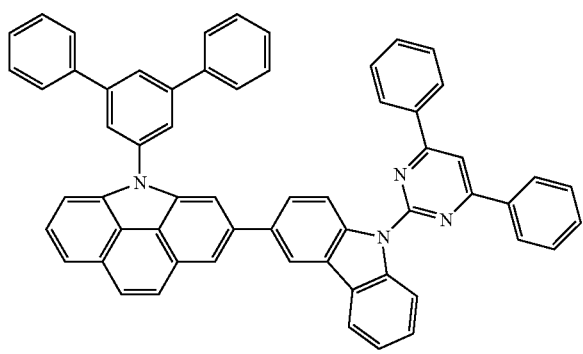
24
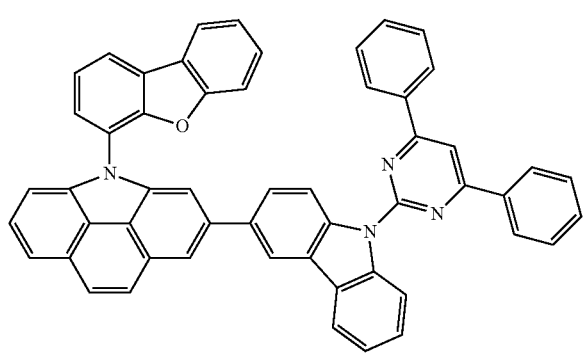
25
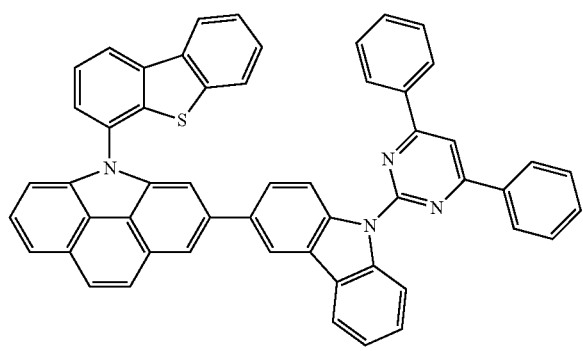
26
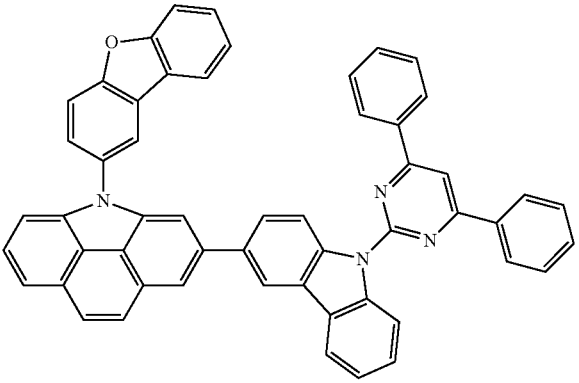
27
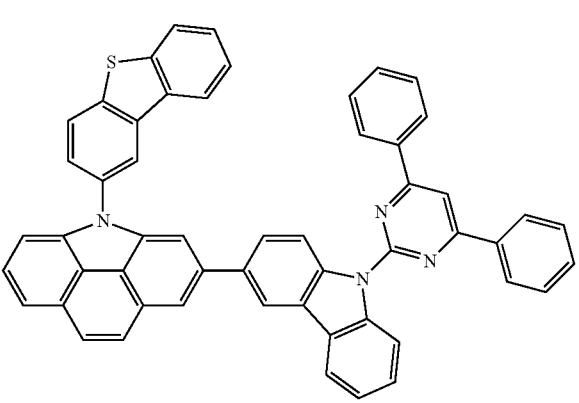
28
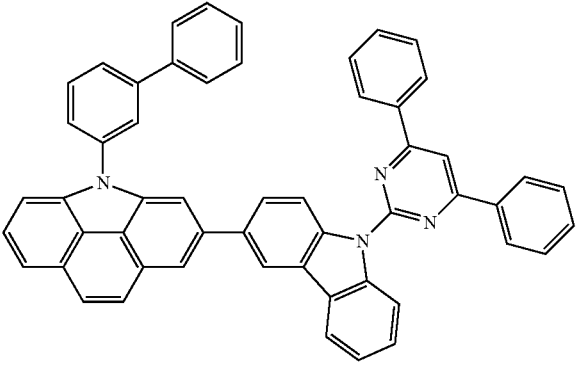
29
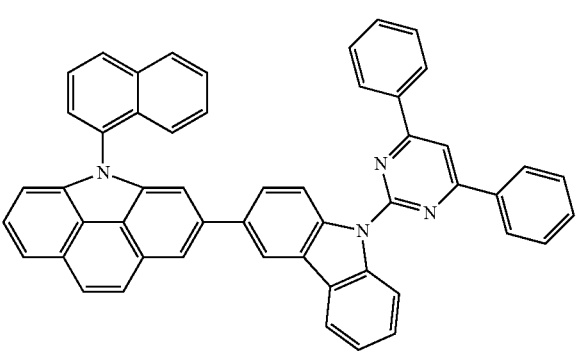

15
-continued
30
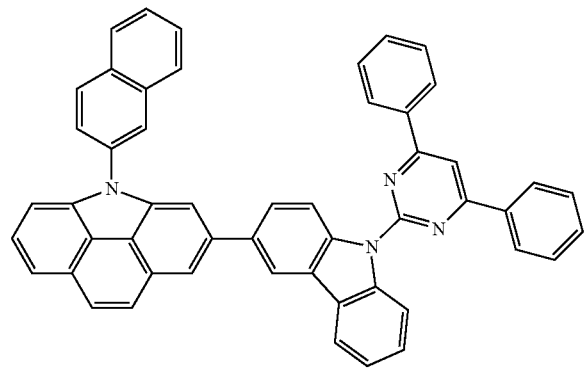
31
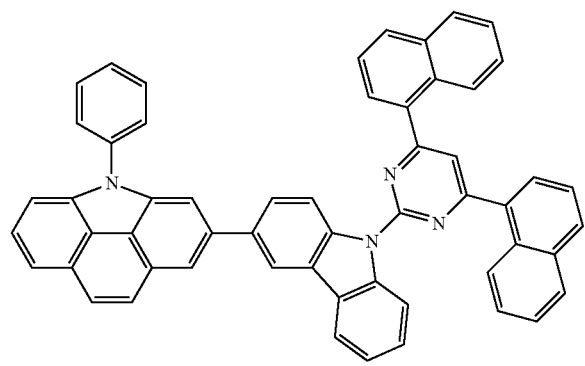
32
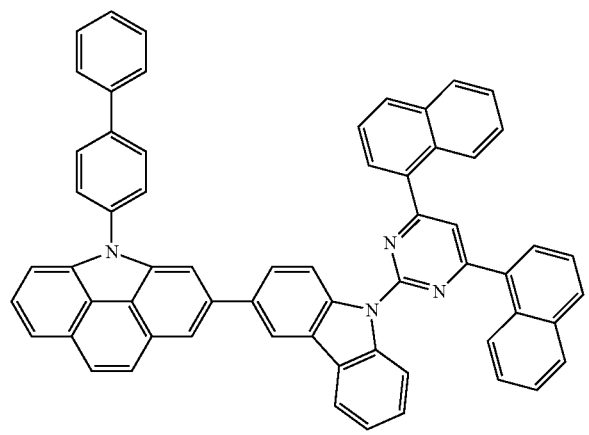
33
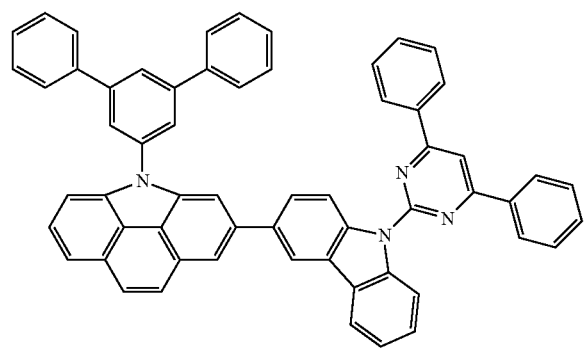
16
-continued
34
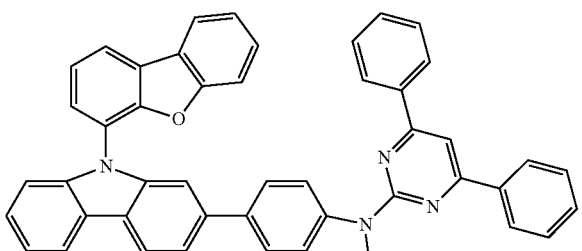
35
36
37
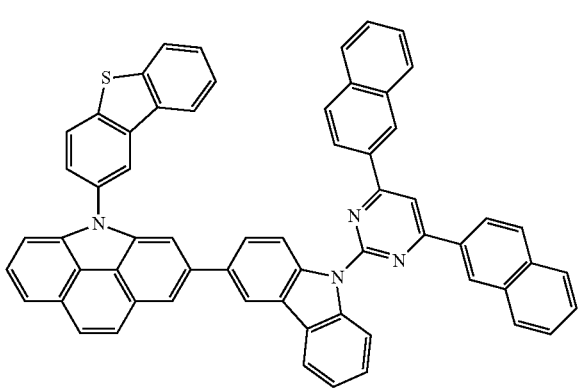

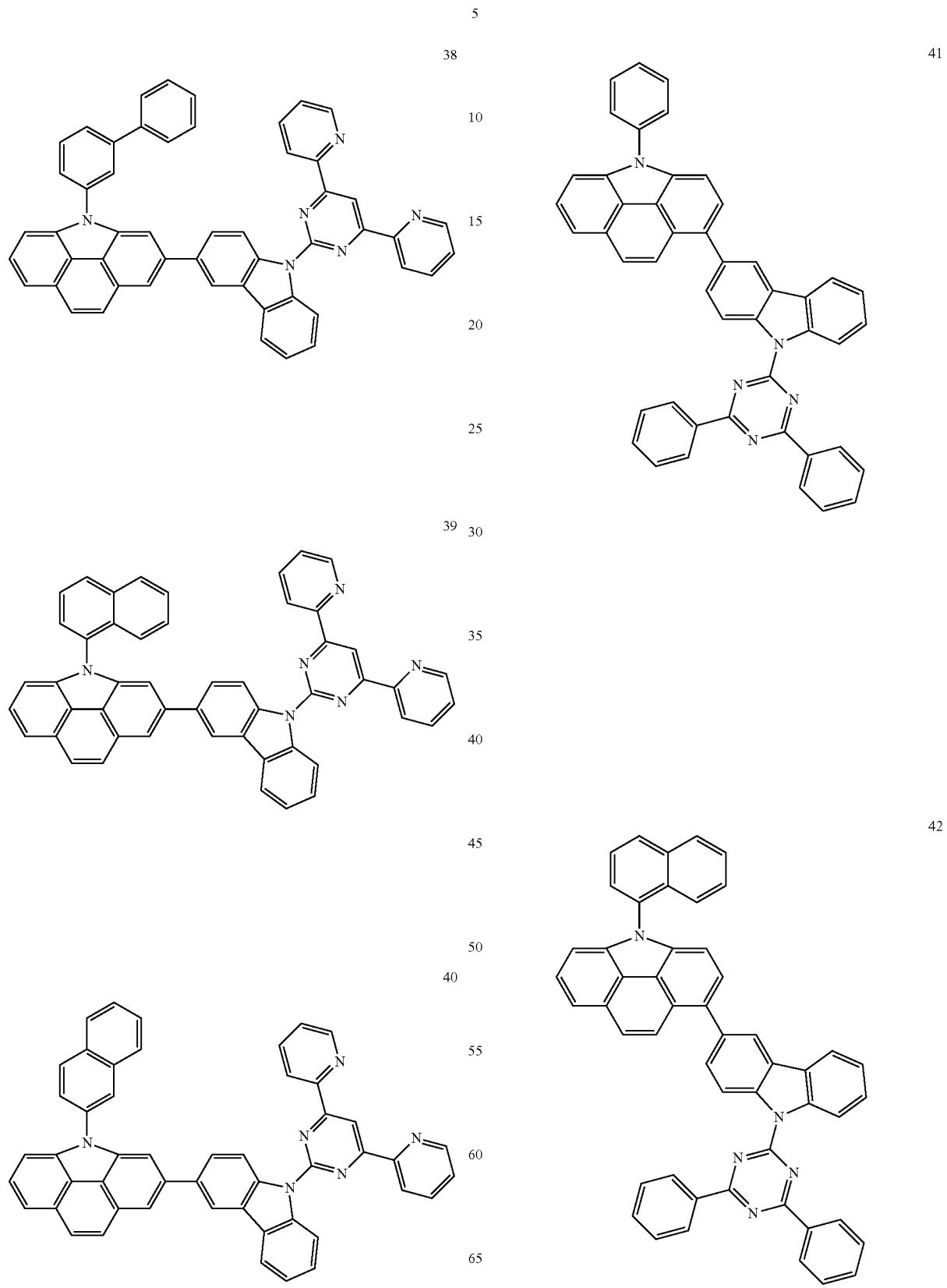

43
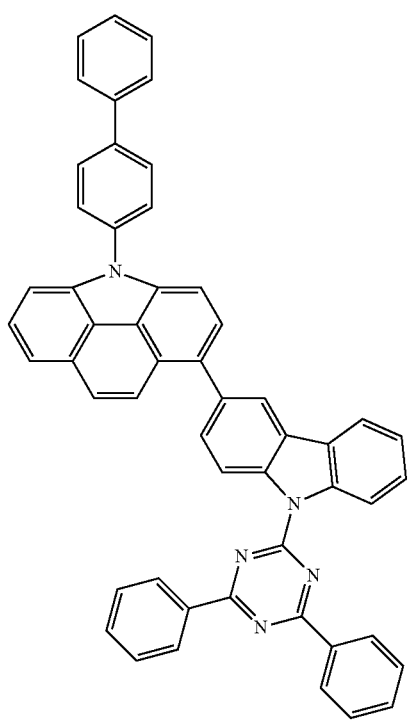
44
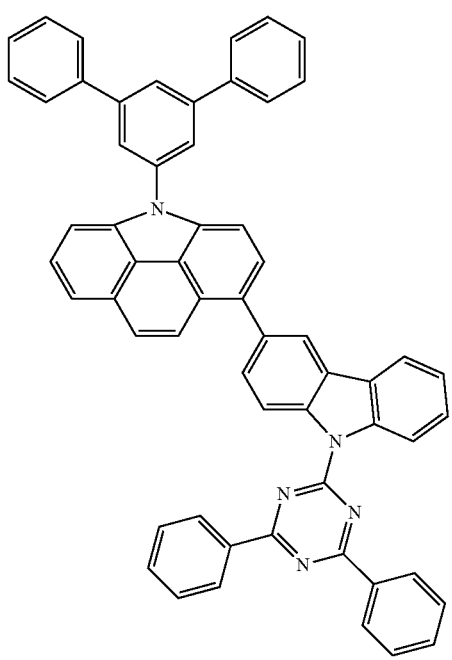
45
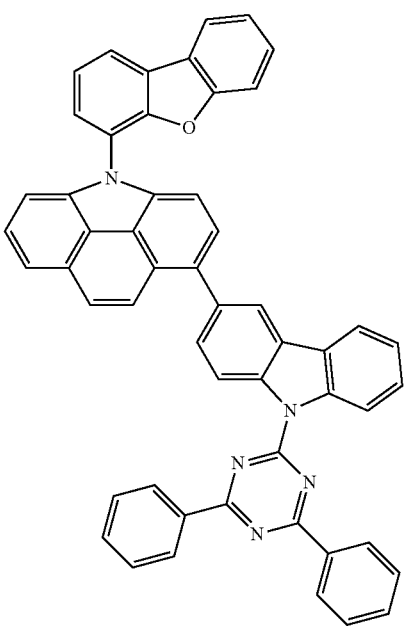
46
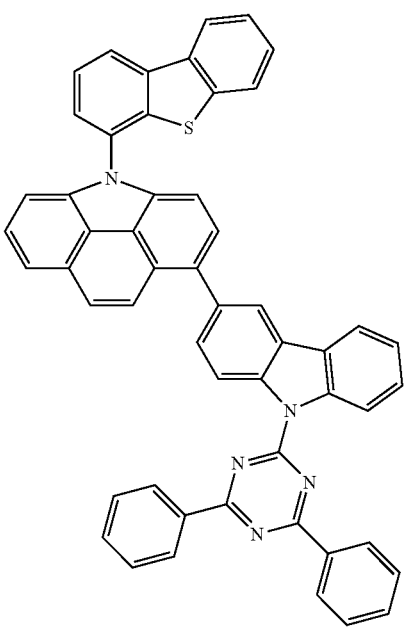

47
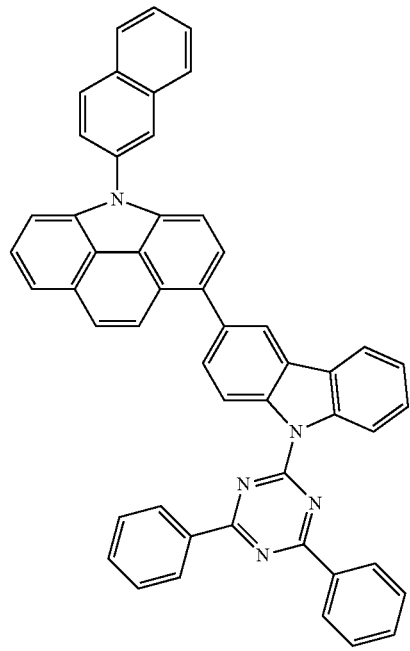
48
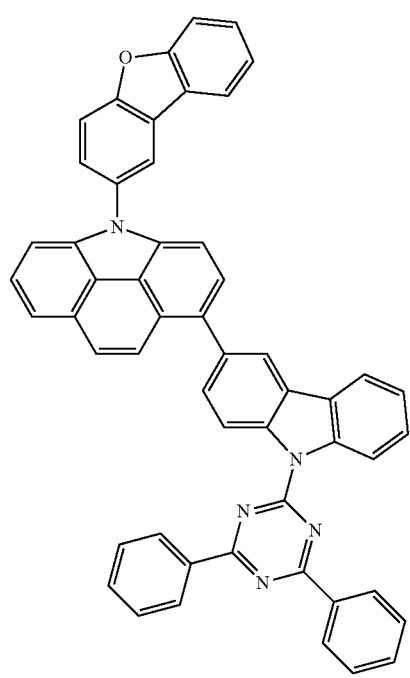
49
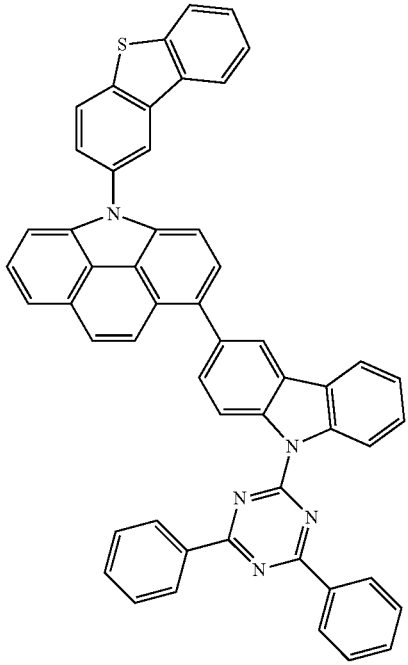
50
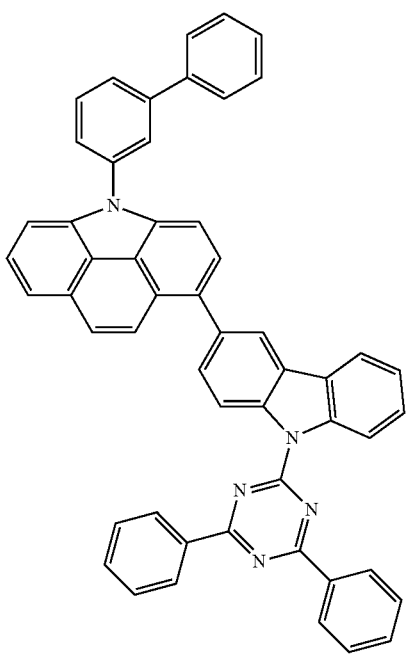

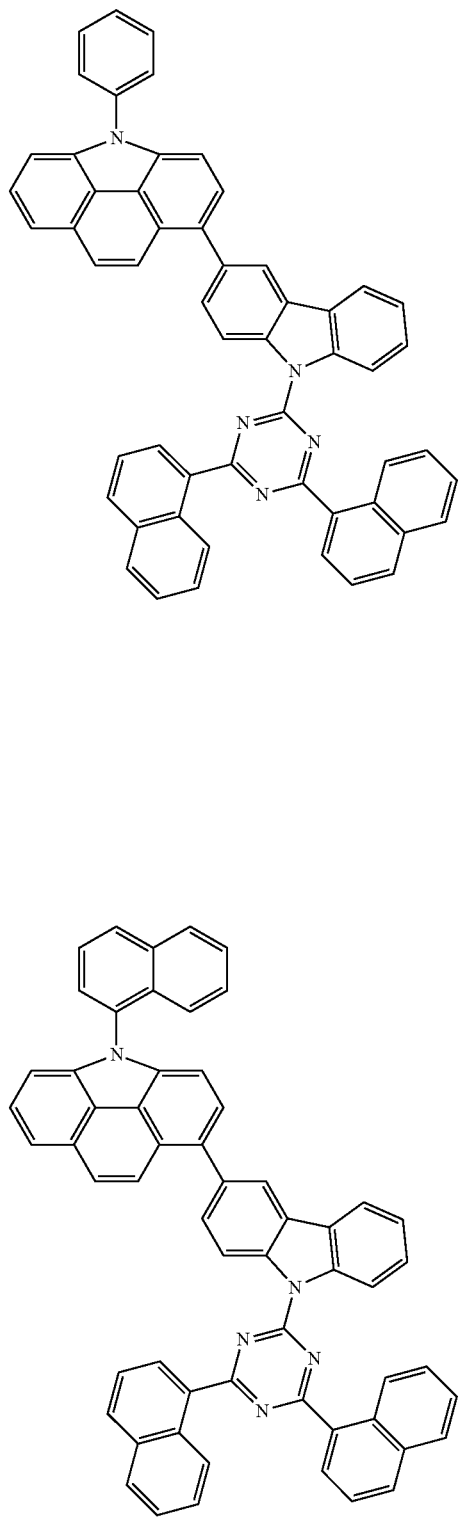
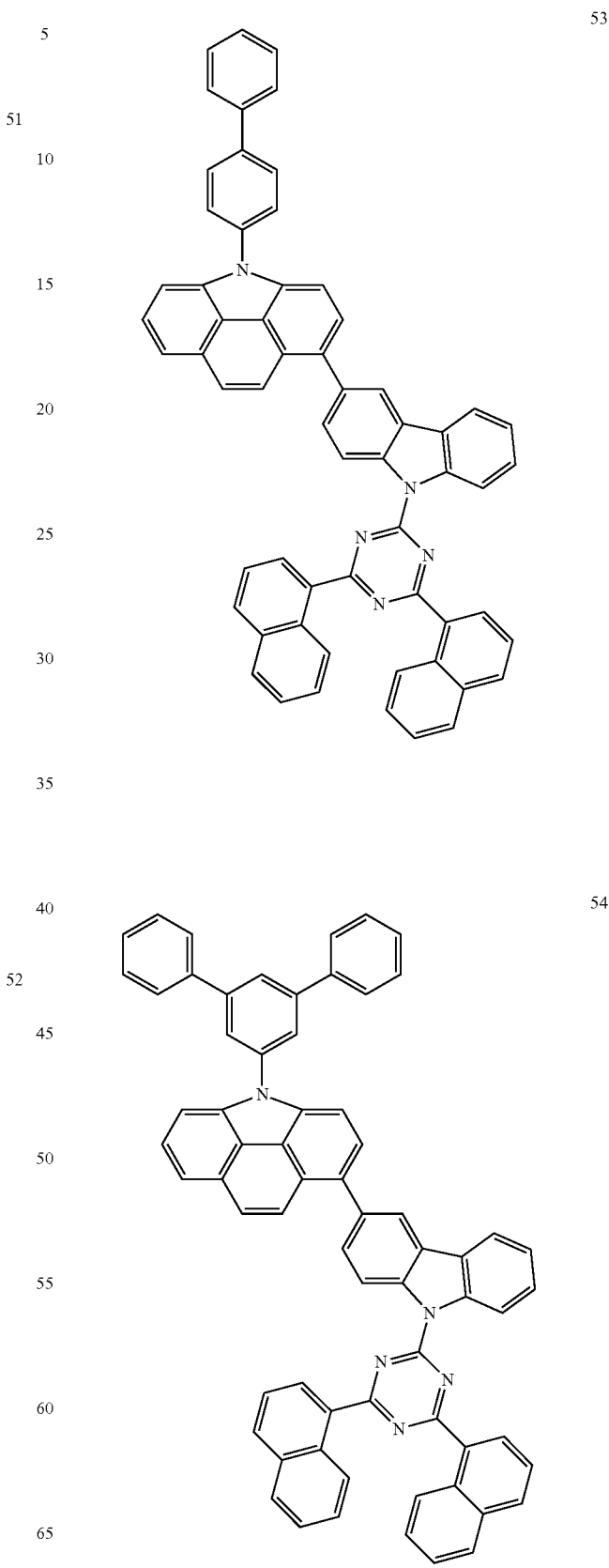

25
-continued
26
-continued
55
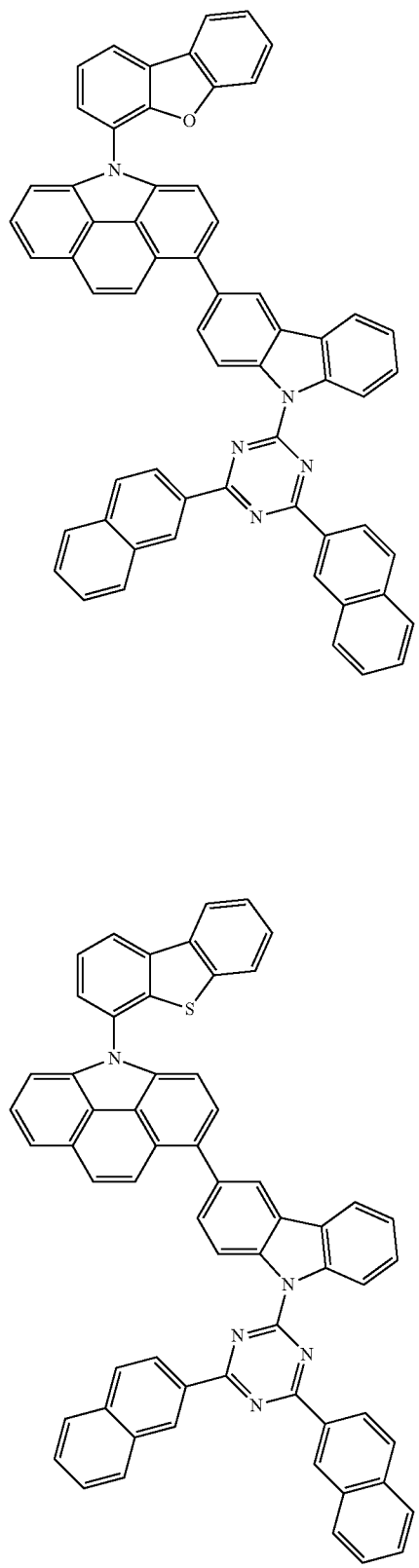
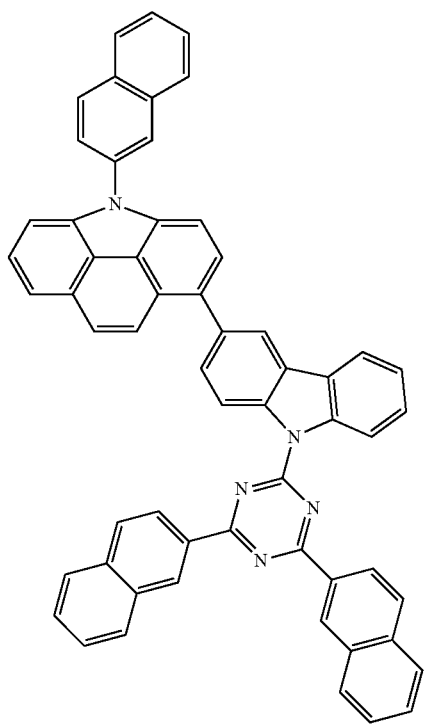
57
56
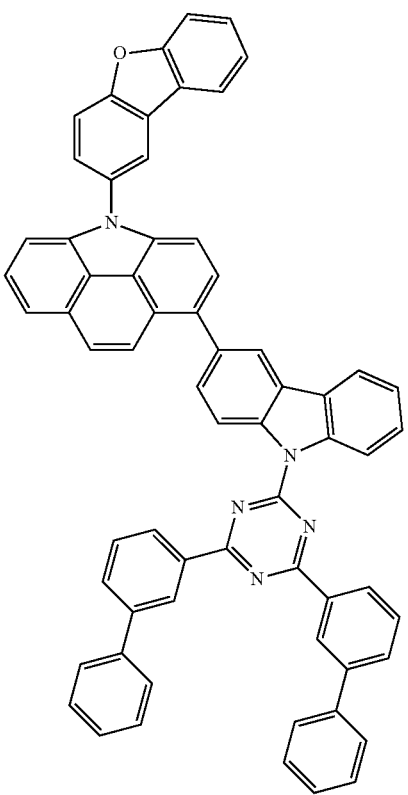
58

-continued
59
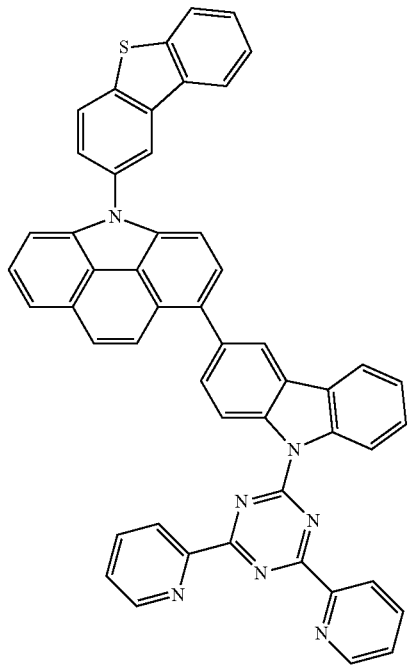
60
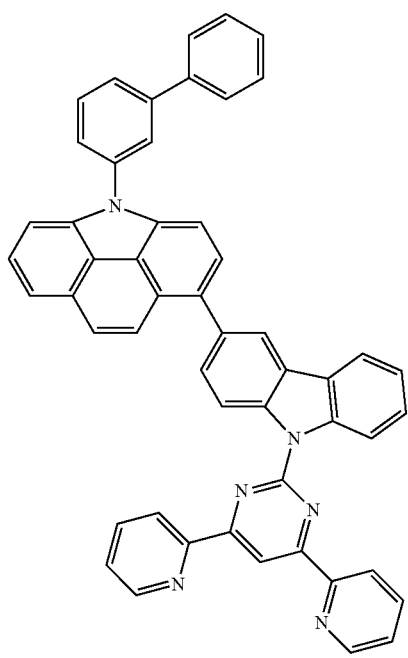
-continued
61
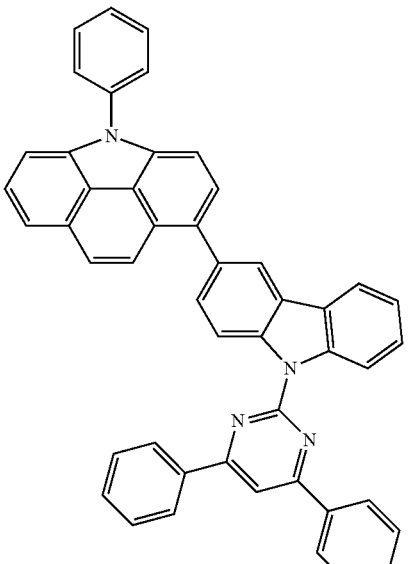
62
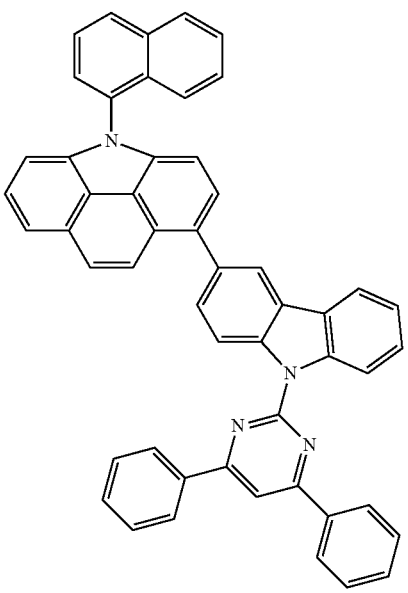

63
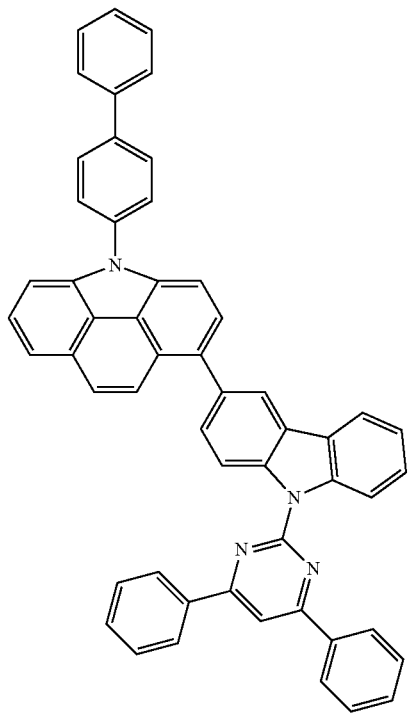
65
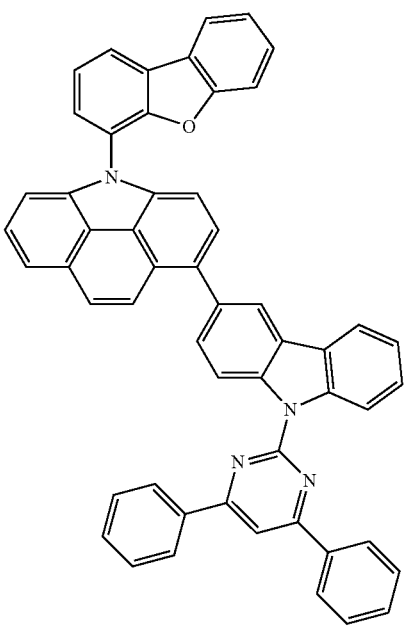
64
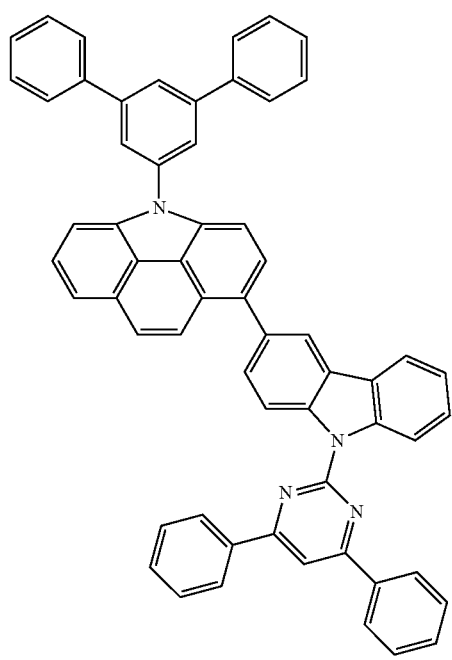
66
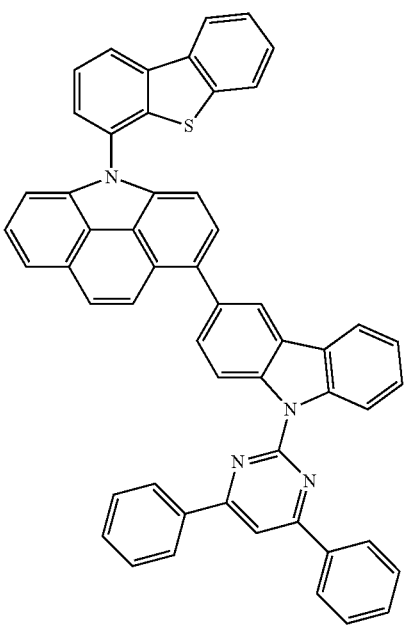

67 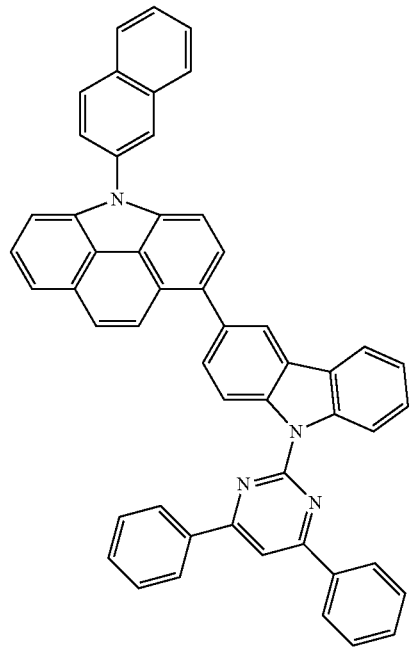
69 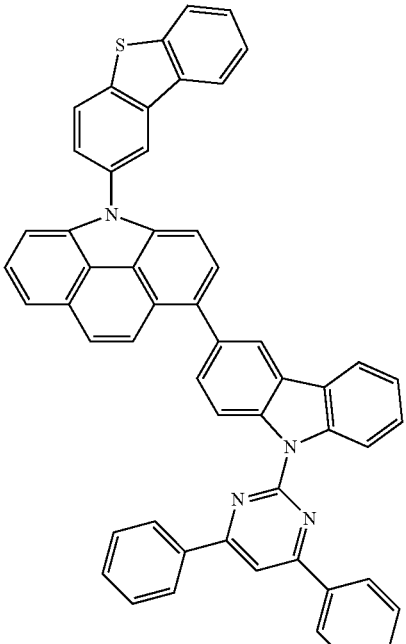
68 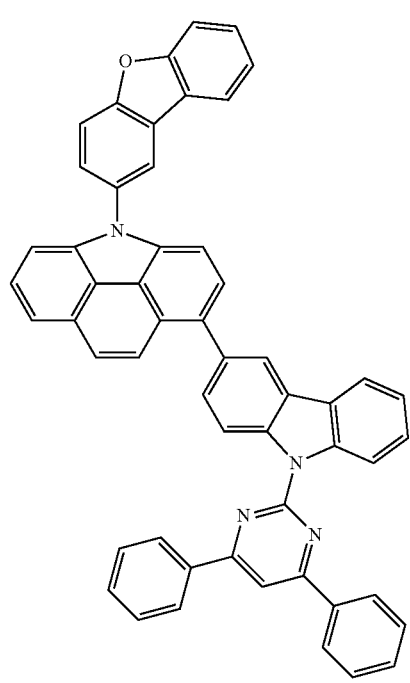
70 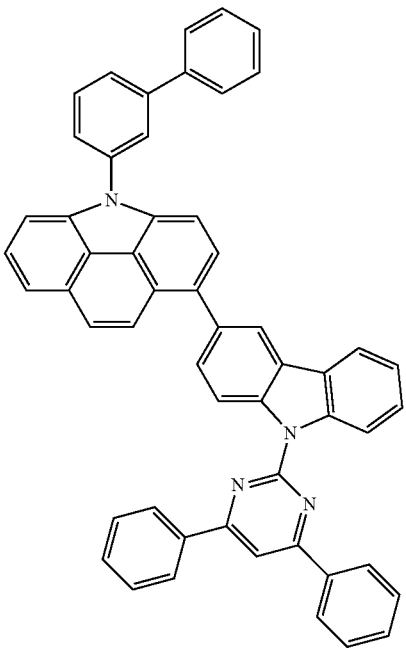

71
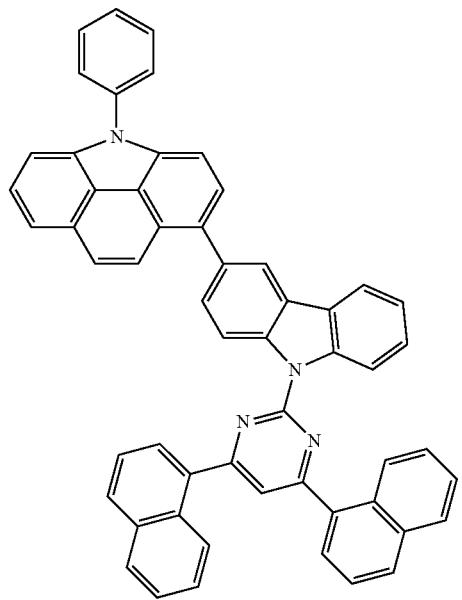
72
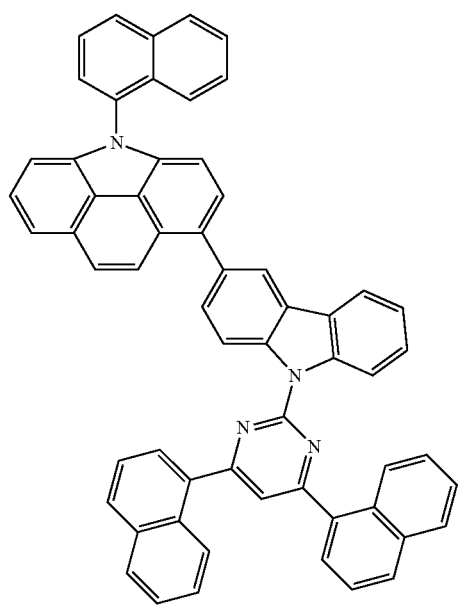
73
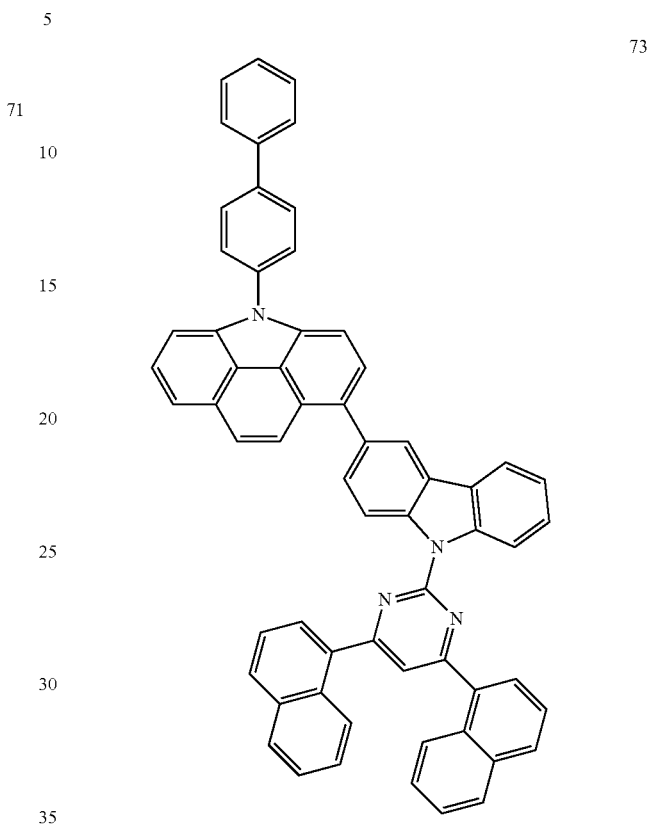
74
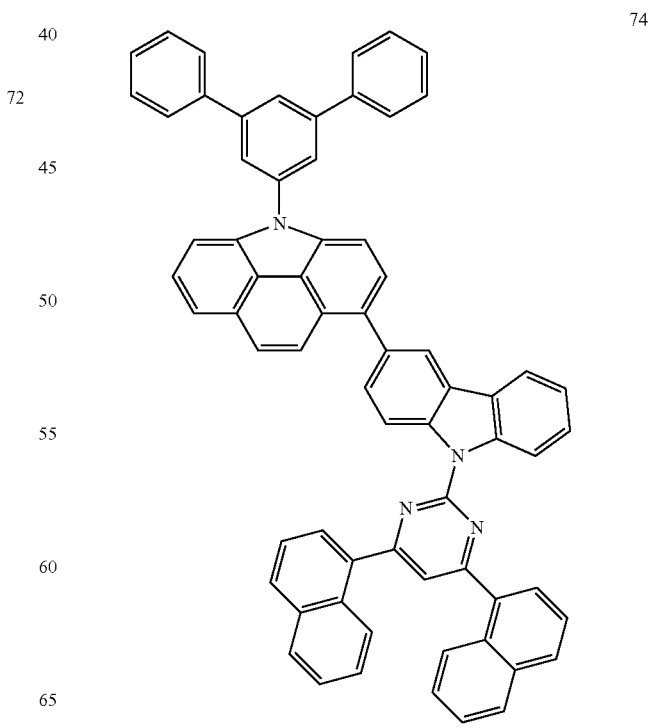

35
-continued
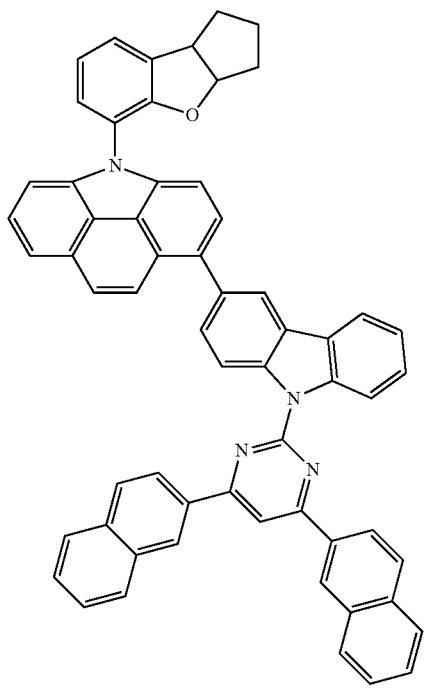
76
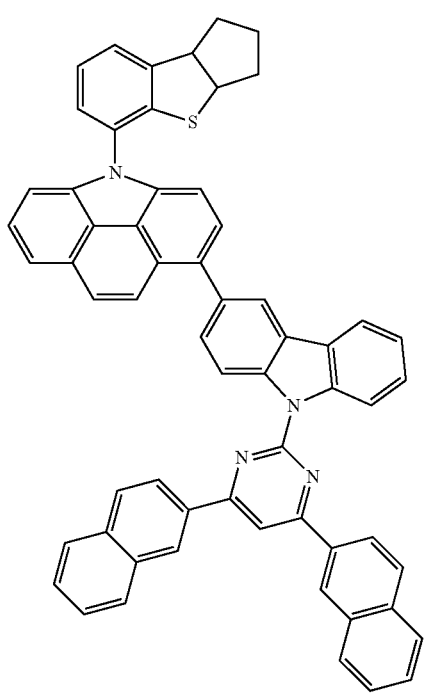
36
-continued
75
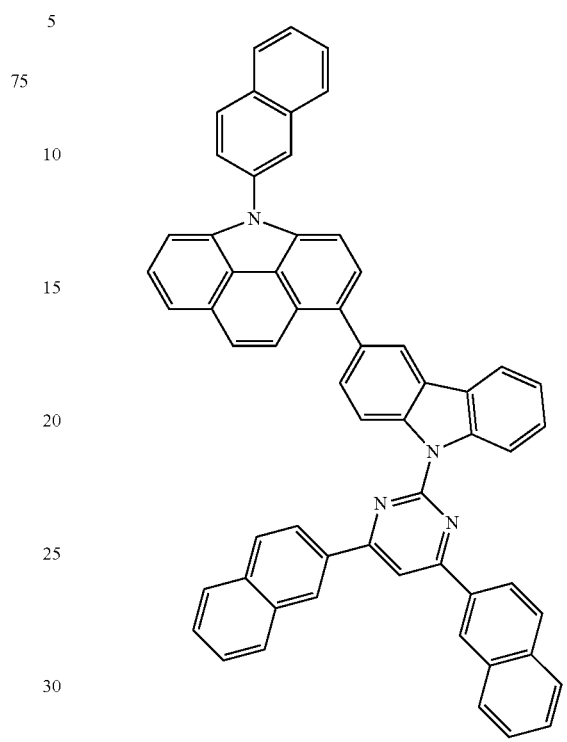
77
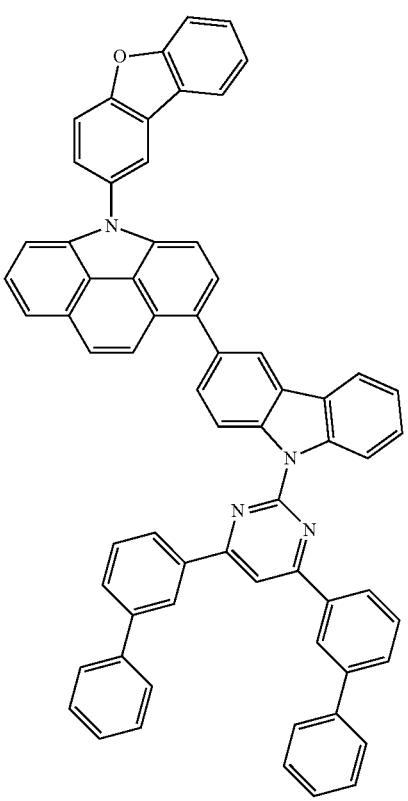
78

-continued

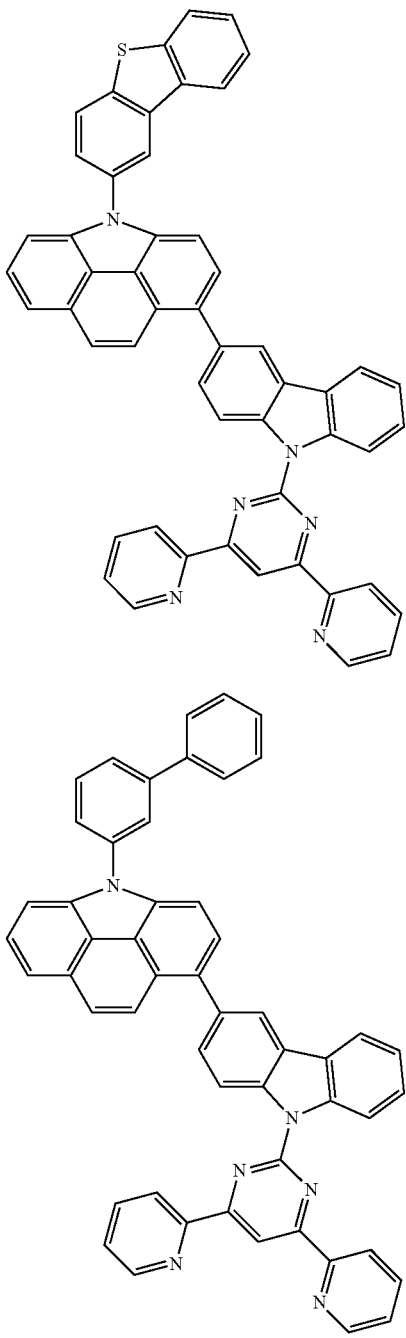

Another embodiment of the present invention provides an organic light-emitting device including a first electrode, a second electrode, and an organic layer between the first electrode and the second electrode, the organic layer including the compound of Formula 1 described above.

The organic layer may include at least one layer selected from among a hole injection layer, a hole transport layer, a functional layer having both hole injection and hole transport capabilities (hereinafter, "H-functional layer"), a buffer layer, an electron blocking layer, an emission layer, a hole blocking layer, an electron transport layer, an electron injection layer, and a functional layer having both electron injection and electron transport capabilities (hereinafter, "E-functional layer").

For example, the organic layer may be an emission layer or an electron transport layer.

In some embodiments, the organic layer may include at least one layer selected from among an electron injection layer, an electron transport layer, an emission layer, a hole injection layer, a hole transport layer, and a functional layer having both hole injection and hole transport capabilities, The emission layer may include an anthracene-based compound, an arylamine-based compound or a styryl-based compound, in addition to the compound of Formula 1 above.

In some other embodiments, the organic layer may include at least one layer selected from among an electron injection layer, an electron transport layer, an emission layer, a hole injection layer, a hole transport layer, and a functional layer having both hole injection and transport capabilities. At least one of a red emission layer, a green emission layer, a blue emission layer, and a white emission layer of the emission layer may include a phosphorescent compound; and at least one of the hole injection layer, the hole transport layer, and the functional layer having both hole injection and hole transport capabilities may include a charge-generating material. In some embodiments, the charge-generating material may be a p-type dopant, and may be selected from a quinone derivative, a metal oxide and a cyano group-containing compound.

In some embodiments, the organic layer may include an electron transport layer, and the electron transport layer may include an electron-transporting organic compound and a metal complex. The metal complex may be a lithium (Li) complex.

The term "organic layer" as used herein may refer to a single layer and/or a plurality of layers positioned between the first and second electrodes of the organic light-emitting device.

The organic layer may include an emission layer, and the emission layer may include the compound of Formula 1. The organic layer may include at least one of a hole injection layer, a hole transport layer, and a functional layer having both hole injection and hole transport capabilities (hereinafter, "H-functional layer"); and at least one of the hole injection layer, the hole transport layer, and the functional layer having both hole injection and hole transport capabilities may include the compound of Formula 1.

The drawing is a schematic sectional view of an organic light-emitting device according to an embodiment of the present invention. Hereinafter, a structure of an organic light-emitting device according to an embodiment of the present invention and a method of manufacturing the same will now be described with reference to the drawing.

A substrate (not shown) may be any substrate suitable for use in organic light emitting devices. In some embodiments the substrate may be a glass substrate or a transparent plastic substrate with strong mechanical strength, thermal stability, transparency, surface smoothness, ease of handling, and water resistance.

The first electrode may be formed by depositing or sputtering a first electrode-forming material on the substrate. When the first electrode is an anode, a material having a high work function may be used as the first electrode-forming material to facilitate hole injection. The first electrode may be a reflective electrode or a transmission electrode. Transparent and conductive materials such as (Indium Tin Oxide) ITO, (Indium Zinc Oxide) IZO, $SnO_2$, and ZnO may be used to form the first electrode, but embodiments of the invention are not limited thereto. The first electrode may be formed as a reflective electrode using magnesium (Mg), aluminum (Al), aluminum-lithium (Al—Li), calcium (Ca), magnesium-indium (Mg—In), magnesium-silver (Mg—Ag), or the like.

The first electrode may have a single-layer structure or a multi-layer structure including at least two layers. For example, the first electrode may have a three-layered structure of ITO/Ag/ITO, but is not limited thereto.

An organic layer is positioned on the first electrode.

The organic layer may include a hole injection layer (HIL), a hole transport layer (HTL), a buffer layer (not shown), an emission layer (EML), an electron transport layer (ETL), and an electron injection layer (EIL).

The HIL may be formed on the first electrode by vacuum deposition, spin coating, casting, Langmuir-Blodgett (LB) deposition, or the like.

When the HIL is formed using vacuum deposition, vacuum deposition conditions may vary according to the compound that is used to form the HIL, and the desired structure and thermal properties of the HIL to be formed. For example, vacuum deposition may be performed at a temperature of about 100° C. to about 500° C., a pressure of about $10^{-8}$ torr to about $10^{-3}$ torr, and a deposition rate of about 0.01 to about 100 Å/sec. However, the deposition conditions are not limited thereto.

When the HIL is formed using spin coating, the coating conditions may vary according to the compound that is used to form the HIL, and the desired structure and thermal properties of the HIL to be formed. For example, the coating rate may be in the range from about 2,000 rpm to about 5,000 rpm, and a temperature at which heat treatment is performed to remove a solvent after coating may be in the range from about 80° C. to about 200° C. However, the coating conditions are not limited thereto.

The HIL may be formed of any hole-injection material suitable for use in organic light-emitting devices. Non-limiting examples of the material that can be used to form the HIL are N,N'-diphenyl-N,N'-bis-[4-(phenyl-m-tolyl-amino)-phenyl]-biphenyl-4,4'-diamine, (DNTPD), a phthalocyanine compound such as copperphthalocyanine, 4,4',4''-tris(3-methylphenylphenylamino)triphenylamine (m-MTDATA), N,N'-di(1-naphthyl)-N,N'-diphenylbenzidine (NPB), TDATA, 2T-NATA, polyaniline/dodecylbenzenesulfonic acid (Pani/DBSA), poly(3,4-ethylenedioxythiophene)/poly (4-styrenesulfonate) (PEDOT/PSS), polyaniline/camphor sulfonicacid (Pani/CSA), and polyaniline)/poly(4-styrenesulfonate (PANI/PSS).

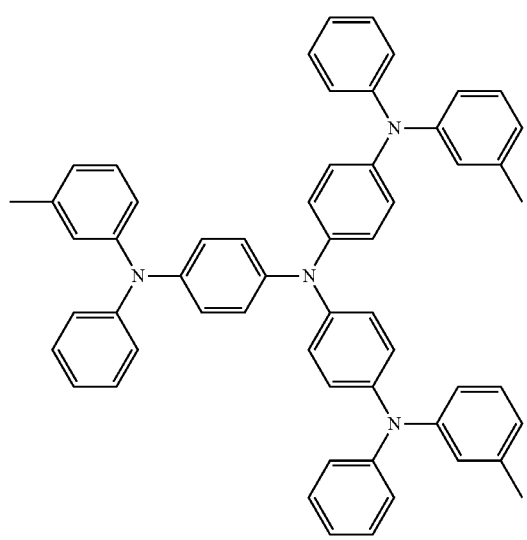

m-MTDATA

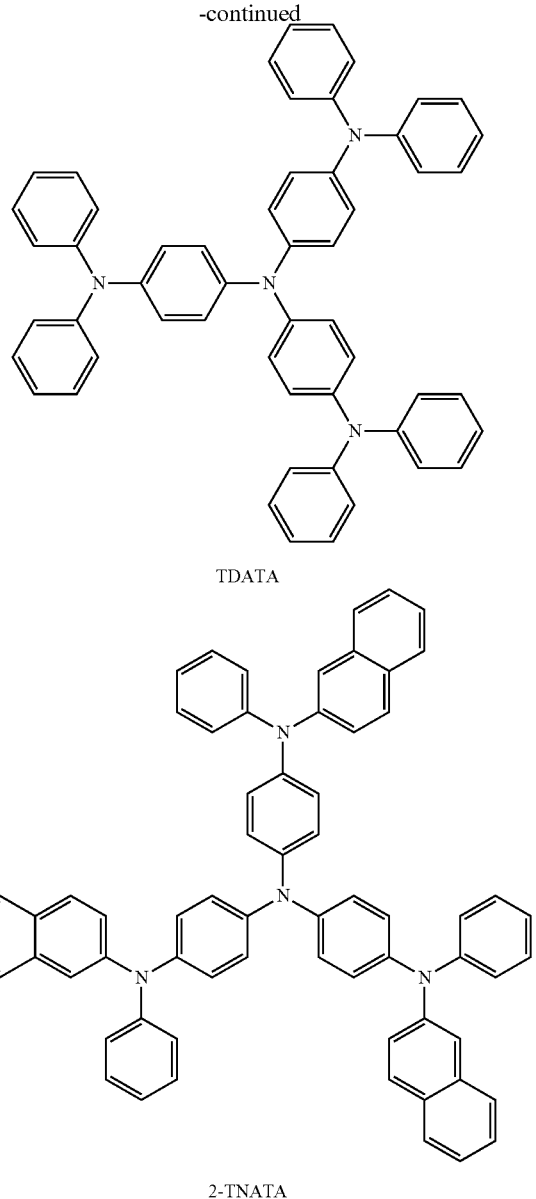

TDATA

2-TNATA

The thickness of the HIL may be from about 100 Å to about 10,000 Å, and in some embodiments, may be from about 100 Å to about 1,000 Å. When the thickness of the HIL is within these ranges, the HIL may have good hole injecting ability without a substantial increase in driving voltage.

The HTL may be formed on the HIL using vacuum deposition, spin coating, casting, Langmuir-Blodgett (LB) deposition, or the like. When the HTL is formed using vacuum deposition or spin coating, the conditions for deposition and coating may be similar to those for the formation of the HIL, though the conditions for the deposition and coating may vary according to the material that is used to form the HTL.

The HTL may be formed of any hole-transporting material suitable for use in organic light-emitting devices. Non-limiting examples of suitable HTL forming materials are carbazole derivatives, such as N-phenylcarbazole or polyvinylcarbazole, N,N'-bis(3-methylphenyl)-N,N'-diphenyl-[1,1-biphenyl]-4,4'-diamine (TPD), 4,4',4''-tris(N-carbazolyl) triphenylamine (TCTA), and N,N'-di(1-naphthyl)-N,N'-diphenylbenzidine) (NPB).

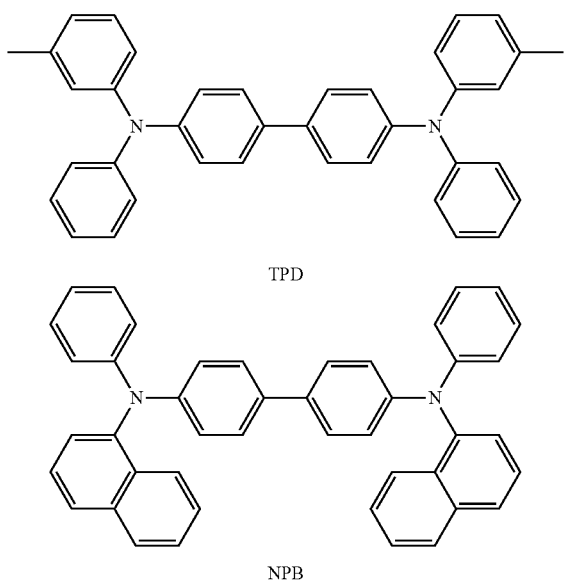

TPD

NPB

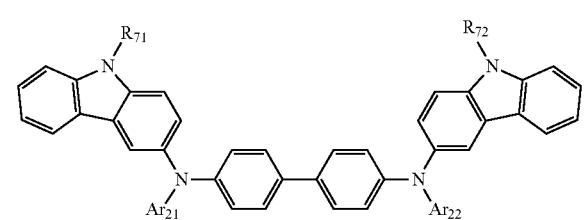

Formula 350

The thickness of the HTL may be from about 50 Å to about 2,000 Å, and in some embodiments, may be from about 100 Å to about 1,500 Å. When the thickness of the HTL is within these ranges, the HTL may have good hole transporting ability without a substantial increase in driving voltage.

An H-functional layer (having both hole injection and hole transport capabilities) may contain at least one material from each group of the hole injection layer materials and the hole transport layer materials. The thickness of the H-functional layer may be from about 500 Å to about 10,000 Å, and in some embodiments, may be from about 100 Å to about 1,000 Å. When the thickness of the H-functional layer is within these ranges, the H-functional layer may have good hole injection and hole transport capabilities without a substantial increase in driving voltage.

In some embodiments, at least one of the HIL, the HTL, and the H-functional layer may include at least one of the compounds represented by Formula 300 below and the compounds represented by Formula 350 below:

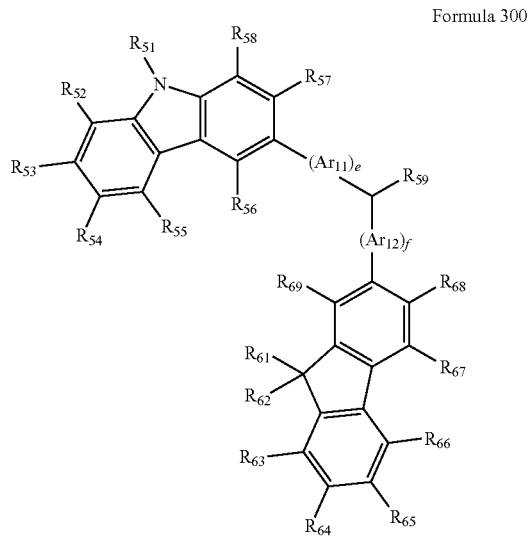

Formula 300

In Formulae 300 and 350, $Ar_{11}$ and $Ar_{12}$ may be each independently a substituted or unsubstituted $C_5$-$C_{60}$ arylene group, and $Ar_{21}$ and $Ar_{22}$ may be each independently a substituted or unsubstituted $C_6$-$C_{60}$ aryl group.

In Formula 300, e and f may be each independently an integer from 0 to 5, and in some embodiments may be 0, 1, or 2. For example, e may be 1, and f may be 0, but embodiments of the invention are not limited thereto.

In Formulae 300 and 350 above, $R_{51}$ to $R_{58}$, $R_{61}$ to $R_{69}$, and $R_{71}$ and $R_{72}$ may be each independently selected from a hydrogen atom, a deuterium atom, a halogen atom, a hydroxyl group, a cyano group, a nitro group, an amino group, an amidino group, a hydrazine group, a hydrazone, a carboxyl group or a salt thereof, a sulfonic acid group or a salt thereof, a phosphoric acid group or a salt thereof, a substituted or unsubstituted $C_1$-$C_{60}$ alkyl group, a substituted or unsubstituted $C_2$-$C_{60}$ alkenyl group, a substituted or unsubstituted $C_2$-$C_{60}$ alkynyl group, a substituted or unsubstituted $C_1$-$C_{60}$ alkoxy group, a substituted or unsubstituted $C_3$-$C_{60}$ cycloalkyl group, a substituted or unsubstiuted $C_6$-$C_{60}$ aryl group, a substituted or unsubstituted $C_5$-$C_{60}$ aryloxy group, and a substituted or unsubstituted $C_5$-$C_{60}$ arylthio group. In some embodiments, $R_{51}$ to $R_{58}$, $R_{61}$ to $R_{69}$, $R_{71}$, and $R_{72}$ may be each independently selected from a hydrogen atom; a deuterium atom; a halogen atom; a hydroxyl group; a cyano group; a nitro group; an amino group; an amidino group; a hydrazine; a hydrazone; a carboxyl group or a salt thereof; a sulfonic acid group or a salt thereof; a phosphoric acid group or a salt thereof; a $C_1$-$C_{10}$ alkyl group (for example, a methyl group, an ethyl group, a propyl group, a butyl group, a pentyl group, a hexyl group, or the like); a $C_1$-$C_{10}$ alkoxy group (for example, a methoxy group, an ethoxy group, a propoxy group, a butoxy group, a pentoxy group, or the like); a $C_1$-$C_{10}$ alkyl group and a $C_1$-$C_{10}$ alkoxy group that are substituted with at least one selected from a deuterium atom, a halogen atom, a hydroxyl group, a cyano group, a nitro group, an amino group, an amidino group, a hydrazine, a hydrazone, a carboxyl group or a salt thereof, a sulfonic acid group or a salt thereof, and a phosphoric acid group or a salt thereof; a phenyl group; a naphthyl group; an anthryl group; a fluorenyl group; a pyrenyl group; and a phenyl group, a naphthyl group, an anthryl group, a fluorenyl group, and a pyrenyl group that are substituted with at least one selected from a deuterium atom, a halogen atom, a hydroxyl group, a cyano group, a nitro group, an amino group, an amidino group, a hydrazine, a hydrazone, a carboxyl group or a salt thereof, a sulfonic acid group or a salt thereof, a phosphoric acid group or a salt thereof, a $C_1$-$C_{10}$ alkyl group, and a $C_1$-$C_{10}$ alkoxy group.

In Formula 300, $R_{59}$ may be selected from a phenyl group, a naphthyl group, an anthryl group, a biphenyl group, a pyridyl group; and a phenyl group, a naphthyl group, an anthryl group, a biphenyl group, and a pyridyl group that are substituted with at least one selected from a deuterium atom, a halogen atom, a hydroxyl group, a cyano group, a nitro group, an amino group, an amidino group, a hydrazine, a hydrazone, a carboxyl group or a salt thereof, a sulfonic acid group or a salt thereof, a phosphoric acid group or a salt thereof, a substituted or unsubstituted $C_1$-$C_{20}$ alkyl group, and a substituted or unsubstituted $C_1$-$C_{20}$ alkoxy group.

In an embodiment of the present invention the compound of Formula 300 may be a compound represented by Formula 300A below:

Formula 300A

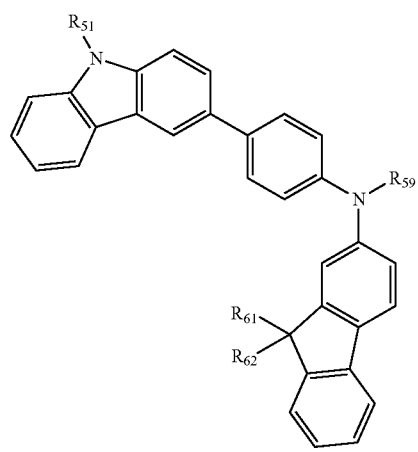

In Formula 300A, $R_{51}$, $R_{59}$, $R_{60}$, and $R_{61}$ may be as defined above.

In some non-limiting embodiments, at least one of the HIL, the HTL, and the H-functional layer may include at least one of the compounds represented by Formulae 301 to 320 below:

301

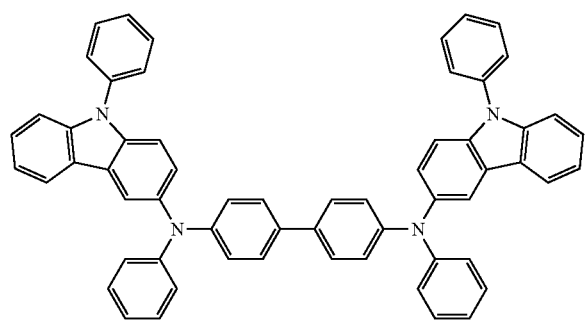

302

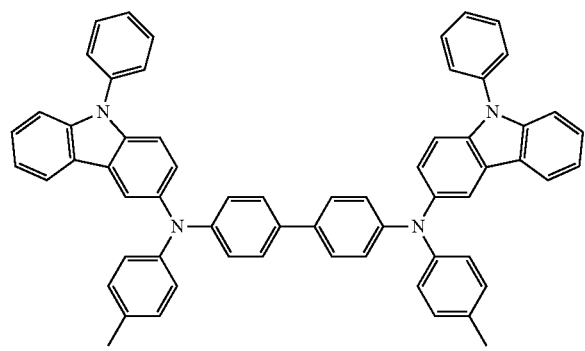

303

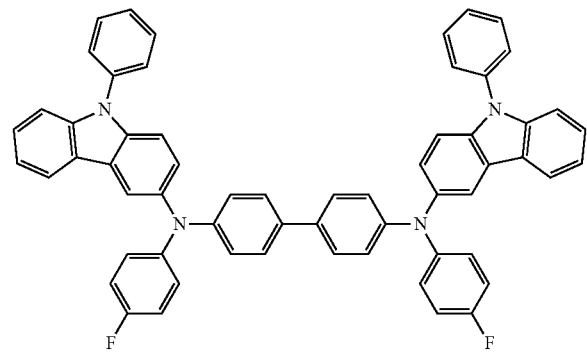

304

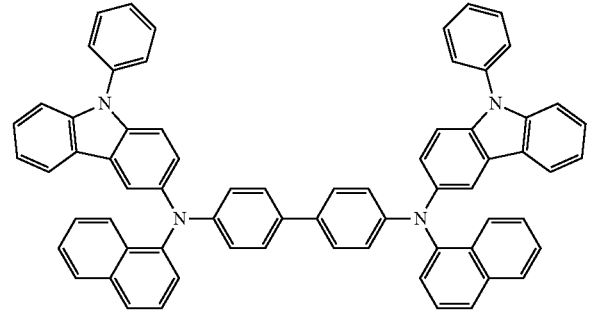

305

306

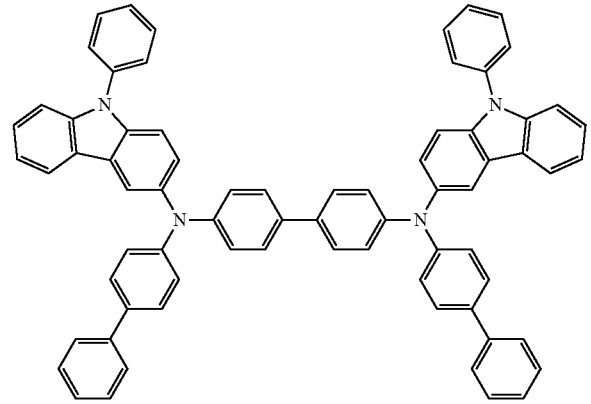

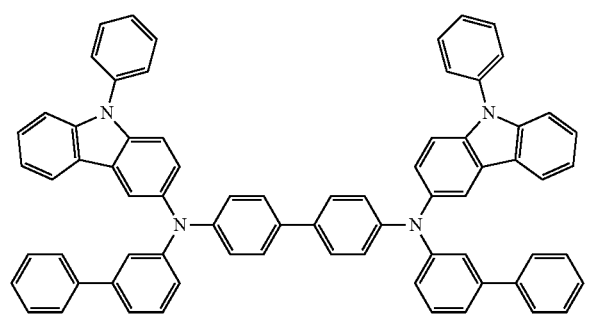
307
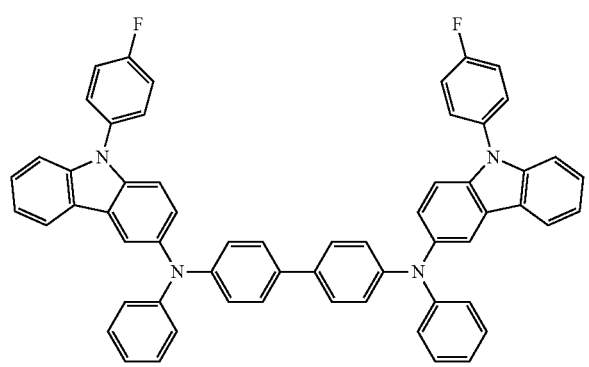
308
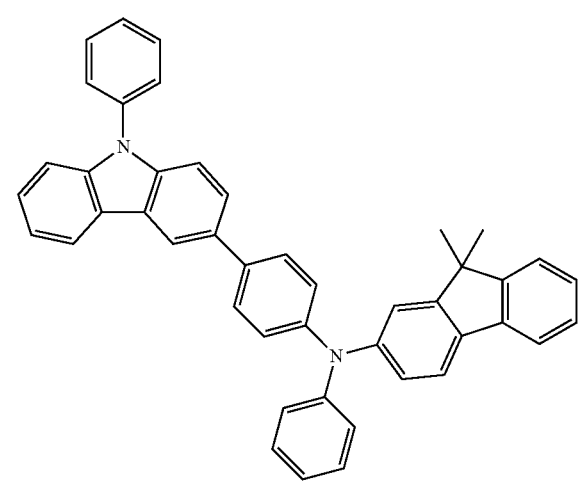
309
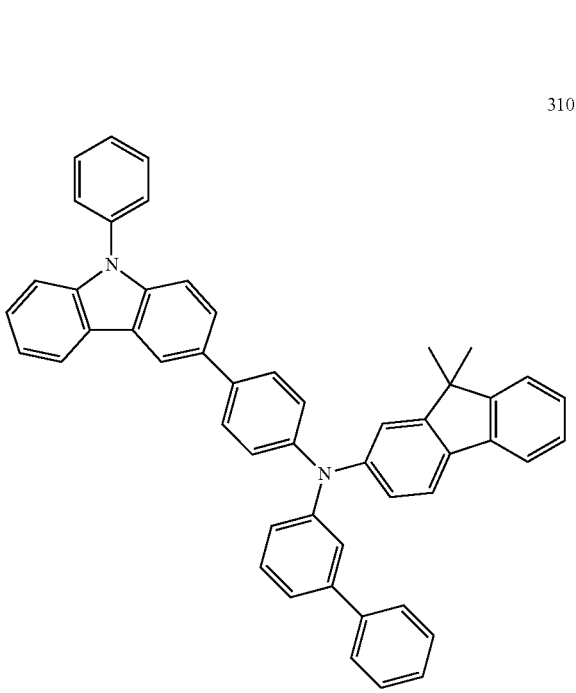
310
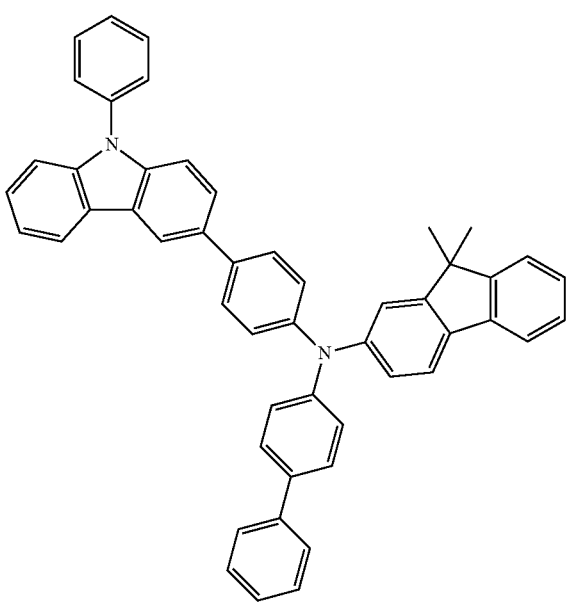
311

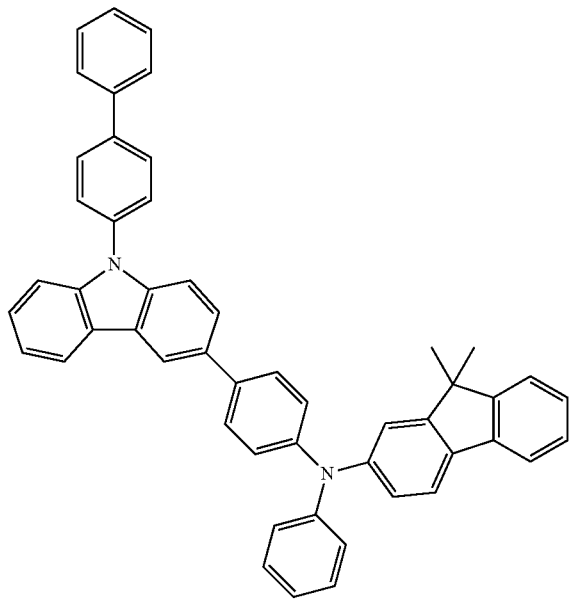
312
313
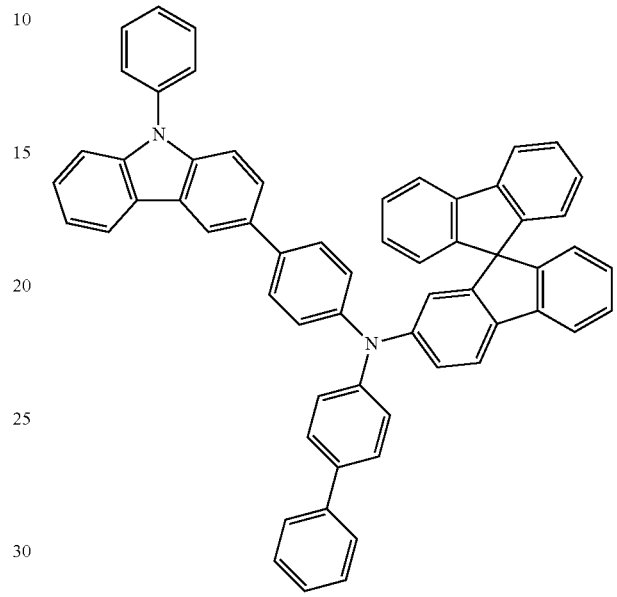
314
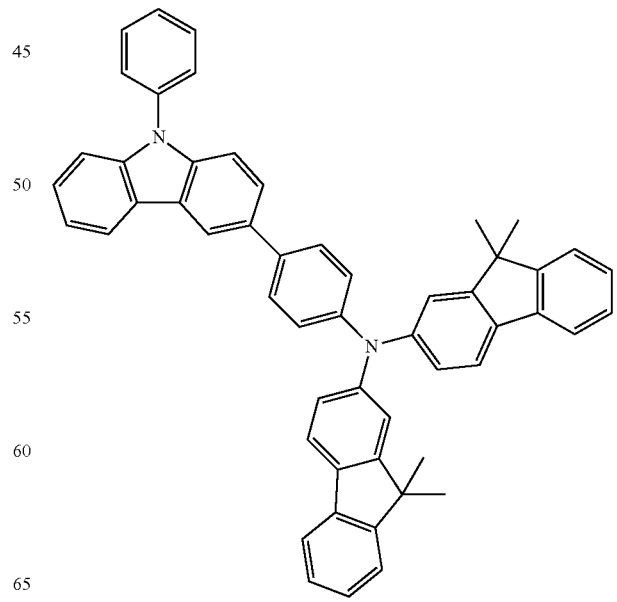
315

316

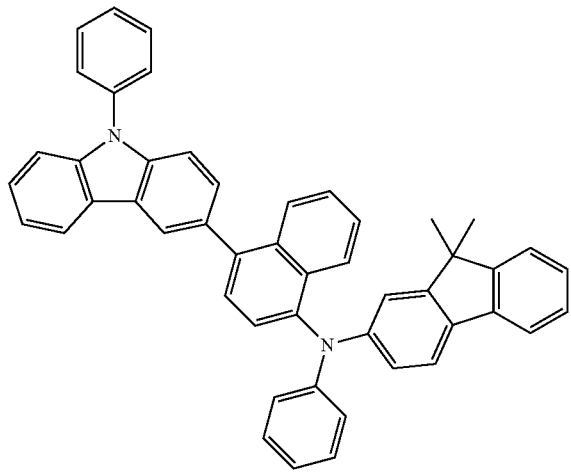

317

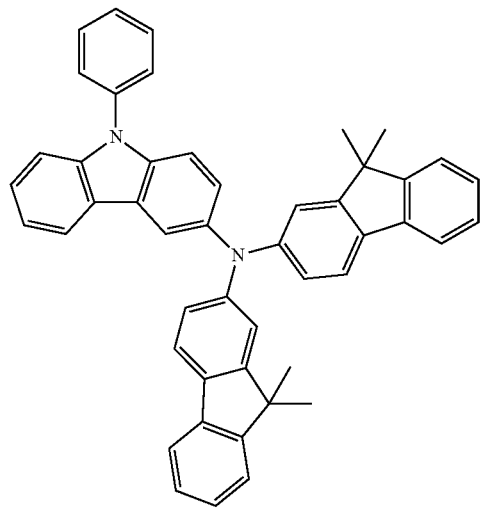

318

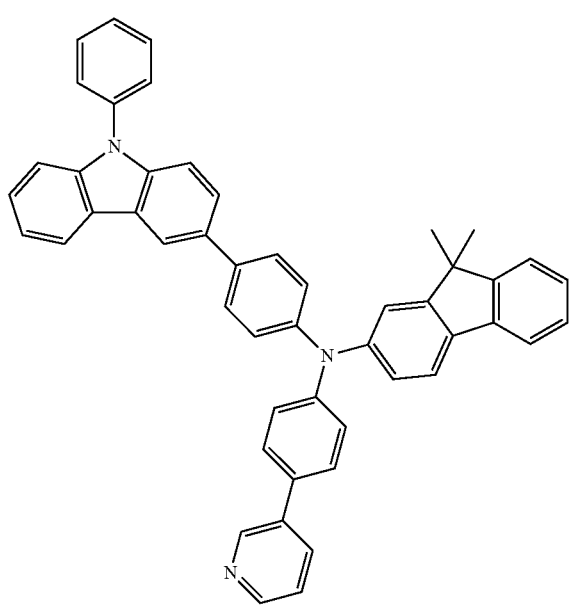

319

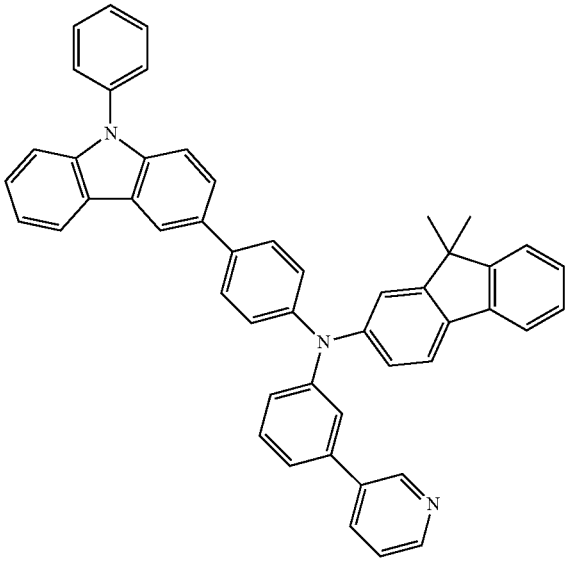

320

At least one of the HIL, the HTL, and the H-functional layer may further include a charge-generating material for improved layer conductivity, in addition to the hole injecting material, hole transport material, and/or material having both hole injection and hole transport capabilities as described above.

The charge-generating material may be, for example, a p-dopant. The p-dopant may be selected from quinone derivatives, metal oxides, and compounds with a cyano group, but embodiments of the invention are not limited thereto. Non-limiting examples of the p-dopant are quinone derivatives such as tetracyanoquinonedimethane (TCNQ), 2,3,5,6-tetrafluoro-tetracyano-1,4-benzoquinonedimethane (F4-TCNQ), and the like; metal oxides such as tungsten oxide, molybdenum oxide, and the like; and cyano-containing compounds such as Compound 200 below.

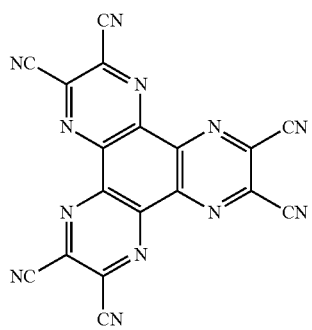
Compound 200

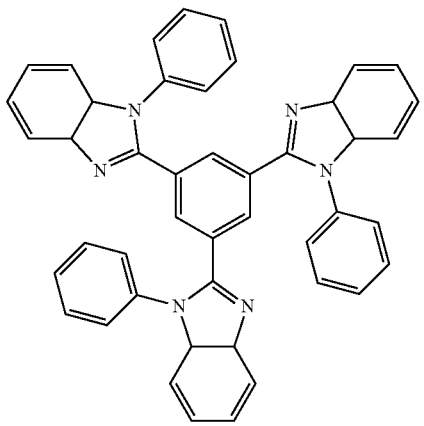
TPBI

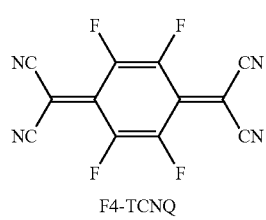
F4-TCNQ

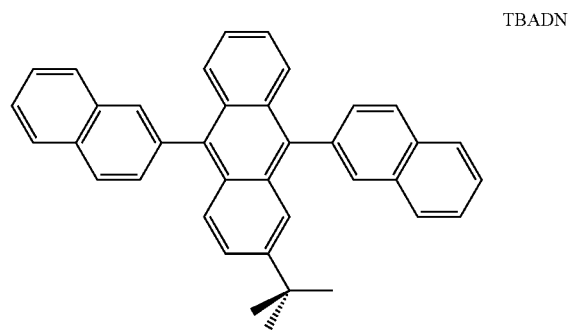
TBADN

When the hole injection layer, the hole transport layer, or the H-functional layer further includes a charge-generating material, the charge-generating material may be homogeneously dispersed or inhomogeneously distributed in the layer.

A buffer layer may be positioned between at least one of the HIL, the HTL, and the H-functional layer, and the EML. The buffer layer may compensate for an optical resonance distance of light according to a wavelength of the light emitted from the EML, and thus may increase efficiency. The buffer layer may include any hole injecting material or hole transporting material that are suitable for use in organic light-emitting devices. In some other embodiments, the buffer layer may include the same material as one of the materials included in the HIL, the HTL, and the H-functional layer.

An EML may be formed on the HTL, the H-functional layer, or the buffer layer by vacuum deposition, spin coating, casting, Langmuir-Blodget (LB) deposition, or the like. When the EML is formed using vacuum deposition or spin coating, the deposition and coating conditions may be similar to those for the formation of the HIL, though the conditions for deposition and coating may vary according to the material that is used to form the EML.

The EML may be formed using a host and a dopant that are suitable for use in organic light-emitting devices. Non-limiting examples of the dopant for use in the EML are a fluorescent dopant and a phosphorescent dopant.

Non-limiting examples of the host are Alq$_3$, 4,4'-N,N'-dicarbazole-biphenyl (CBP), poly(n-vinylcarbazole) (PVK), 9,10-di(naphthalene-2-yl)anthracene (ADN), TCTA, 1,3,5-tris(N-phenylbenzimidazole-2-yl)benzene (TPBI), 3-tert-butyl-9,10-di-2-naphthylanthracene (TBADN), E3, distyrylarylene (DSA), dmCBP (shown below), and Compounds 501 to 509 below.

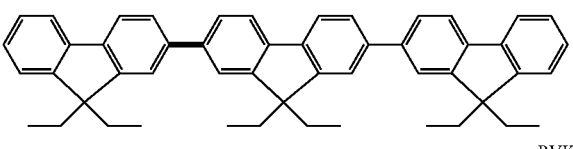
E3

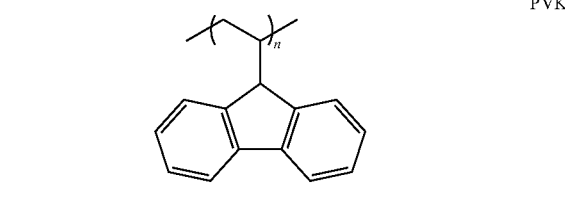
PVK

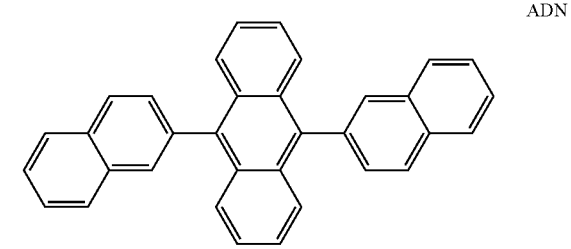
ADN

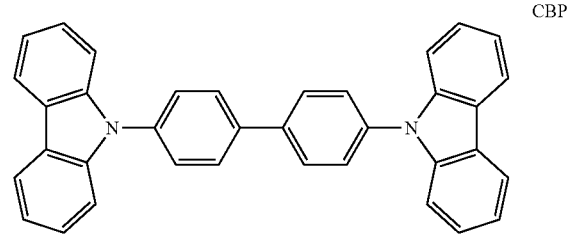
CBP dmCBP
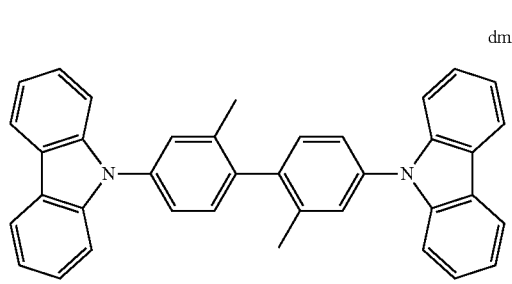
501
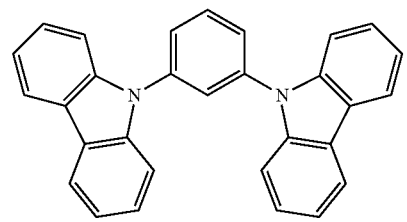
502
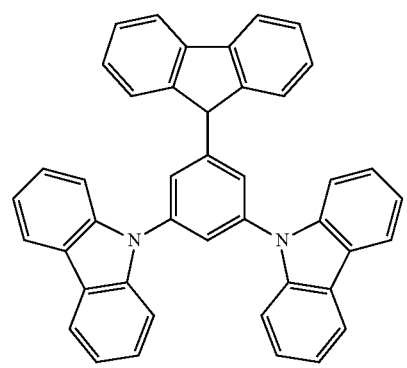
503
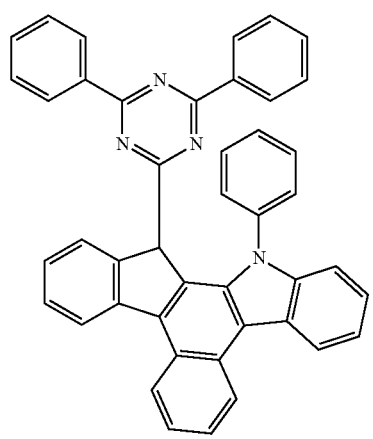
504
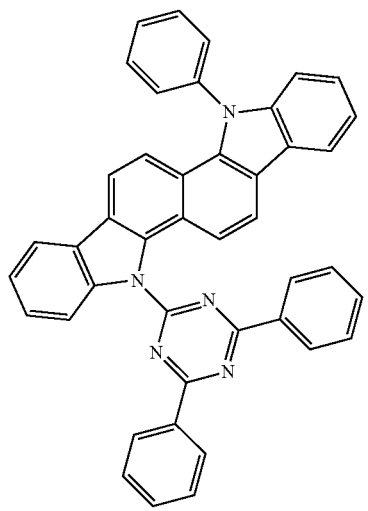
505
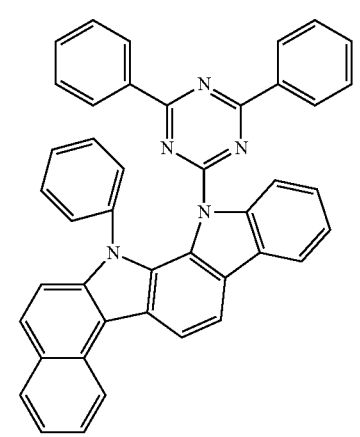
506
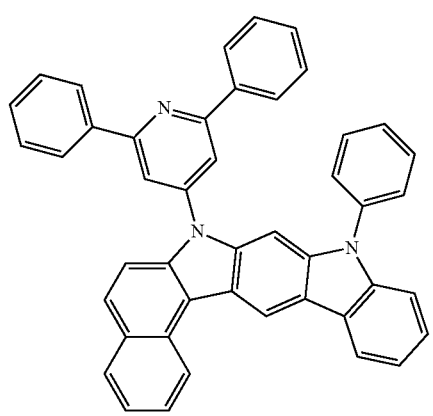

507

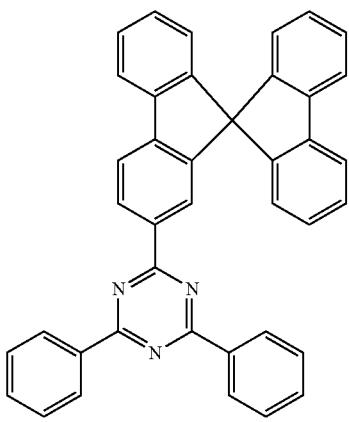

508

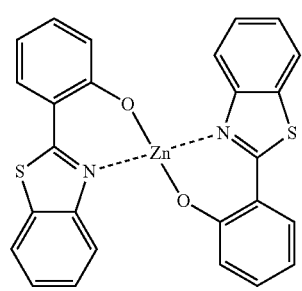

509

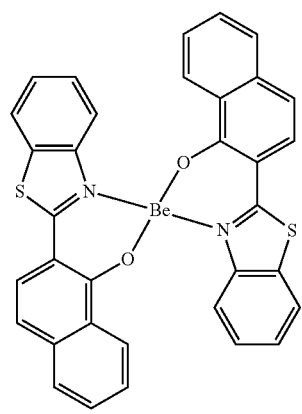

In some embodiments, an anthracene-based compound represented by Formula 400 below may be used as the host.

Formula 400

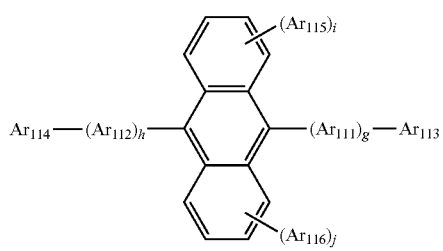

In Formula 400, $Ar_{111}$ and $Ar_{112}$ are each independently a substituted or unsubstituted $C_6$-$C_{60}$ arylene group; $Ar_{113}$ to $Ar_{116}$ are each independently a substituted or unsubstituted $C_1$-$C_{10}$ alkyl group, or a substituted or unsubstituted $C_6$-$C_{60}$ aryl group; and g, h, i, and j are each independently an integer from 0 to 4.

In some embodiments, $Ar_{111}$ and $Ar_{112}$ in Formula 400 may be each independently selected from a phenylene group, a naphthylene group, a phenanthrenylene group, a pyrenylene group; and a phenylene group, a naphthylene group, a phenanthrenylene group, a fluorenyl group, or a pyrenylene group each substituted with at least one selected from a phenyl group, a naphthyl group, and an anthryl group.

In Formula 400 above, g, h, i, and j may be each independently 0, 1, or 2.

In some embodiments, $Ar_{113}$ to $Ar_{116}$ in Formula 400 may be each independently selected from a $C_1$-$C_{10}$ alkyl group substituted with at least one selected from a phenyl group, a naphthyl group, and an anthryl group; a phenyl group; a naphthyl group; an anthryl group; a pyrenyl group; a phenanthrenyl group; a fluorenyl group; a phenyl group, a naphthyl group, an anthryl group, a pyrenyl group, a phenanthrenyl group, and a fluorenyl group that are substituted with at least one selected from a deuterium atom, a halogen atom, a hydroxyl group, a cyano group, a nitro group, an amino group, an amidino group, hydrazine, hydrazone, a carboxyl group or a salt thereof, a sulfonic acid group or a salt thereof, a phosphoric acid or a salt thereof, a $C_1$-$C_{60}$ alkyl group, a $C_2$-$C_{60}$ group, a $C_2$-$C_{60}$ alkynyl group, a $C_1$-$C_{60}$ alkoxy group, a phenyl group, a naphthyl group, an anthryl group, a pyrenyl group, a phenanthrenyl group, a fluorenyl group, and

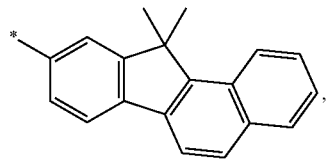 [SMILES: *c1ccc2c(c1)C(C)(C)c1c-2ccc2ccccc12]

but are not limited thereto.

For example, the anthracene-based compound of Formula 400 above may be one of the compounds represented by the following formulae, but is not limited thereto:

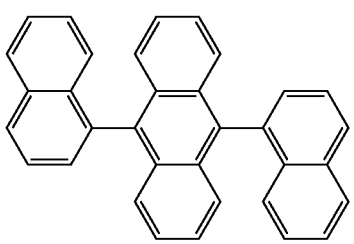

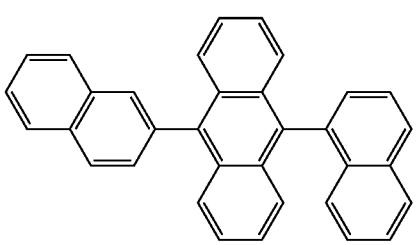

57
-continued
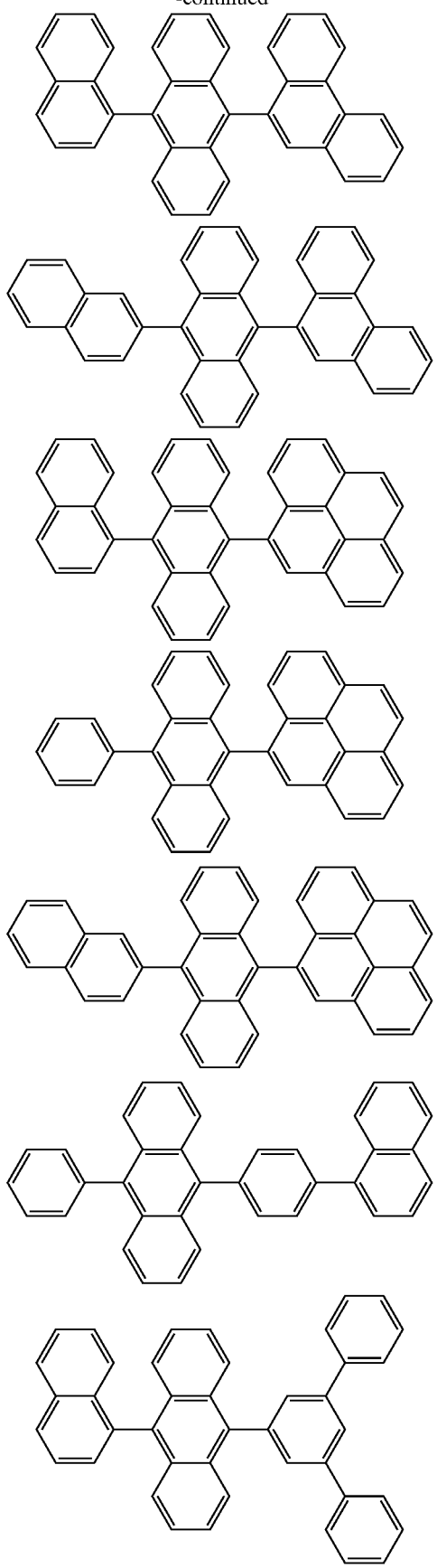
58
-continued
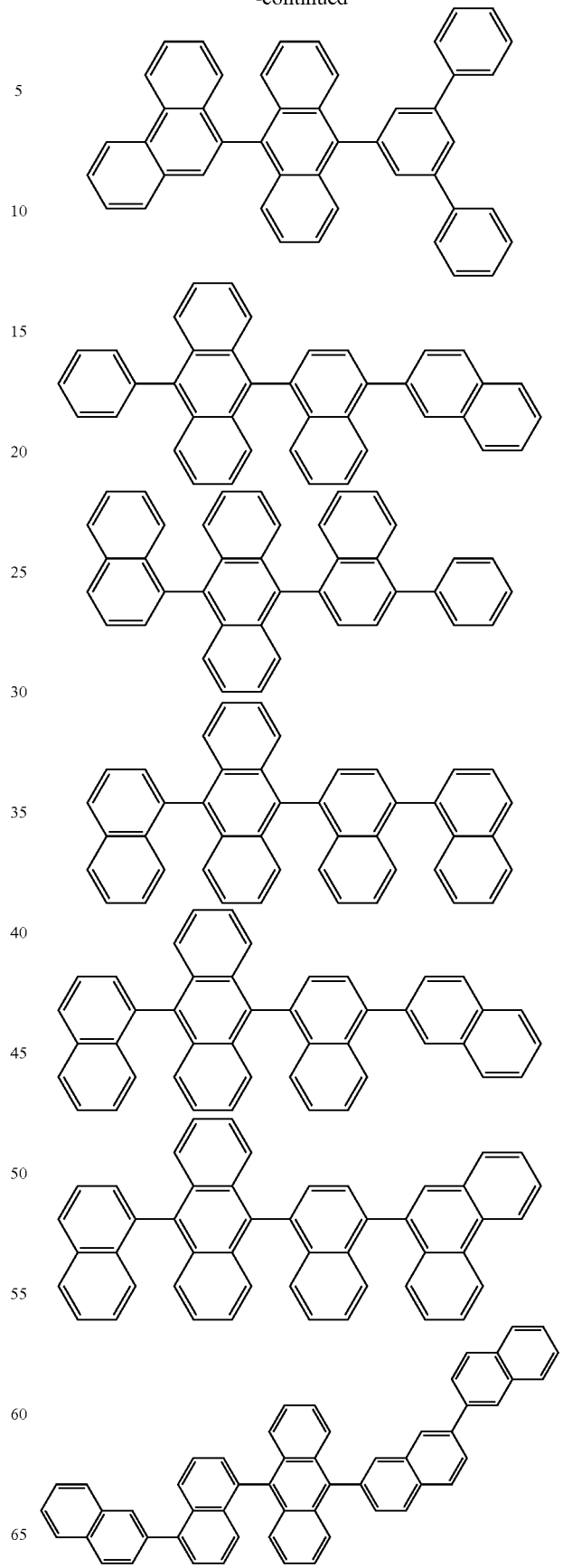

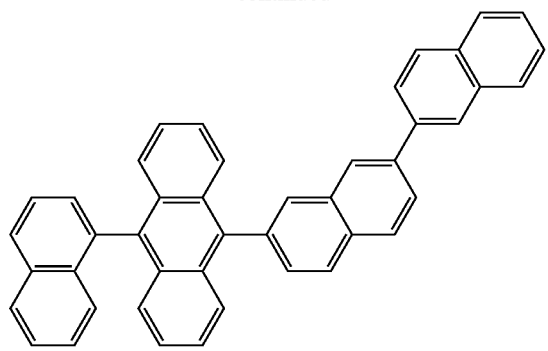
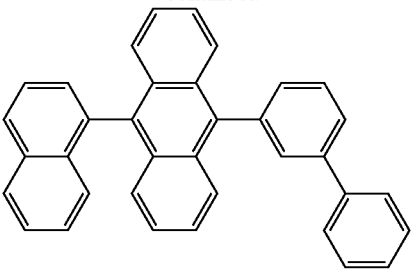
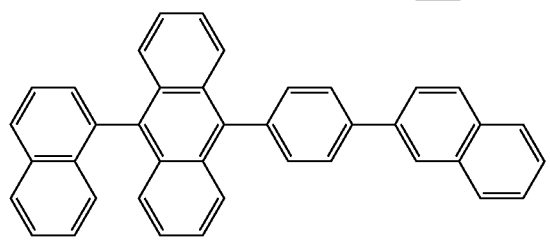
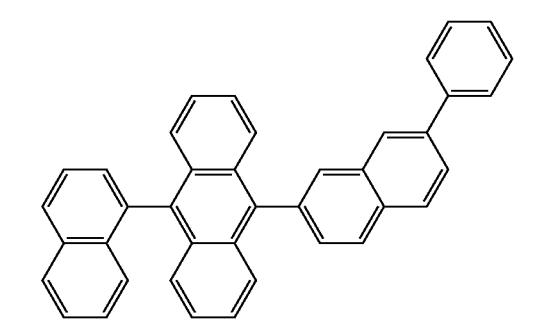
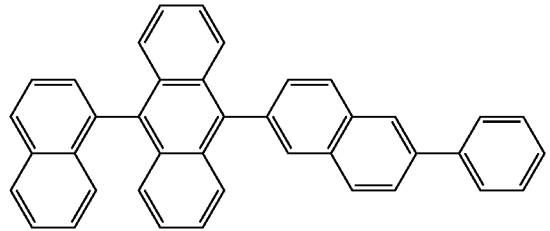
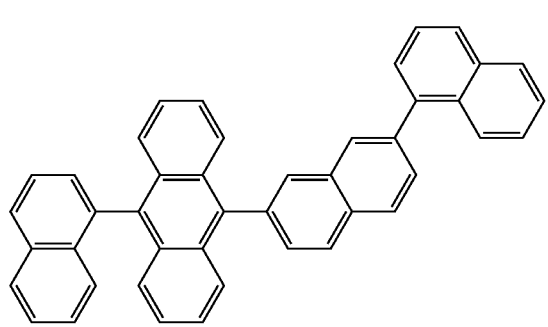
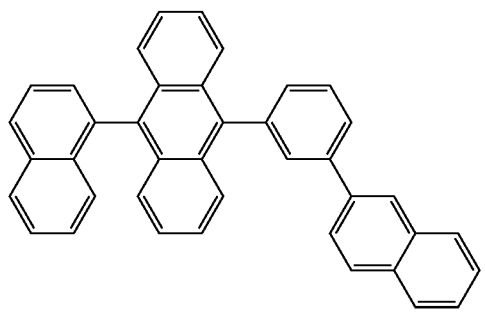
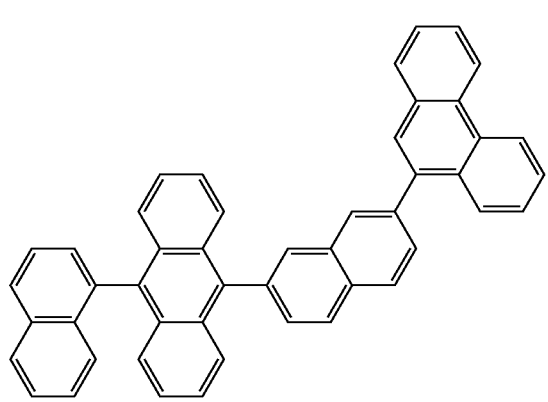
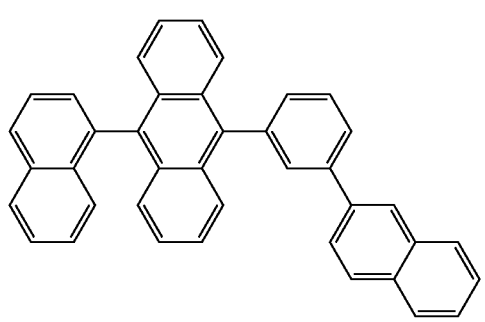
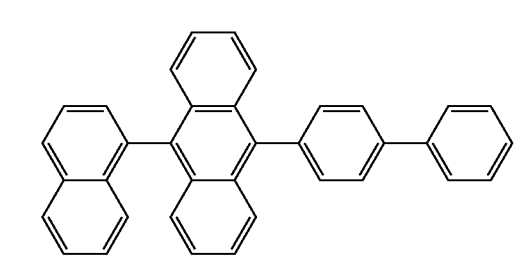
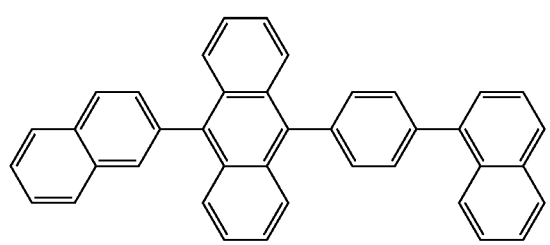

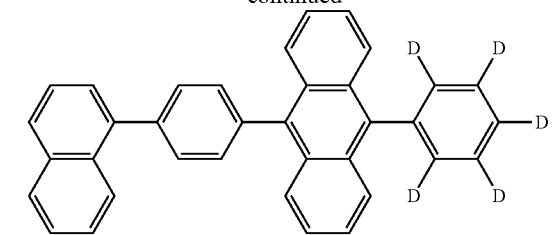
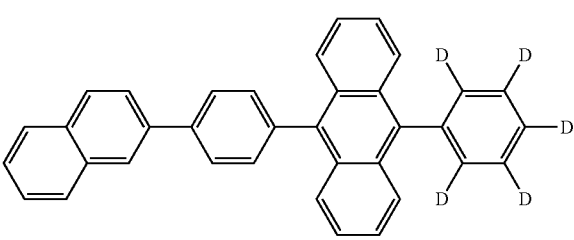
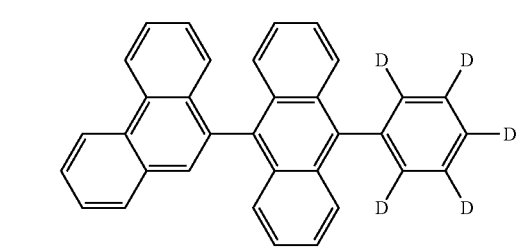
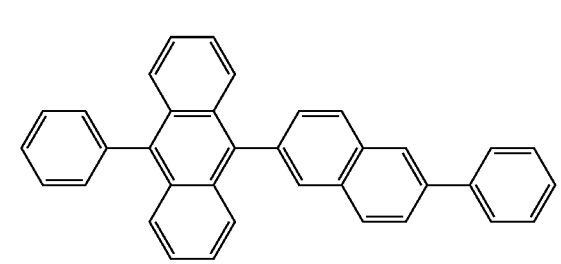
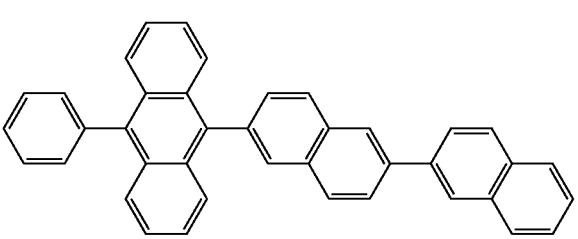
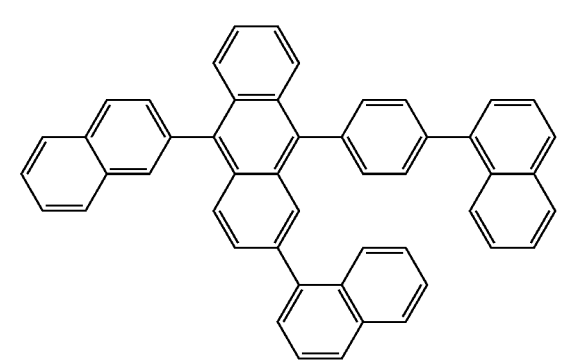
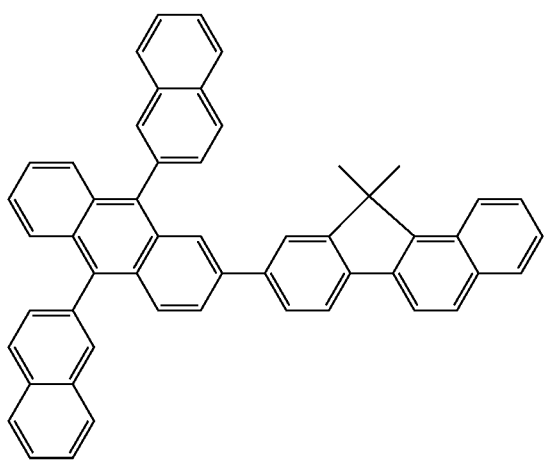
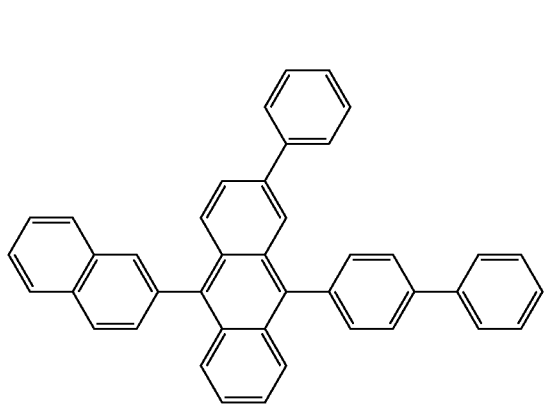
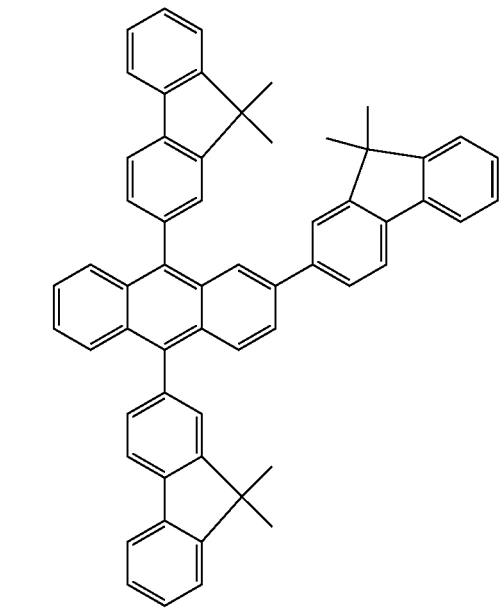

-continued

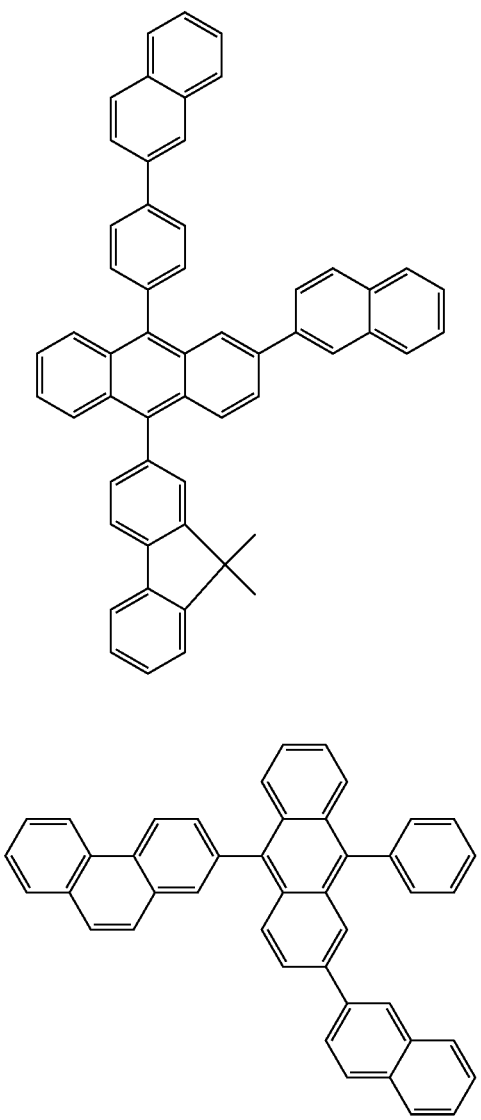

In some embodiments, an anthracene-based compound represented by Formula 401 below may be used as the host.

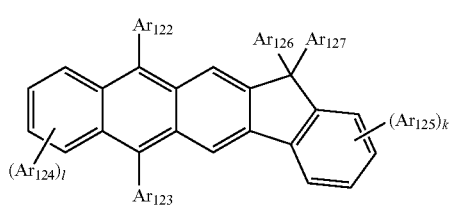

Formula 401

In Formula 401, $Ar_{122}$ to $Ar_{125}$ may be defined as described above in conjunction with $Ar_{113}$ of Formula 400, and thus detailed descriptions thereof will not be provided here.

In Formula 401, $Ar_{126}$ and $Ar_{127}$ may be each independently a $C_1$-$C_{10}$ alkyl group, for example, a methyl group, an ethyl group, or a propyl group.

In Formula 401, k and l may be each independently an integer from 0 to 4, for example, 0, 1, or 2.

In some embodiments, the anthracene compound of Formula 401 above may be one of the compounds represented by the following formulae, but is not limited thereto:

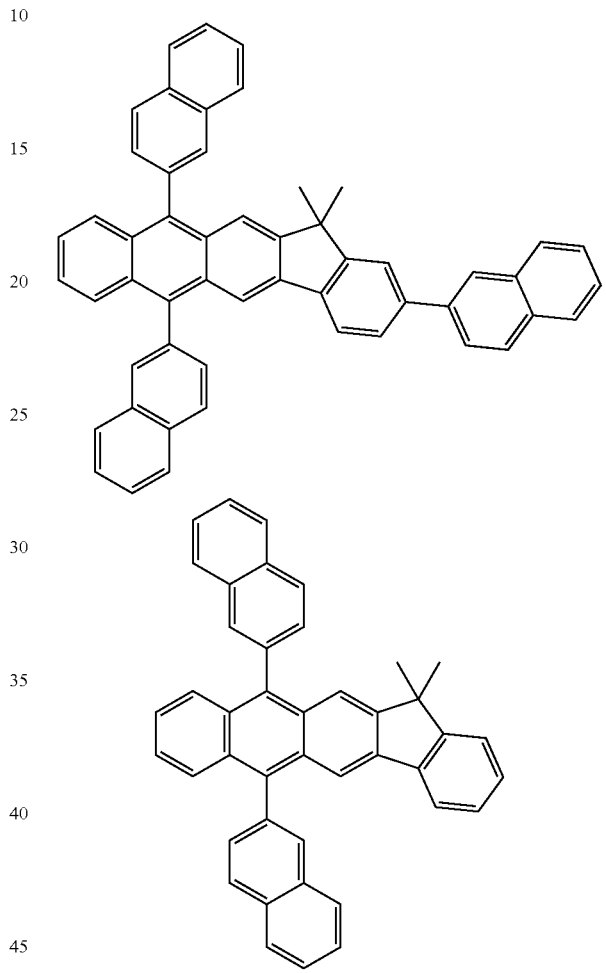

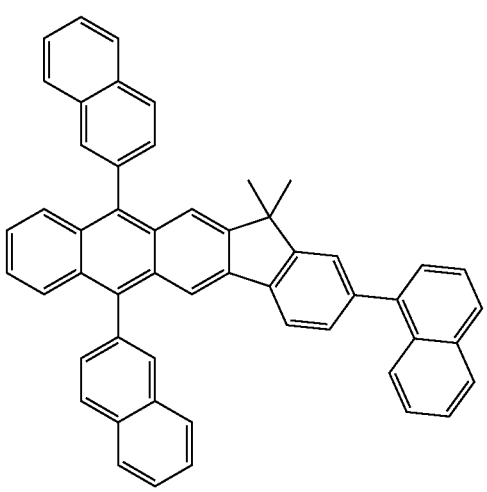

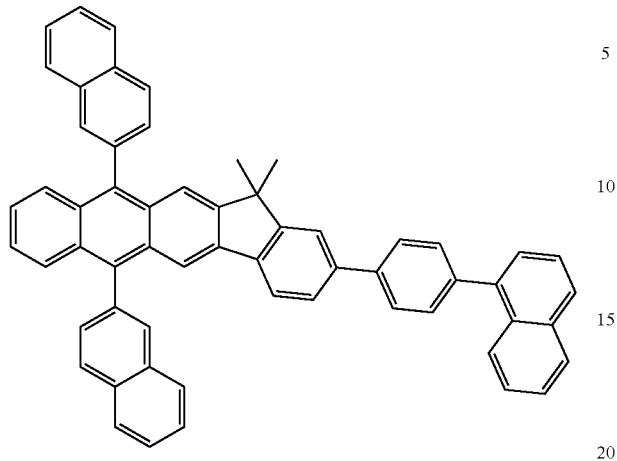

When the organic light-emitting device is a full-color organic light-emitting device, the emission layer may be patterned into a red emission layer, a green emission layer, and a blue emission layer.

At least one of the red EML, the green EML, and the blue EML may include a dopant.

Non-limiting examples of the blue dopant are compounds represented by the following formulae (ppy=phenylpyridine).

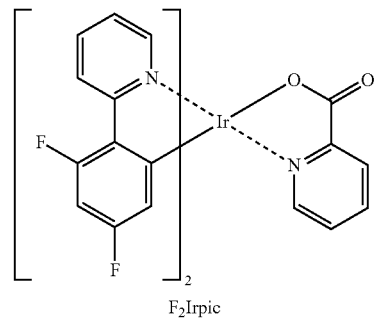

F₂Irpic

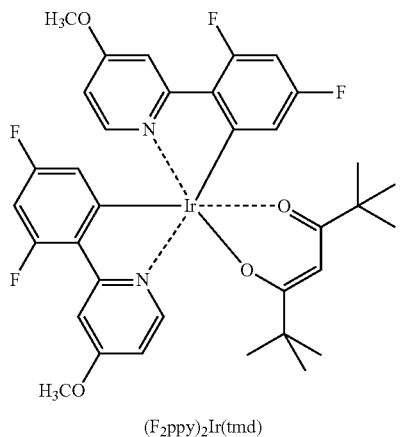

(F₂ppy)₂Ir(tmd)

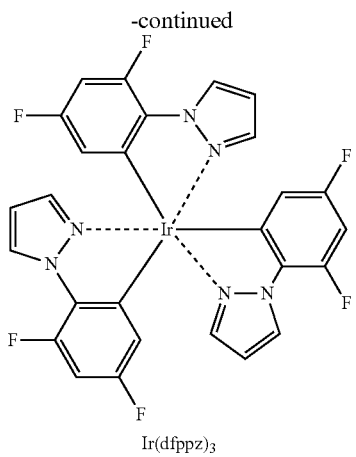

Ir(dfppz)₃

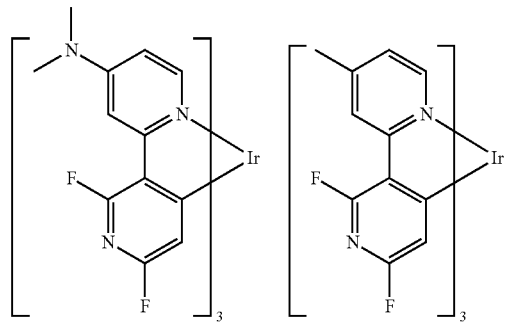

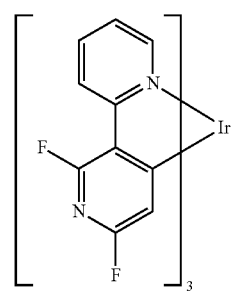

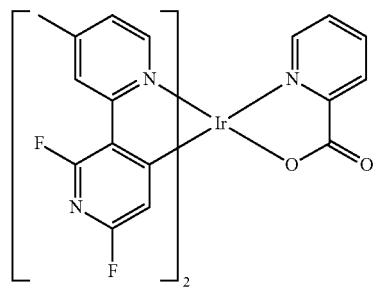

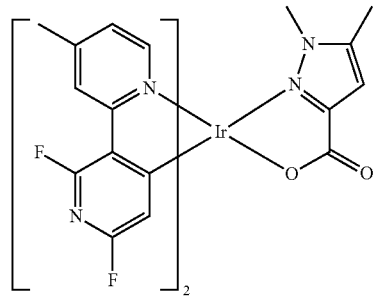

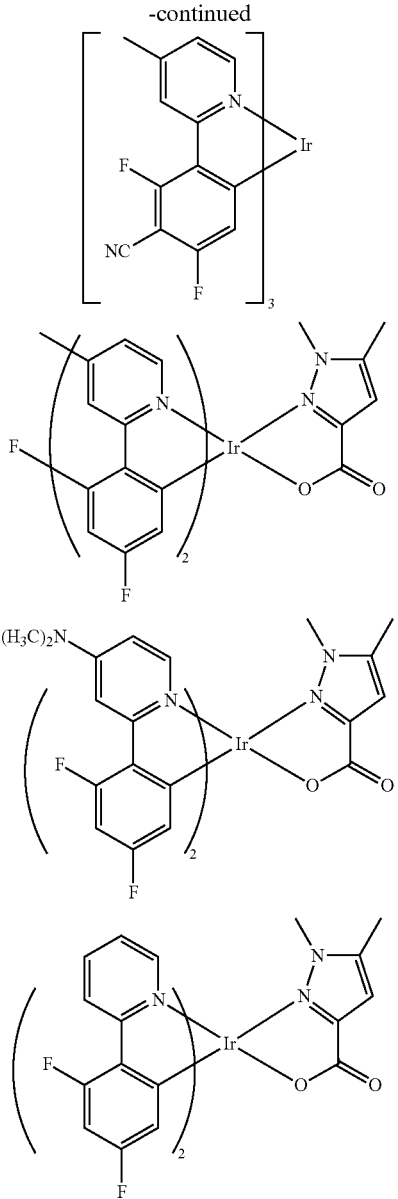
DPVBi
DPAVBi
Non-limiting examples of the red dopant are compounds represented by the following formulae.
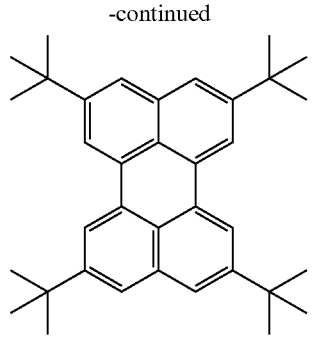
PtOEP
Ir(piq)$_3$    Btp$_2$Ir(acac)
Ir(pq)$_2$(acac)    Ir(2-phq)$_3$ -continued
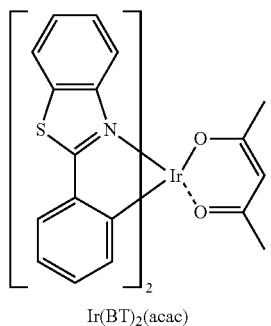
Ir(BT)₂(acac)
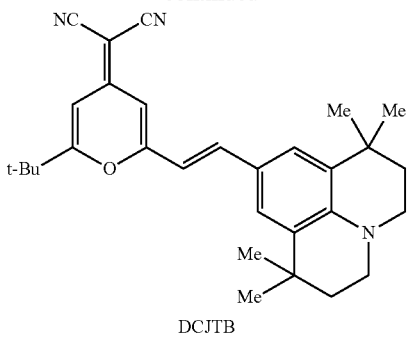
DCJTB
Non-limiting examples of the green dopant are compounds represented by the following formulae.
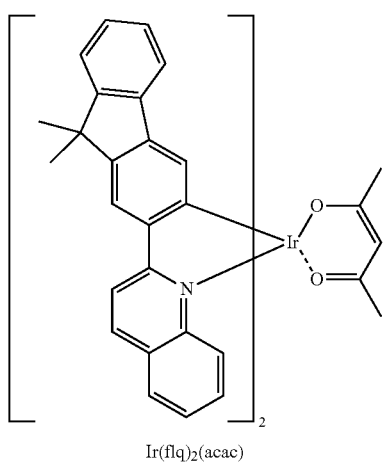
Ir(flq)₂(acac)
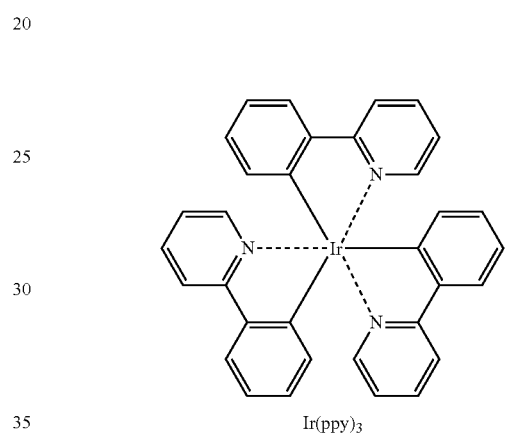
Ir(ppy)₃
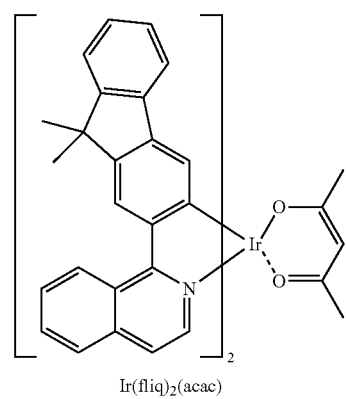
Ir(fliq)₂(acac)
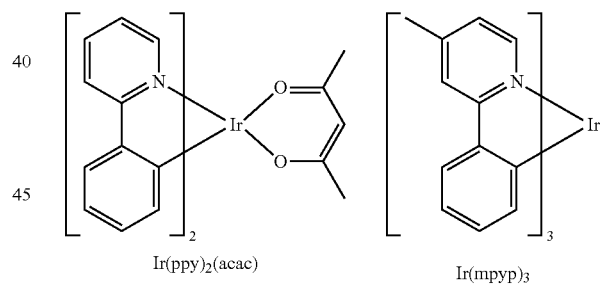
Ir(ppy)₂(acac)    Ir(mpyp)₃
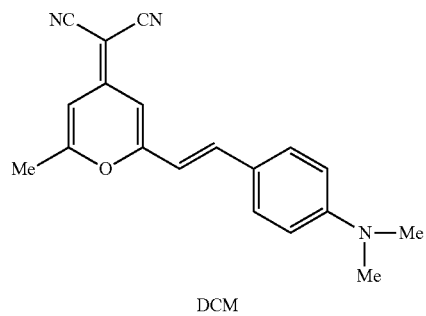
DCM
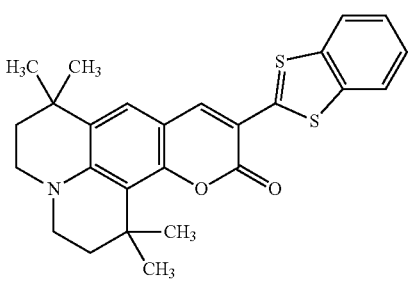
C545T
Non-limiting examples of the dopant that may be used in the EML are Pd complexes or Pt complexes represented by the compounds D1-D50.

71
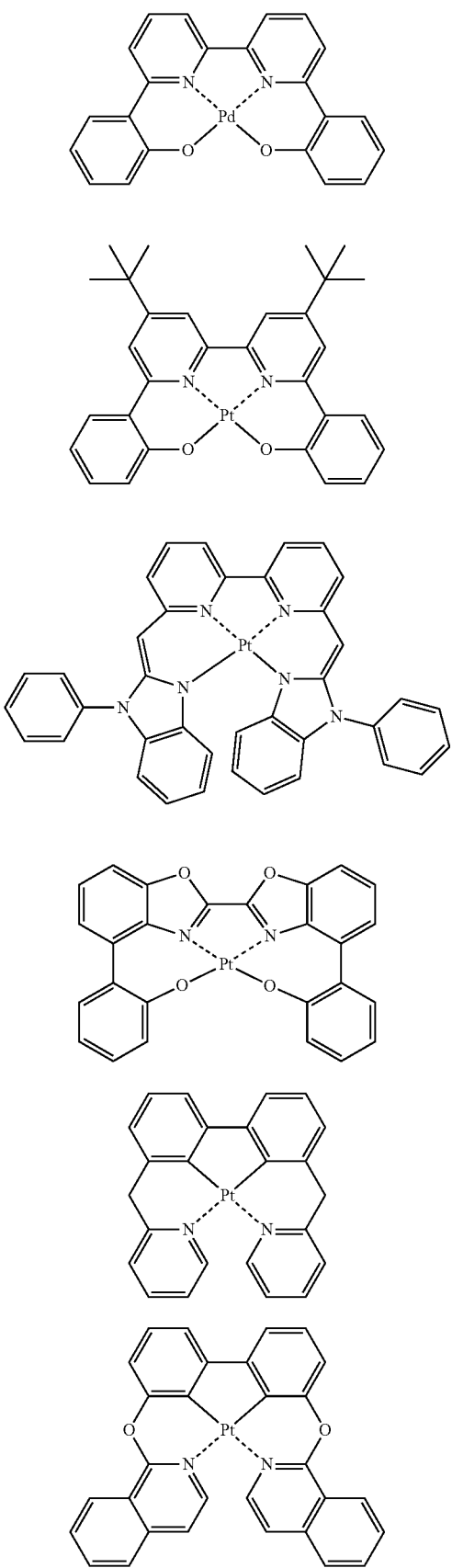
D1
D2
D3
D4
D5
D6
72
-continued
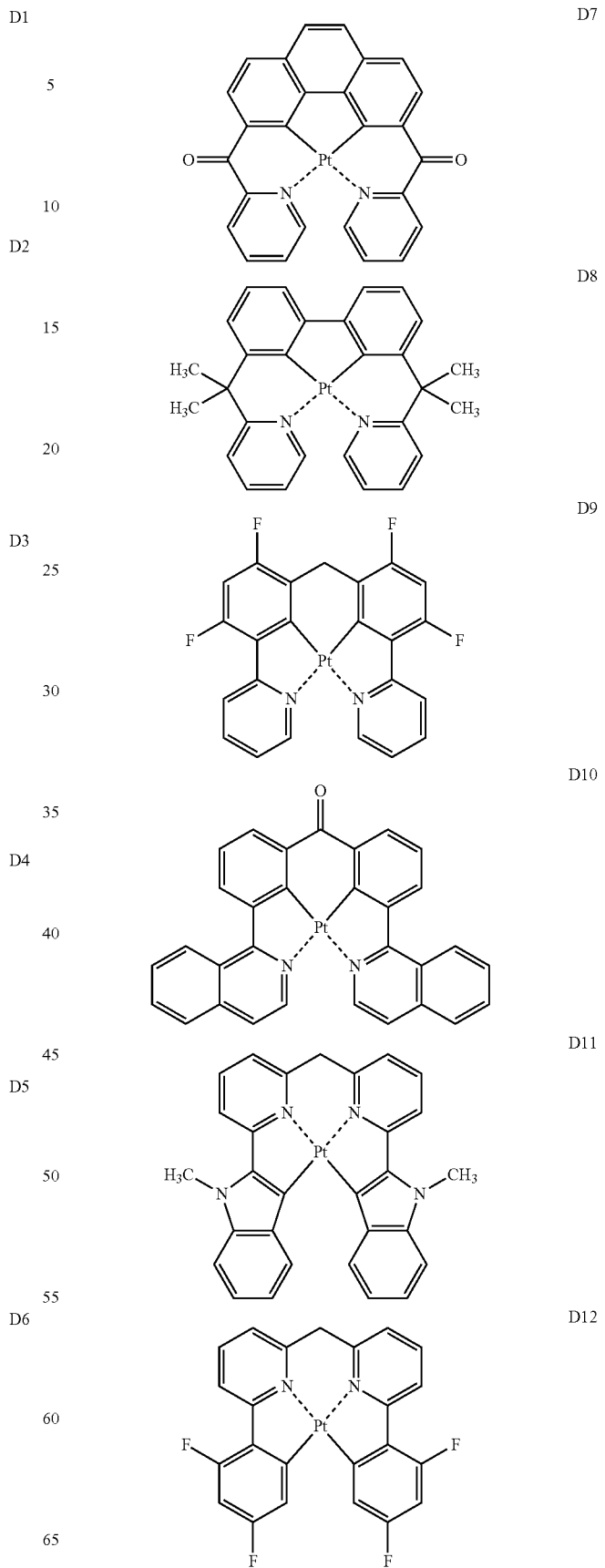
D7
D8
D9
D10
D11
D12

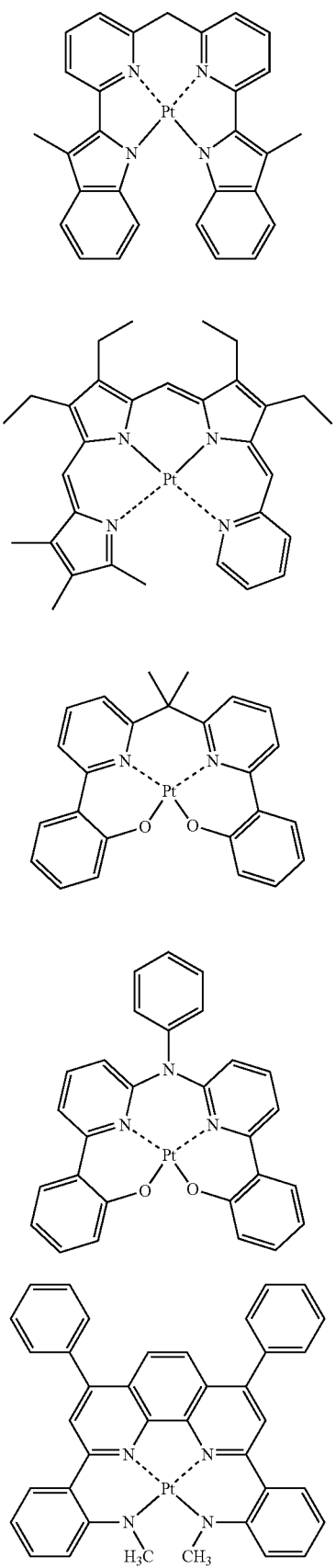
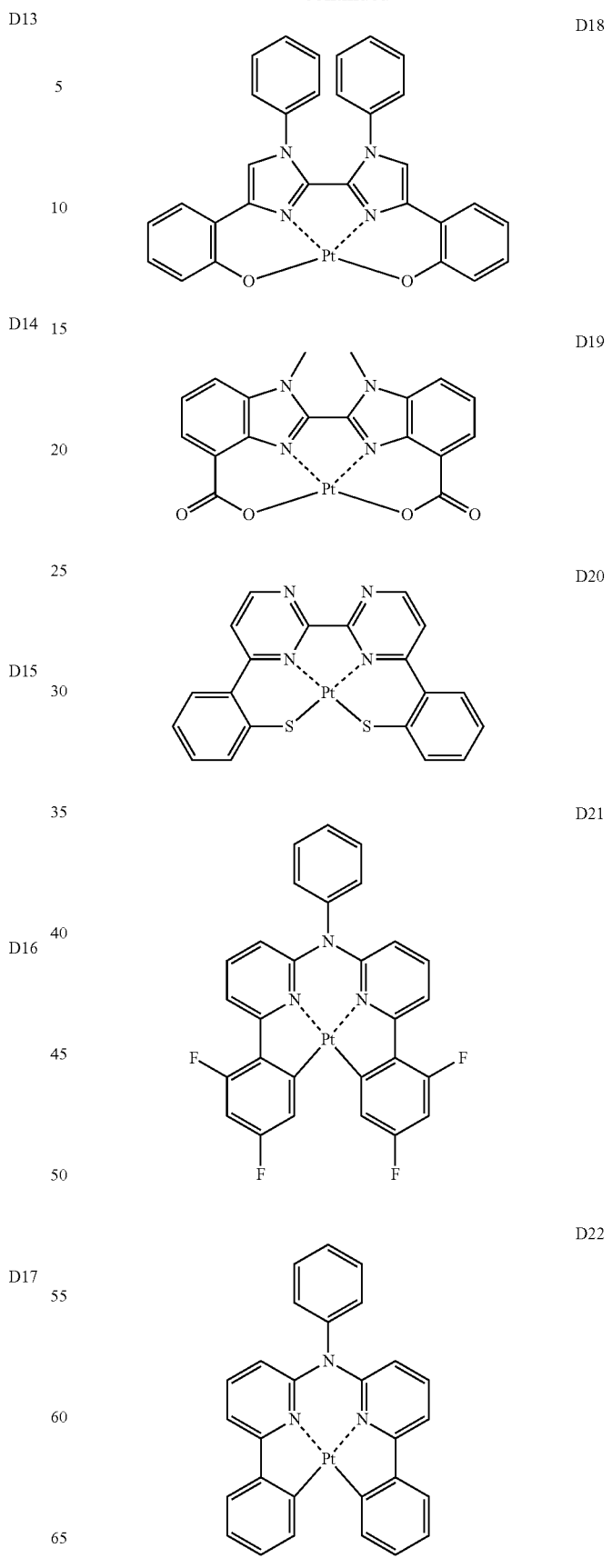

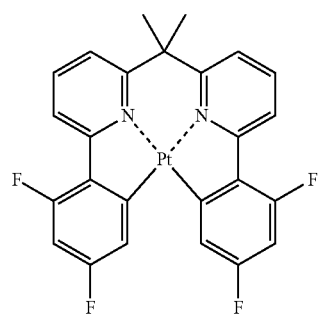
D23
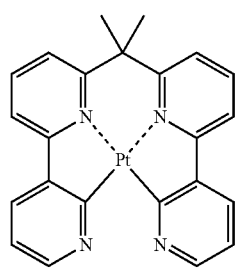
D24
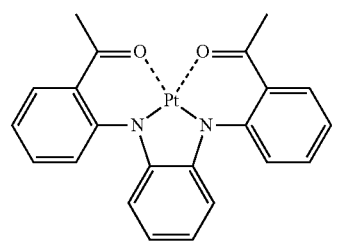
D25
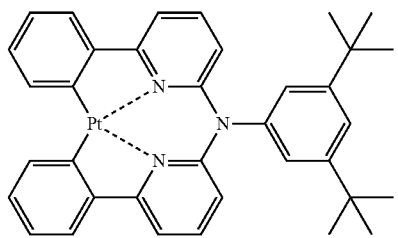
D26
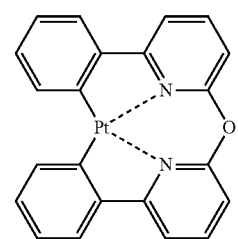
D27
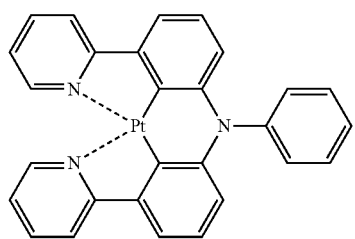
D28
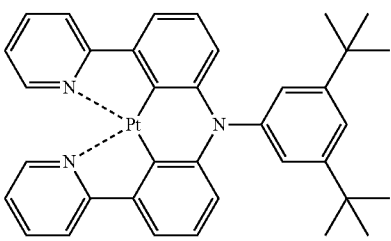
D29
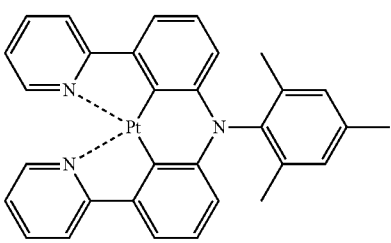
D30
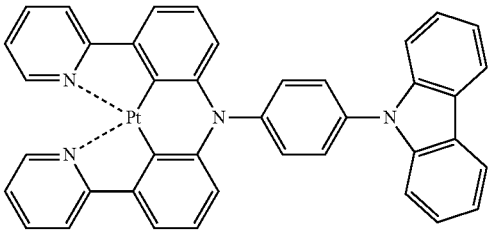
D31
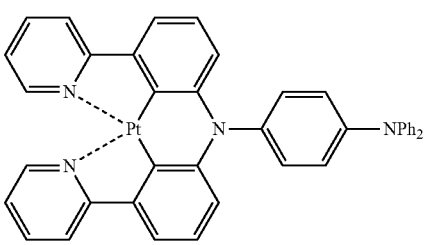
D32
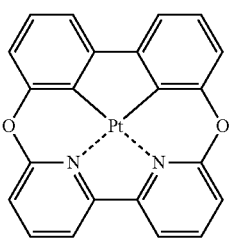
D33
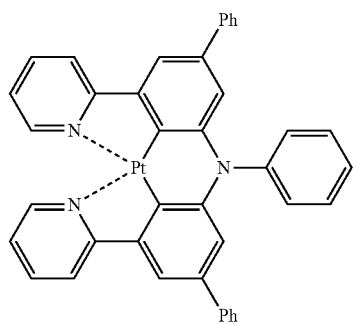
D34

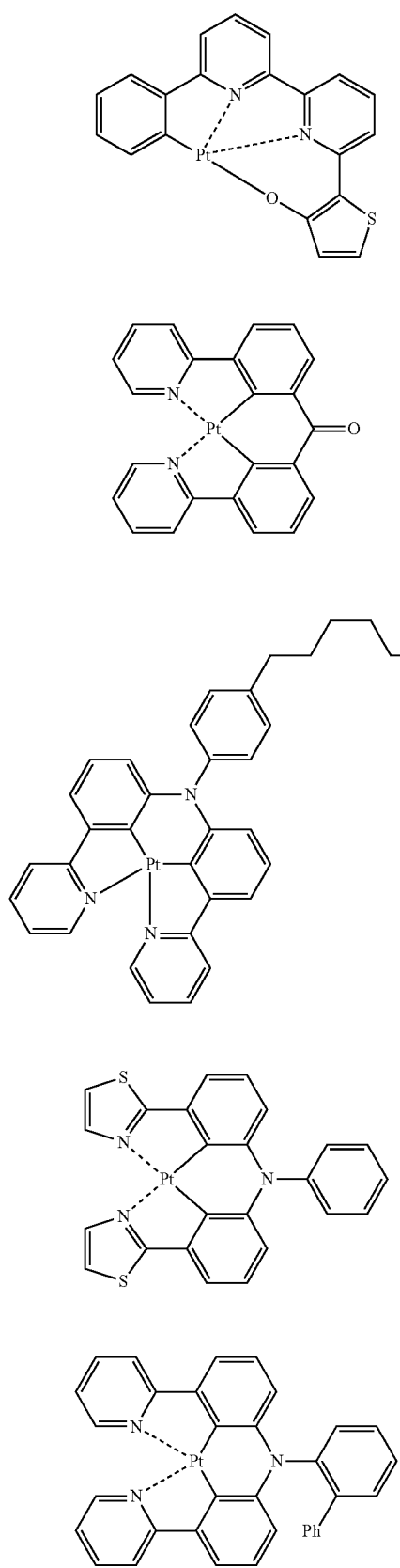
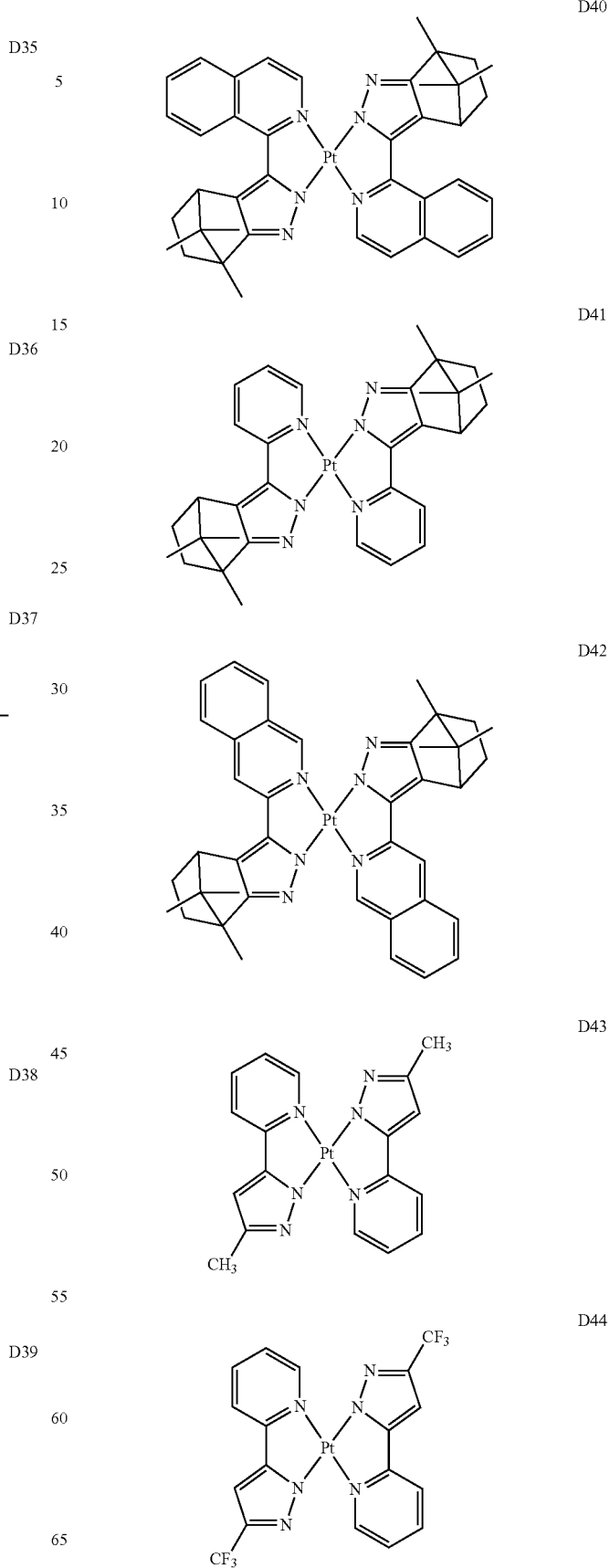

-continued
D45
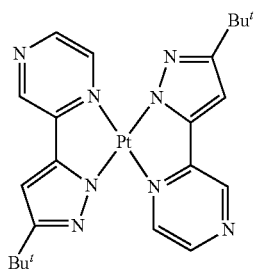
D46
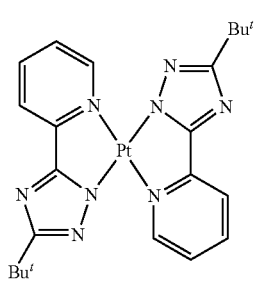
D47
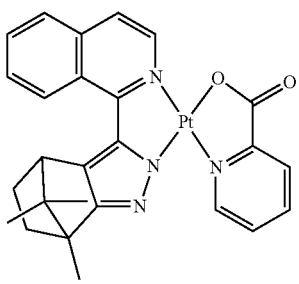
D48
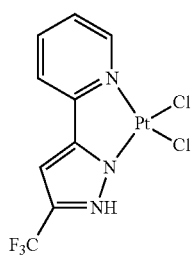
D49
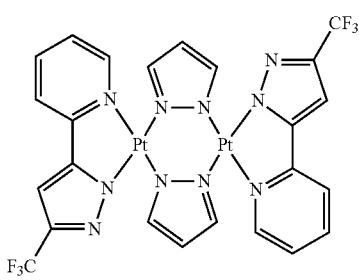
-continued
D50
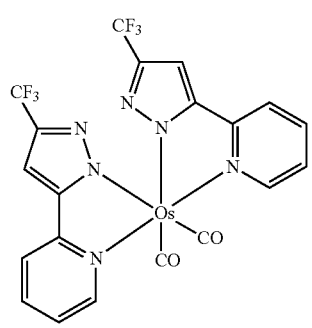
Non-limiting examples of the dopant that may be used in the EML are Os-complexes represented by the following formulae.
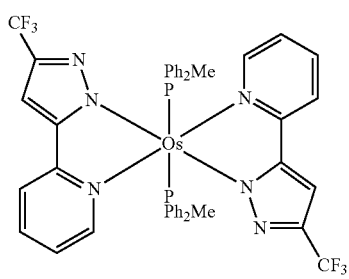
Os(fppz)$_2$(CO)$_2$
Os(fppz)$_2$(PPh$_2$Me)$_2$
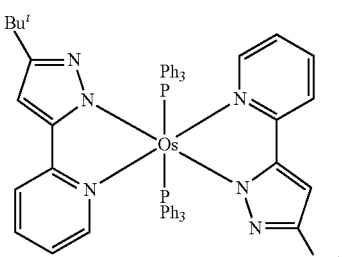
Os(bppz)$_2$(PPh$_3$)$_2$

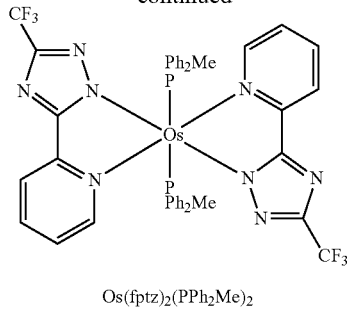

Os(fptz)₂(PPh₂Me)₂

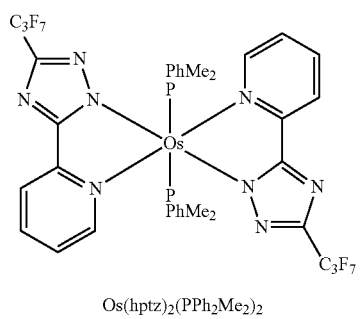

Os(hptz)₂(PPh₂Me₂)₂

When the EML includes both a host and a dopant, the amount of the dopant may be from about 0.01 to about 15 parts by weight based on 100 parts by weight of the host. However, the amount of the dopant is not limited to this range.

The thickness of the EML may be from about 100 Å to about 1,000 Å, and in some embodiments, may be from about 200 Å to about 600 Å. When the thickness of the EML is within these ranges, the EML may have good light emitting ability without a substantial increase in driving voltage.

An ETL may be formed on the EML by vacuum deposition, spin coating, casting, or the like. When the ETL is formed using vacuum deposition or spin coating, the deposition and coating conditions may be similar to those for the formation of the HIL, though the deposition and coating conditions may vary according to a compound that is used to form the ETL.

A material for forming the ETL may be the compound of Formula 1 above or any material capable of stably transporting electrons injected from an electron injecting electrode (cathode).

Non-limiting examples of the materials for forming the ETL are a quinoline derivative, such as tris(8-quinolinorate) aluminum (Alq₃), TAZ, BAlq, beryllium bis(benzoquinolin-10-olate) (Bebq₂), 9,10-di(naphthalene-2-yl)anthracene (ADN), Compound 201, and Compound 202.

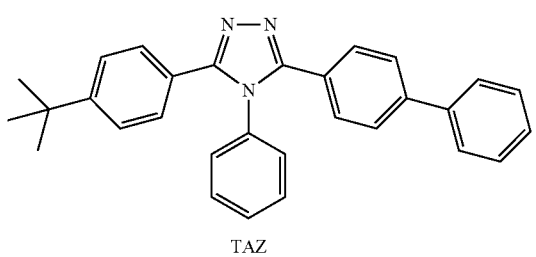

TAZ

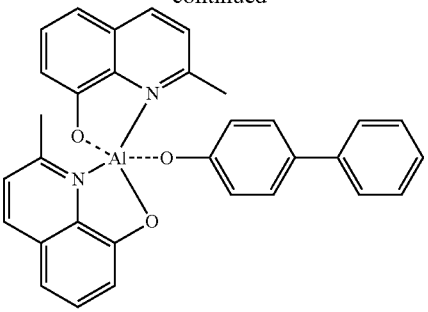

BAlq

<Compound 201>

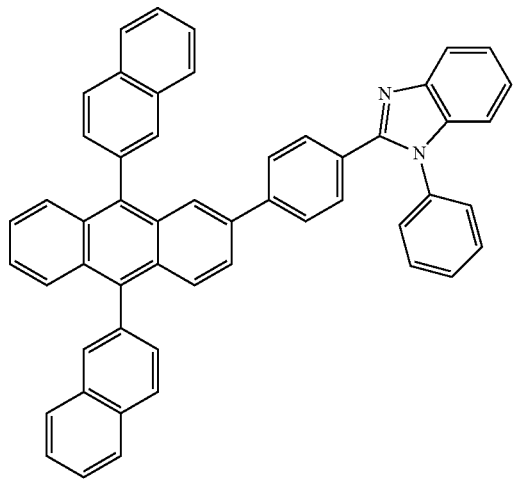

<Compound 202>

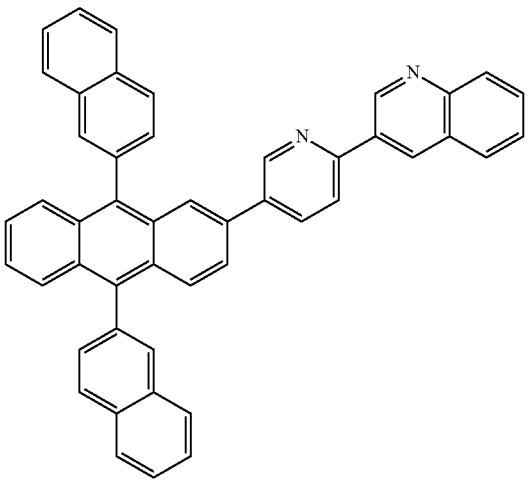

The thickness of the ETL may be from about 100 Å to about 1,000 Å, and in some embodiments, may be from about 150 Å to about 500 Å. When the thickness of the ETL is within these ranges, the ETL may have good electron transporting ability without a substantial increase in driving voltage.

In some embodiments the ETL may include an electron-transporting organic compound and a metal-containing material.

The metal-containing material may include a lithium (Li) complex. Non-limiting examples of the Li complex are lithium quinolate (LiQ) and Compound 203 below:

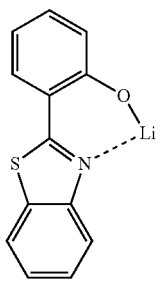

Compound 203

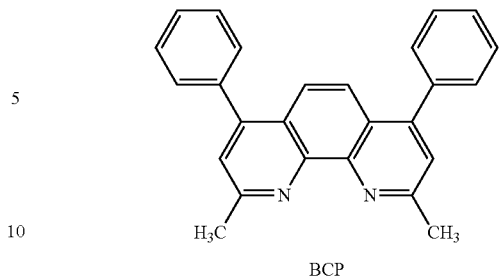

BCP

An EIL, which in some embodiments facilitates injection of electrons from the cathode, may be formed on the ETL. Any electron-injecting material suitable for use in organic light-emitting devices may be used to form the EIL.

Non-limiting examples of materials for forming the EIL are LiF, NaCl, CsF, $Li_2O$, and BaO. The deposition and coating conditions for forming the EIL may be similar to those for the formation of the HIL, though the deposition and coating conditions may vary according to the material that is used to form the EIL.

The thickness of the EIL may be from about 1 Å to about 100 Å, and in some embodiments, may be from about 3 Å to about 90 Å. When the thickness of the EIL is within these ranges, the EIL may have satisfactory electron injection ability without a substantial increase in driving voltage.

Finally, the second electrode is positioned on the organic layer. In some embodiments, the second electrode is a cathode that is an electron injection electrode. A material for forming the second electrode may be a metal, an alloy, an electro-conductive compound, which have a low work function, or a mixture thereof. In this regard, the second electrode may be formed of lithium (Li), magnesium (Mg), aluminum (Al), aluminum (Al)-lithium (Li), calcium (Ca), magnesium (Mg)-indium (In), magnesium (Mg)-silver (Ag), or the like, and may be formed as a thin film type transmission electrode. In some embodiments, to manufacture a top-emission light-emitting device, the transmission electrode may be formed of indium tin oxide (ITO) or indium zinc oxide (IZO).

Although the organic light-emitting device of the drawing is described above, the present invention is not limited thereto.

When a phosphorescent dopant is used in the EML, a hole blocking layer (HBL) may be formed between the ETL and the EML, or between the E-functional layer and the EML, by using vacuum deposition, spin coating, casting, Langmuir-Blodgett (LB) deposition, or the like, in order to prevent diffusion of triplet excitons or holes into the ETL. When the HBL is formed using vacuum deposition or spin coating, the conditions for deposition and coating may be similar to those for the formation of the HIL, although the conditions for deposition and coating may vary according to the material that is used to form the HBL. Any hole-blocking material suitable for use in organic light-emitting devices may be used. Non-limiting examples of the hole-blocking materials are oxadiazole derivatives, triazole derivatives, and phenanthroline derivatives. For example, bathocuproine (BCP) represented by the following formula may be used as a material for forming the HBL.

The thickness of the HBL may be from about 20 Å to about 1000 Å, and in some embodiments, may be from about 30 Å to about 300 Å. When the thickness of the HBL is within these ranges, the HBL may have improved hole blocking ability without a substantial increase in driving voltage.

According to embodiments of the present invention, the organic light-emitting device may be included in various types of flat panel display devices, such as in a passive matrix organic light-emitting display device or in an active matrix organic light-emitting display device. In particular, when the organic light-emitting device is included in an active matrix organic light-emitting display device including a thin-film transistor, the first electrode on the substrate may function as a pixel electrode, electrically connected to a source electrode or a drain electrode of the thin-film transistor. Moreover, the organic light-emitting device may also be included in flat panel display devices having double-sided screens.

In some embodiments the organic layer of the organic light-emitting device may include the compound of Formula 1 and may be formed by using a deposition method or a wet method of coating a solution of the compound of Formula 1.

Hereinafter, the present invention will be described in detail with reference to the following synthesis examples and other examples. However, these examples are for illustrative purposes only and are not intended to limit the scope of the present invention.

EXAMPLES

Synthesis Example 1

Synthesis of Compound 1

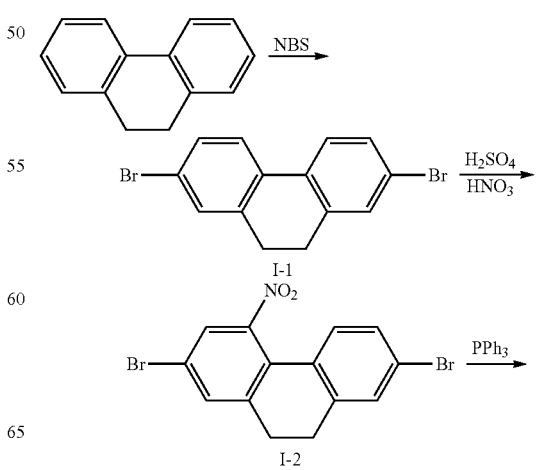

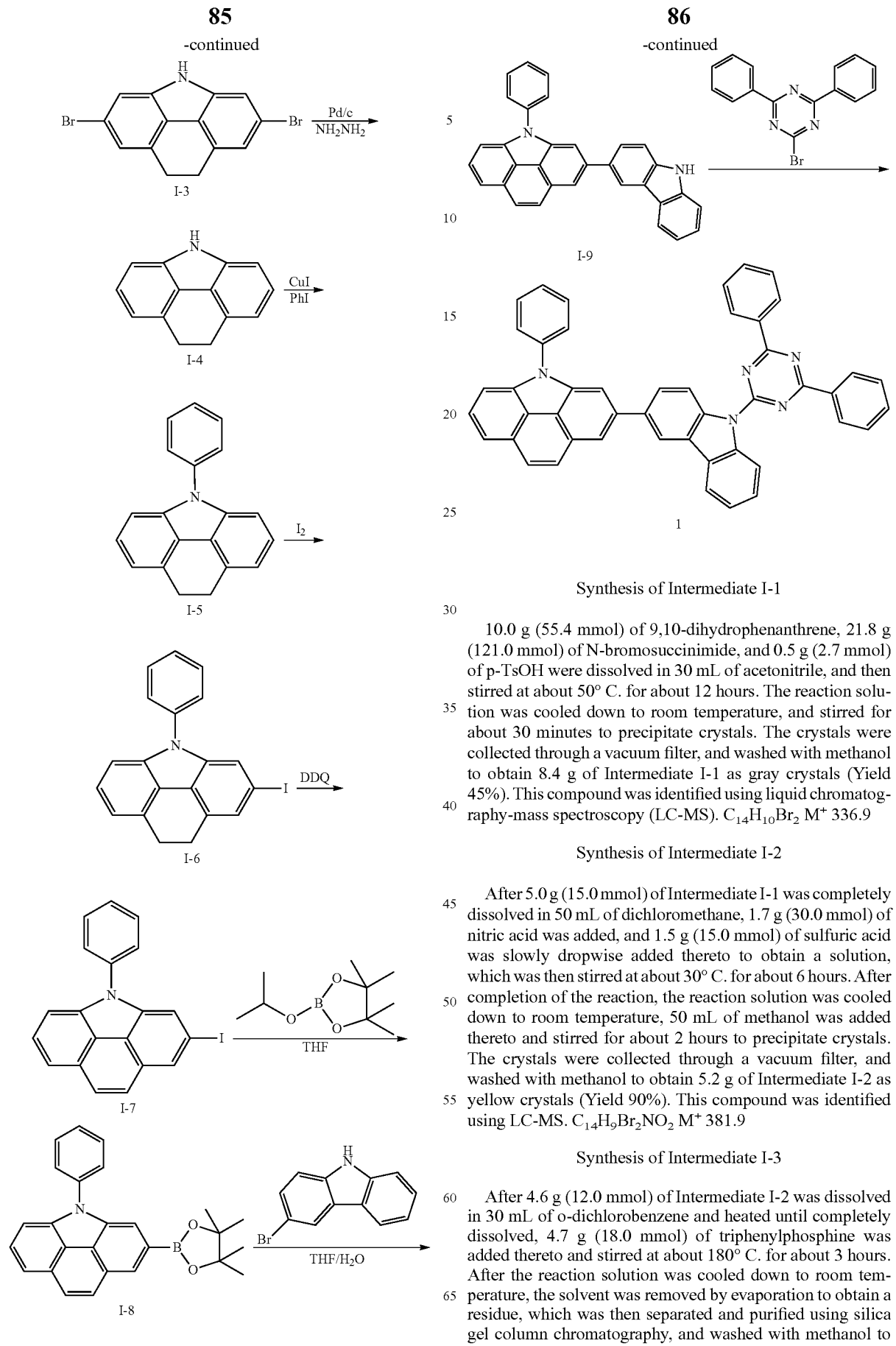

Synthesis of Intermediate I-1

10.0 g (55.4 mmol) of 9,10-dihydrophenanthrene, 21.8 g (121.0 mmol) of N-bromosuccinimide, and 0.5 g (2.7 mmol) of p-TsOH were dissolved in 30 mL of acetonitrile, and then stirred at about 50° C. for about 12 hours. The reaction solution was cooled down to room temperature, and stirred for about 30 minutes to precipitate crystals. The crystals were collected through a vacuum filter, and washed with methanol to obtain 8.4 g of Intermediate I-1 as gray crystals (Yield 45%). This compound was identified using liquid chromatography-mass spectroscopy (LC-MS). $C_{14}H_{10}Br_2$ $M^+$ 336.9

Synthesis of Intermediate I-2

After 5.0 g (15.0 mmol) of Intermediate I-1 was completely dissolved in 50 mL of dichloromethane, 1.7 g (30.0 mmol) of nitric acid was added, and 1.5 g (15.0 mmol) of sulfuric acid was slowly dropwise added thereto to obtain a solution, which was then stirred at about 30° C. for about 6 hours. After completion of the reaction, the reaction solution was cooled down to room temperature, 50 mL of methanol was added thereto and stirred for about 2 hours to precipitate crystals. The crystals were collected through a vacuum filter, and washed with methanol to obtain 5.2 g of Intermediate I-2 as yellow crystals (Yield 90%). This compound was identified using LC-MS. $C_{14}H_9Br_2NO_2$ $M^+$ 381.9

Synthesis of Intermediate I-3

After 4.6 g (12.0 mmol) of Intermediate I-2 was dissolved in 30 mL of o-dichlorobenzene and heated until completely dissolved, 4.7 g (18.0 mmol) of triphenylphosphine was added thereto and stirred at about 180° C. for about 3 hours. After the reaction solution was cooled down to room temperature, the solvent was removed by evaporation to obtain a residue, which was then separated and purified using silica gel column chromatography, and washed with methanol to obtain 2.9 g of Intermediate I-3 as white crystals (Yield: 70%). This compound was identified using LC-MS. $C_{14}H_9Br_2N$ M+ 349.9

Synthesis of Intermediate I-4

After 10 g (28.5 mmol) of Intermediate I-3 and 0.03 g (0.28 mmol) of Pd/C were dissolved in 100 mL of ethanol at room temperature, the temperature was increased to 50° C., and 5.48 g (171) mmol of hydrazine was dropwise added thereto and stirred for about 24 hours. The reaction solution was cooled down to room temperature, washed with acetone, and then added with 100 mL of ice water to obtain 3.63 g of Intermediate I-4 as white crystals (Yield: 66%). This compound was identified using LC-MS. $C_{14}H_{11}N$ M+ 194.1

Synthesis of Intermediate I-5

1.93 g (10.0 mmol) of Intermediate I-4, 2.5 g (12.0 mmol) of iodobenzene, 0.2 g (1.0 mmol) of 1,10-phenanthroline, 0.2 g (2.0 mmol) of CuI, and 4.1 g (30.0 mmol) of $K_2CO_3$ were dissolved in 30 mL of N,N-dimethylformamide (DMF) to obtain a solution, which was then stirred at about 80° C. for about 24 hours. The reaction solution was cooled down to room temperature, and then extracted three times with 30 mL of water and 40 mL of diethyl ether. The organic phase was collected and was dried using magnesium sulfate to evaporate the solvent. The residue was separated and purified using silica gel column chromatography to obtain 2.39 g of Intermediate I-5 (Yield: 89%). This compound was identified using LC-MS. $C_{20}H_{15}N$ M+ 270.1

Synthesis of Intermediate I-6

After 10 g (37.1 mmol) of Intermediate I-5 was completely dissolved in 100 mL of dichloromethane, 3.58 g (14.1 mmol) of iodine and 2.38 g (11.13 mmol) of $KIO_3$ were added over five times. After being stirred for about 6 hours, the reaction solution was washed with methanol to obtain 8.06 g of Intermediate I-6 (Yield 55%). This compound was identified using LC-MS. $C_{20}H_{14}IN$ M+ 396.1

Synthesis of Intermediate I-7

After 10 g (25.3 mmol) of Intermediate I-6 was dissolved in 100 mL of toluene in an oxygen atmosphere, 1.57 g (7.6 mmol) of 2,3-dichloro-5,6-dicyano-1,4-benzoquinone and 0.52 g (7.6 mmol) of $NaNO_2$ were added thereto. After being stirred at about 110° C. for about 6 hours and completion of the reaction, the reaction solution was cooled down to room temperature, and the solvent was evaporated. The residue was separated and purified using silica gel column chromatography to obtain 8.94 g of Intermediate I-7 (Yield: 90%). This compound was identified using LC-MS. $C_{20}H_{12}IN$ M+ 394.0

Synthesis of Intermediate I-8

10 g (25.3 mmol) of Intermediate I-7 was dissolved in 30 mL of THF and then 10 mL (25.0 mmol) of n-butyllithium (n-BuLi, 2.5M in hexane) was slowly dropwise added thereto at a temperature of −78° C. After the reaction solution was stirred at the same temperature for about 1 hour, 9.3 mL (50 mmol) of 2-isoproxy-4,4,5,5,-tetramethyl-1,3,2-dioxaborolane was slowly dropwise added into the reaction solution, which was then stirred at about −78° C. for about 1 hour, and further at room temperature for about 24 hours. After the reaction was completed, 50 mL of a 10% HCl aqueous solution and 50 mL of $H_2O$ were added, followed by three times of extraction with 80 mL of diethyl ether. The organic phase was collected and was dried using magnesium sulfate to evaporate the solvent. The residue was separated and purified using silica gel column chromatography to obtain 7.49 g of Intermediate I-8 (Yield: 75%). This compound was identified using LC-MS. $C_{26}H_{24}BNO_2$: M+ 394.2

Synthesis of Intermediate I-9

3.95 g (10 mmol) of Intermediate I-8, 2.46 g (10 mmol) of 3-bromo-9H-carbazole, 0.577 g (0.5 mmol) of tetrakis(triphenylphosphine)palladium $(Pd(PPh_3)_4)$, and 1.658 g (12 mmol) of $K_2CO_3$ were dissolved in 100 mL of a mixed solution of tetrahydrofuran (THF) and $H_2O$ (2:1 by volume), and then stirred at about 80° C. for about 5 hours. The reaction solution was cooled down to room temperature, and 40 mL of water was added thereto, followed by three times of extraction with 50 mL of ethyl ether. The organic phase was collected and was dried using magnesium sulfate to evaporate the solvent. The residue was separated and purified using silica gel column chromatography to obtain 3.34 g of Intermediate I-9 (Yield: 77%). This compound was identified using LC-MS. $C_{32}H_{20}N_2$: M+ 433.1

Synthesis of Compound 1

4.34 g (10.0 mmol) of Intermediate I-9, 4.68 g (15.0 mmol) of 2-bromo-4,6-diphenyl-[1,3,5]triazine, 0.19 g (1.0 mmol) of CuI, 0.05 g (0.2 mmol) of 18-Crown-6, and 4.15 g (30.0 mmol) of $K_2CO_3$ were dissolved in 30 mL of 1,3-dimethyl-3,4,5,6-tetrahydro-2(1H)-pyrimidinone (DMPU) to obtain a solution, which was then stirred at about 170° C. for about 12 hours. The reaction solution was cooled down to room temperature, and then extracted three times with 50 mL of water and 50 mL of dichloromethane. The organic phase was collected and was dried using magnesium sulfate to evaporate the solvent. The residue was separated and purified using silica gel column chromatography to obtain 4.79 g of Compound 1 (Yield: 72%). This compound was identified using mass spectroscopy/fast atom bombardment MS/FAB and $^1H$ NMR. $C_{48}H_{30}N_4$ cal. 663.24. found 664.24.

$^1H$ NMR (CDCl$_3$, 400 MHz) ☐☐ 8.93-8.91 (m, 1H), 8.78-8.75 (m, 4H), 8.62 (m, 1H), 8.46-8.44 (m, 1H), 8.36-8.33 (m, 2H), 8.18-8.15 (dd, 1H), 7.98-7.95 (m, 1H), 7.89-7.84 (m, 4H), 7.79-7.73 (m, 4H), 7.69-7.67 (m, 3H), 7.62-7.50 (m, 7H)

Synthesis Example 2

Synthesis of Compound 41

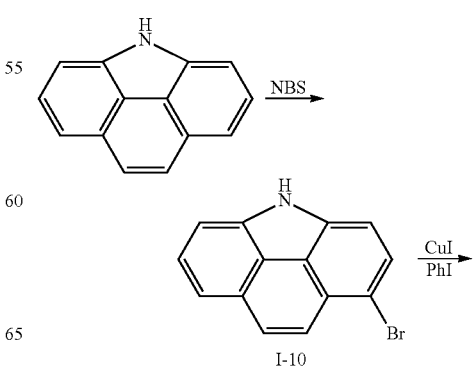

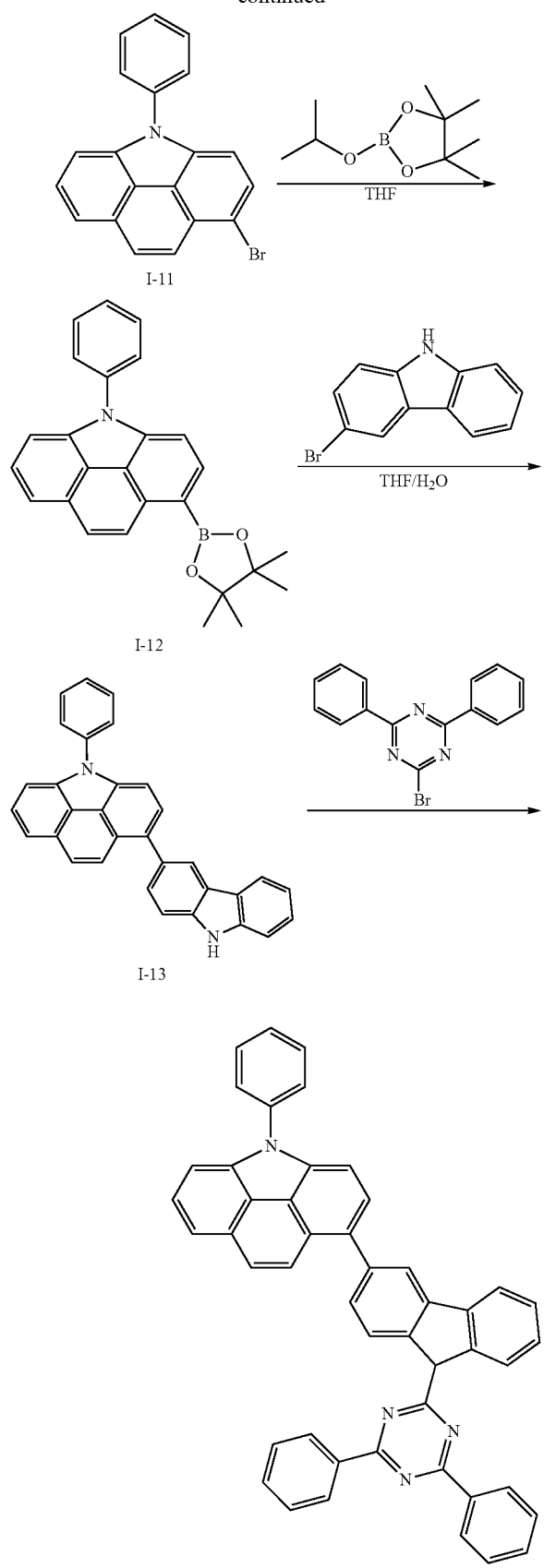

Synthesis of Intermediate I-10

After 1.91 g (10.0 mmol) of 6H-benzo[def]carbazole was completely dissolved in 60 mL of carbon tetrachloride (CCl$_4$), 1.78 g (10.0 mmol) of N-bromosuccinimide was added thereto to obtain a solution, which was then stirred at about 80° C. for about 30 minutes. The reaction solution was cooled down to room temperature, and stirred for about 30 minutes to precipitate crystals. The crystals were collected through a vacuum filter, and washed with methanol to obtain 1.1 g of Intermediate I-10 as gray crystals (Yield 45%). This compound was identified using LC-MS. C$_{14}$H$_8$BrN:M$^+$ 269.9

Synthesis of Intermediate I-11

Intermediate I-11 was synthesized in the same manner as in the synthesis of Intermediate I-5, except that Intermediate I-10 instead of Intermediate I-4 was used. This compound was identified using LC-MS. C$_{20}$H$_{12}$BrN:M$^+$ 346.0

Synthesis of Intermediate I-12

Intermediate I-12 was synthesized in the same manner as in the synthesis of Intermediate I-8, except that Intermediate I-11 instead of Intermediate I-7 was used. This compound was identified using LC-MS. C$_{26}$H$_{24}$BNO$_2$:M$^+$ 394.2

Synthesis of Intermediate I-13

Intermediate I-13 was synthesized in the same manner as in the synthesis of Intermediate I-9, except that Intermediate I-12 instead of Intermediate I-8 was used. This compound was identified using LC-MS. C$_{32}$H$_{22}$N$_2$:M$^+$ 435.1

Synthesis of Compound 41

Compound 41 was synthesized in the same manner as in the synthesis of Compound 1, except that Intermediate I-13 instead of Intermediate I-9 was used. This compound was identified using mass spectroscopy/fast atom bombardment (MS/FAB) and $^1$H nuclear magnetic resonance (NMR). C$_{48}$H$_{30}$N$_4$ cal. 663.24. found 664.24.
$^1$H NMR (CDCl$_3$, 400 MHz) δ=8.93-8.91 (m, 1H), 8.78-8.75 (m, 4H), 8.65 (m, 1H), 8.41-8.39 (m, 1H), 8.27-8.25 (m, 1H), 8.15-8.13 (dd, 1H), 7.95-7.93 (m, 2H), 7.89-7.67 (m, 12H), 7.79-7.73 (m, 4H), 7.69-7.67 (m, 3H), 7.62-7.50 (m, 6H)

Additional compounds were synthesized using appropriate intermediates (for example, a material with Br or B(OH)$_2$ on an appropriate position) via the same synthetic pathways and the same method as described above. Analysis data of these compounds by $^1$H NMR and MS/FAB are shown in Table 1 below.

It should be obvious to one of ordinary skill in the art that other compounds not shown in Table 1 may also be synthesized based on the above-described synthetic pathways and source materials.

TABLE 1

| Compound | $^1$H NMR (CDCl$_3$, 400 MHz) | MS/FAB found | calc. |
|---|---|---|---|
| 1 | δ = 8.93-8.91 (m, 1H), 8.78-8.75 (m, 4H), 8.62 (m, 1H), 8.46-8.44 (m, 1H), 8.36-8.33 (m, 2H), 8.18-8.15 (dd, 1H), 7.98-7.95 (m, 1H), 7.89-7.84 (m, 4H), 7.79-7.73 (m, 4H), 7.69-7.67 (m, 3H), 7.62-7.50 (m, 7H) | 664.24 | 663.24 |

TABLE 1-continued

| Compound | ¹H NMR (CDCl₃, 400 MHz) | MS/FAB found | MS/FAB calc. |
|---|---|---|---|
| 3 | δ = 8.93-8.90 (m, 1H), 8.77-8.75 (m, 4H), 8.62 (m, 1H), 8.46-8.44 (m, 1H), 8.36-8.33 (m, 2H), 8.18-8.16 (m, 1H), 7.99-7.96 (m, 5H), 7.89-7.85 (m, 4H), 7.80-7.68 (m, 10H), 7.64-7.51 (m, 8H) | 816.30 | 815.30 |
| 6 | δ = 8.93-8.91 (m, 1H), 8.78-8.75 (m, 4H), 8.62 (m, 1H), 8.46-8.44 (m, 1H), 8.36-8.33 (m, 2H), 8.18-8.15 (dd, 1H), 8.11-8.09 (m, 1H), 7.97-7.92 (m, 3H), 7.88-7.68 (m, 9H), 7.62-7.56 (m, 5H), 7.51-7.49 (m, 2H), 7.43-7.40 (dd, 1H) | 754.25 | 753.25 |
| 9 | δ = 8.93-8.90 (m, 1H), 8.78-8.75 (m, 4H), 8.62 (m, 1H), 8.46-8.44 (m, 1H), 8.37-8.33 (m, 2H), 8.20-8.15 (m, 2H), 8.06-7.97 (m, 2H), 7.88-7.85 (m, 6H), 7.80-7.76 (m, 3H), 7.70-7.53 (m, 7H), 7.47-7.38 (m, 2H) | 714.26 | 713.26 |
| 11 | δ = 8.93-8.91 (m, 1H), 8.70-8.68 (m, 2H), 8.57 (m, 1H), 8.41-8.39 (m, 1H), 8.35-8.33 (m, 2H), 8.31-8.24 (m, 4H), 8.12-8.10 (m, 3H), 7.93-7.90 (m, 1H), 7.82-7.45 (m, 18H) | 764.27 | 763.27 |
| 12 | δ = 8.93-8.91 (m, 1H), 8.70-8.68 (m, 2H), 8.57 (m, 1H), 8.41-8.24 (m, 7H), 8.12-8.10 (m, 3H), 7.92-7.91 (m, 1H), 7.82-7.44 (m, 22H) | 840.30 | 839.30 |
| 15 | δ = 8.93-8.91 (m, 1H), 8.78-8.75 (m, 4H), 8.57 (m, 1H), 8.41-8.39 (m, 1H), 8.32-8.28 (m, 2H), 8.21-8.19 (m, 1H), 8.13-8.10 (dd, 1H), 7.97-7.92 (m, 3H), 7.83-7.80 (m, 4H), 7.75-7.43 (m, 13H) | 770.23 | 769.23 |
| 20 | δ = 9.05-9.04 (m, 2H), 8.92-8.91 (m, 1H), 8.66-8.64 (dd, 2H), 8.57 (m, 1H), 8.41-8.39 (m, 1H), 8.30-8.26 (m, 4H), 8.13-8.09 (m, 2H), 8.00-7.80 (m, 1H), 7.92-7.91 (m, 1H), 7.82-7.46 (m, 14H) | 716.25 | 715.25 |
| 21 | δ = 9.02-9.01 (m, 1H), 8.62 (m, 1H), 8.46-8.44 (m, 5H), 8.35 (m, 1H), 8.27-8.25 (m, 1H), 8.17-8.13 (m, 2H), 7.97-7.95 (m, 1H), 7.80-7.46 (m, 18H) | 663.25 | 662.25 |
| 26 | δ = 9.03-9.01 (m, 1H), 8.67 (m, 1H), 8.51-8.49 (m, 5H), 8.40 (m, 1H), 8.32-8.30 (m, 1H), 8.23-8.14 (m, 3H), 8.03-7.97 (m, 3H), 7.88-7.73 (m, 9H), 7.67-7.61 (m, 3H), 7.56-7.54 (m, 4H), 7.48-7.45 (dd, 1H) | 753.26 | 752.26 |
| 27 | δ = 9.03-9.01 (m, 1H), 8.67 (m, 1H), 8.51-8.49 (m, 5H), 8.40 (m, 1H), 8.32-8.29 (m, 3H), 8.23 (dd, 1H), 8.18 (s, 1H), 8.10-8.08 (m, 1H), 8.02-8.01 (m, 1H), 7.95-7.93 (m, 1H), 7.85-7.52 (m, 16H) | 769.23 | 768.23 |
| 28 | δ = 9.02-9.01 (m, 1H), 8.67 (m, 1H), 8.47-8.44 (m, 5H), 8.5 (d, 1H), 8.27-8.25 (m, 1H), 8.18-8.13 (m, 2H), 7.98-7.92 (m, 3H), 7.81-7.68 (m, 10H), 7.62-7.47 (m, 9H), 7.43-7.39 (m, 1H) | 739.28 | 738.28 |
| 30 | δ = 9.03-9.01 (m, 1H), 8.67 (m, 1H), 8.46-8.44 (m, 5H), 8.35 (m, 1H), 8.27-8.25 (m, 1H), 8.18-8.13 (m, 3H), 8.05-8.03 (m, 1H), 7.97-7.96 (m, 1H), 7.87-7.59 (m, 14H), 7.52-7.47 (m, 4H) | 713.26 | 712.26 |
| 31 | δ = 9.03-9.01 (m, 1H), 8.67-8.62 (m, 3H), 8.46-8.44 (m, 1H), 8.35 (m, 1H), 8.28-8.25 (m, 4H), 8.17-8.09 (m, 5H), 7.98-7.50 (m, 19H) | 763.28 | 762.28 |
| 32 | δ = 9.03-9.01 (m, 1H), 8.67-8.63 (m, 3H), 8.46-8.44 (m, 1H), 8.35 (m, 1H), 8.28-8.25 (m, 4H), 8.18-8.09 (m, 5H), 7.97-7.67 (m, 16H), 7.62-7.49 (m, 7H) | 839.31 | 838.31 |
| 36 | δ = 9.03-9.01 (m, 1H), 8.81 (m, 2H), 8.62 (m, 1H), 8.52-8.44 (m, 3H), 8.35 (m, 1H), 8.28-8.24 (m, 3H), 8.17-8.07 (m, 7H), 7.98-7.92 (m, 3H), 7.82-7.68 (m, 9H), 7.62-7.56 (m, 3H), 7.51-7.49 (m, 2H), 7.43-7.40 (dd, 1H) | 853.29 | 852.29 |
| 39 | δ = 9.02-9.01 (m, 1H), 8.97 (s, 1H), 8.85-8.83 (m, 2H), 8.75-8.73 (m, 2H), 8.57 (m, 1H), 8.41-8.39 (m, 1H), 8.32 (m, 1H), 8.22-8.20 (m, 1H), 8.16-8.11 (m, 4H), 8.00-7.93 (m, 2H), 7.84-7.80 (m, 2H), 7.74-7.65 (m, 3H), 7.55-7.48 (m, 7H), 7.42-7.33 (m, 2H) | 715.25 | 714.25 |
| 41 | δ = 8.93-8.91 (m, 1H), 8.78-8.75 (m, 4H), 8.65 (m, 1H), 8.41-8.39 (m, 1H), 8.27-8.25 (m, 1H), 8.15-8.13 (dd, 1H), 7.95-7.93 (m, 2H), 7.89-7.67 (m, 12H), 7.62-7.50 (m, 6H) | 664.24 | 663.24 |
| 44 | δ = 8.93-8.91 (m, 1H), 8.78-8.75 (m, 4H), 8.55 (m, 1H), 8.32-8.29 (m, 1H), 8.17-8.15 (m, 1H), 8.05-8.01 (m, 2H), 7.89-7.84 (m, 5H), 7.79-7.58 (m, 15H), 7.54-7.49 (m, 5H), 7.44-7.42 (m, 2H) | 816.30 | 815.30 |
| 45 | δ = 8.93-8.91 (m, 1H), 7.78-8.75 (m, 4H), 8.60 (m, 1H), 8.36-8.34 (m, 1H), 8.22-8.20 (m, 1H), 8.09-8.04 (m, 3H), 7.96-7.88 (m, 3H), 7.83-7.61 (m, 10H), 7.57-7.45 (m, 6H), 7.26-7.22 (m, 1H) | 754.25 | 753.25 |
| 49 | δ = 8.92-8.91 (m, 1H), 8.78-8.75 (m, 4H), 8.60 (m, 1H), 8.36-8.34 (m, 1H), 8.22-8.19 (m, 3H), 8.10-8.08 (dd, 1H), 8.00-7.97 (m, 2H), 7.90-7.53 (m, 15H), 7.48-7.45 (m, 2H), 7.41-7.39 (dd, 1H) | 770.23 | 769.23 |
| 50 | δ = 8.93-8.90 (m, 1H), 8.78-8.75 (m, 4H), 8.60 (m, 1H), 8.36-8.34 (m, 1H), 8.22-8.20 (m, 1H), 8.10-8.08 (dd, 1H), 8.00-7.98 (ss, 1H), 7.89-7.88 (m, 3H), 7.84-7.63 (m, 11H), 7.57-7.46 (m, 8H), 7.37-7.33 (m, 1H) | 740.27 | 739.27 |
| 52 | δ = 8.93-8.91 (m, 1H), 8.69-8.68 (m, 2H), 8.55 (m, 1H), 8.31-8.28 (m, 3H), 8.22-8.15 (m, 3H), 8.11-8.03 (m, 4H), 7.96-7.93 (m, 1H), 7.87-7.84 (m, 2H), 7.79-7.66 (m, 9H), 7.59-7.39 (m, 8H), 7.31-7.28 (dd, 1H) | 814.29 | 813.29 |
| 53 | δ = 8.92-8.91 (m, 1H), 8.70-8.68 (m, 2H), 8.55 (m, 1H), 8.32-8.28 (m, 3H), 8.22-8.15 (m, 3H), 8.08-8.03 (m, 3H), 7.85-7.83 (m, 2H), 7.77-7.39 (m, 22H) | 840.30 | 839.30 |
| 55 | δ = 8.92-8.91 (m, 1H), 8.85 (m, 2H), 8.74-8.72 (m, 2H), 8.60 (m, 1H), 8.41-8.37 (m, 5H), 8.27-8.21 (m, 3H), 8.15-8.09 (m, 3H), 8.01-7.50 (m, 17H), 7.31-8.27 (m, 1H) | 854.28 | 853.28 |
| 56 | δ = 8.93-8.90 (m, 1H), 8.85 (m, 2H), 8.74-8.72 (m, 2H), 8.60 (m, 1H), 8.41-8.37 (m, 5H), 8.27-8.21 (m, 4H), 8.15-8.13 (dd, 1H), 8.02-7.48 (m, 19H) | 870.26 | 869.26 |
| 61 | δ = 9.03-9.00 (m, 1H), 8.70 (m, 1H), 8.46-8.39 (m, 5H), 8.22-8.20 (m, 1H), 8.15-8.13 (m, 2H), 7.86-7.83 (m, 2H), 7.72-7.59 (m, 12H), 7.62-7.46 (m, 6H) | 663.25 | 662.25 |
| 62 | δ = 9.02-9.00 (m, 1H), 8.70 (m, 1H), 8.46-8.39 (m, 5H), 8.22-8.21 (m, 2H), 8.15-8.13 (m, 2H), 8.06-8.03 (m, 1H), 7.97-7.88 (m, 3H), 7.82-7.47 (m, 16H), 7.41-7.38 (m, 1H) | 713.26 | 712.26 |
| 63 | δ = 9.03-9.01 (m, 1H), 8.70 (m, 1H), 8.46-8.39 (m, 5H), 8.22-8.20 (m, 1H), 8.15-8.13 (m, 2H), 7.96-7.93 (m, 2H), 7.83-7.67 (m, 14H), 7.62-7.57 (m, 4H), 7.49-7.46 (m, 4H) | 739.28 | 738.28 |
| 64 | δ = 9.03-9.01 (m, 1H), 8.70 (m, 1H), 8.47-8.39 (m, 5H), 8.22-8.20 (m, 1H), 8.15-8.11 (m, 3H), 8.00-7.93 (m, 5H), 7.80-7.69 (m, 15H), 7.64-7.58 (m, 3H), 7.54-7.47 (m, 4H) | 815.31 | 814.31 |
| 67 | δ = 9.02-9.00 (m, 1H), 8.70 (m, 1H), 8.46-8.39 (m, 5H), 8.22-8.20 (m, 1H), 8.15-8.12 (m, 3H), 8.05-8.03 (m, 2H), 7.95-7.93 (m, 1H) 7.86-7.60 (m, 14H), 7.54-7.47 (m, 4H) | 713.26 | 712.26 |
| 70 | δ = 9.03-9.01 (m, 1H), 8.70 (m, 1H), 8.47-8.39 (m, 5H), 8.22-8.20 (m, 1H), 8.15-8.13 (m, 2H), 8.05-8.03 (m, 1H), 7.95-7.93 (m, 3H), 7.84-7.68 (m, 11H), 7.62-7.47 (m, 8H), 7.42-7.38 (m, 1H) | 739.28 | 738.28 |

TABLE 1-continued

| Com-pound | $^1$H NMR (CDCl$_3$, 400 MHz) | MS/FAB found | calc. |
|---|---|---|---|
| 71 | δ = 9.02-9.00 (m, 1H), 8.70 (m, 1H), 8.60-8.58 (m, 2H), 8.41-8.39 (m, 1H), 8.28-8.26 (m, 3H), 8.20 (m, 1H), 8.15-8.08 (m, 5H), 7.96-7.68 (m, 16H), 7.62-7.50 (m, 4H) | 763.28 | 762.28 |
| 73 | δ = 9.03-9.01 (m, 1H), 8.70 (m, 1H), 8.60-8.57 (m, 2H), 8.41-8.39 (m, 1H), 8.28-8.26 (m, 3H), 8.22-8.20 (m, 1H), 8.15-8.08 (m, 5H), 7.96-7.67 (m, 18H), 7.62-7.49 (m, 6H) | 839.31 | 838.31 |
| 75 | δ = 9.02-9.00 (m, 1H), 8.72 (m, 2H), 8.65 (m, 1H), 8.52-8.50 (m, 2H), 8.41-8.39 (m, 1H), 8.28-8.20 (m, 3H), 8.16-8.07 (m, 8H), 8.01-7.93 (m, 3H), 7.85-7.74 (m, 9H), 7.68-7.50 (m, 5H), 7.31-7.27 (m, 1H) | 853.29 | 852.29 |
| 78 | δ = 9.02-9.01 (m, 1H), 8.81-8.80 (m, 2H), 8.65 (m, 1H), 8.41-8.39 (m, 1H), 8.28-8.20 (m, 3H), 8.15-8.10 (m, 3H), 8.05-8.03 (m, 1H), 7.97-7.68 (m, 15H), 7.62-7.57 (m, 13H) | 905.32 | 904.32 |
| 80 | δ = 9.03-9.01 (m, 1H), 8.97 (s, 1H), 8.85-8.83 (m, 2H), 8.75-8.73 (m, 2H), 8.60 (m, 1H), 8.36-8.34 (m, 1H), 8.17-8.08 (m, 4H), 8.00-7.98 (ss, 1H), 7.90-7.88 (m, 3H), 7.79-7.46 (m, 15H), 7.37-7.33 (m, 1H) | 741.27 | 740.27 |

Example 1

To manufacture an anode, a substrate with deposited ITO/Ag/ITO layers (70/1000/70 Å) was cut to a size of 50 mm×50 mm×0.5 mm and then sonicated in isopropyl alcohol and pure water each for five minutes, and then cleaned by irradiation of ultraviolet rays for 30 minutes and exposure to ozone. The resulting glass substrate was loaded into a vacuum deposition device.

Then, 2-TNATA, which is a hole-injecting material, was vacuum-deposited on the glass substrate to form a HIL having a thickness of about 600 Å. Then, 4,4'-bis[N-(1-naphthyl)-N-phenylamino]biphenyl (NPB), which is a hole transporting compound, was vacuum-deposited on the HIL to form a HTL having a thickness of about 1000 Å.

Then, Compound 3 as a green phosphorescent host and Ir(ppy)$_3$ as a dopant were co-deposited in a weight ratio of 91:9 on the HTL to form an EML having a thickness of about 250 Å. Then, BCP as a hole blocking compound was vacuum-deposited on the EML to form a HBL having a thickness of about 50 Å. Then, Alq$_3$ was deposited on the HBL to form an ETL having a thickness of 350 Å, and then LiF, which is a halogenated alkali metal, was deposited on the ETL to form an EIL having a thickness of 10 Å. Then, Mg and Ag were vacuum-deposited in a weight ratio of 90:10 on the EIL to form a cathode having a thickness of 120 Å, thereby completing the manufacture of an organic light-emitting device.

The organic light-emitting device had a driving voltage of about 5.5V at a current density of 10 mA/cm$^2$, a luminosity of 4,912 cd/m$^2$, an emission efficiency of 49.1 cd/A, and a half life-span (hr @100 mA/cm$^2$) of about 71 hours.

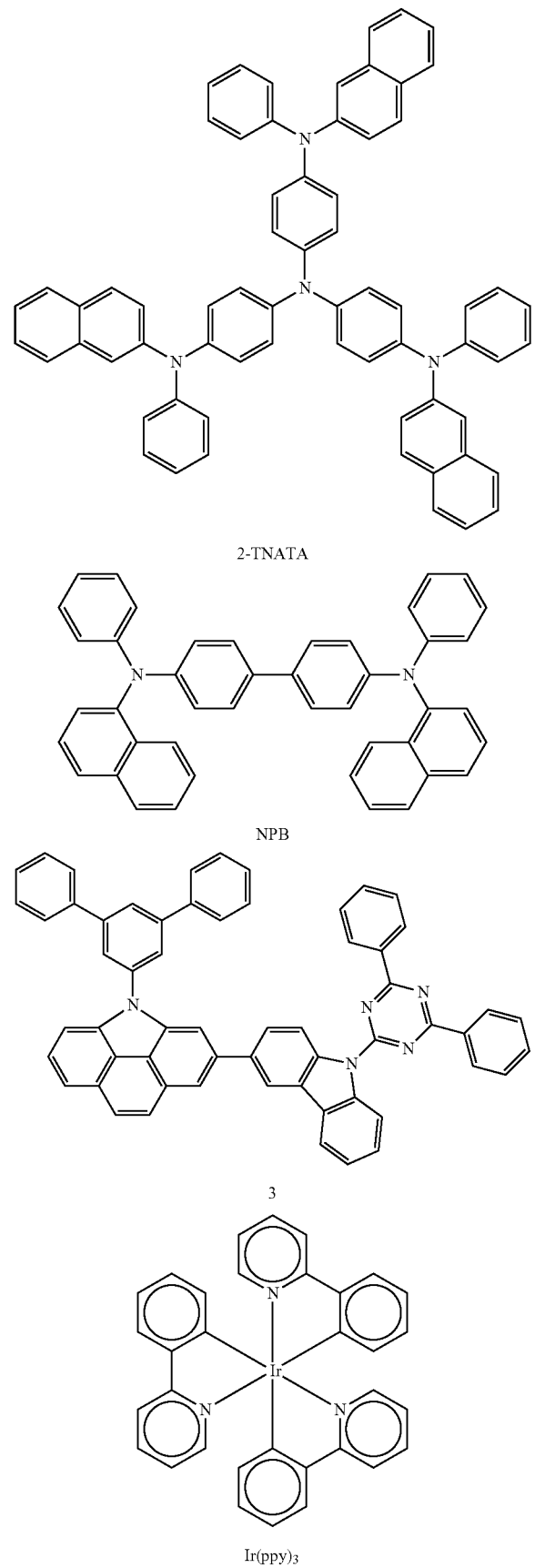

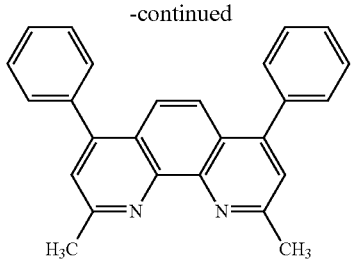

BCP

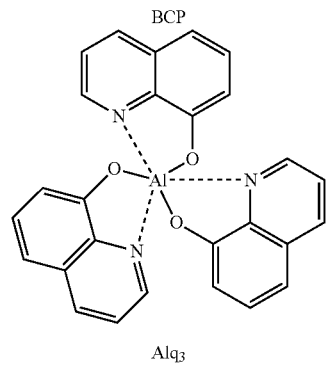

Alq₃

Example 2

An organic light-emitting device was manufactured in the same manner as in Example 1, except that Compound 21 instead of Compound 3 was used to form the EML.

The organic light-emitting device had a driving voltage of about 5.5V at a current density of 10 mA/cm², a luminosity of 5,123 cd/m², an emission efficiency of 51.2 cd/A, and a half life-span (hr @100 mA/cm²) of about 82 hours.

Example 3

An organic light-emitting device was manufactured in the same manner as in Example 1, except that Compound 45 instead of Compound 3 was used to form the EML.

The organic light-emitting device had a driving voltage of about 5.1V at a current density of 10 mA/cm², a luminosity of 5,394 cd/m², an emission efficiency of 53.9 cd/A, and a half life-span (hr @100 mA/cm²) of about 69 hours.

Example 4

An organic light-emitting device was manufactured in the same manner as in Example 1, except that Compound 63 instead of Compound 3 was used to form the EML.

The organic light-emitting device had a driving voltage of about 5.4V at a current density of 10 mA/cm², a luminosity of 5,454 cd/m², an emission efficiency of 54.5 cd/A, and a half life-span (hr @100 mA/cm²) of about 91 hours.

Example 5

An organic light-emitting device was manufactured in the same manner as in Example 1, except that 4,4'-bis[N-(1-naphthyl)-N-phenylamino]biphenyl (NPB) as a HTL material was vacuum-deposited to form a HTL having a thickness of about 1350 Å, and Compound 11 as a red phosphorescent host and bis(2-(2'-benzo[4,5-a]thienyl)pyridinato-N, C3') iridium acetylacetonate (Btplr) as a dopant were co-deposited on the HTL in a weight ratio of 94:6 to form an EML having a thickness of 400 Å.

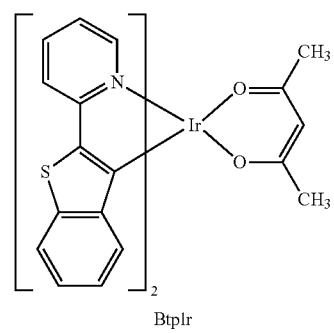

Btplr

The organic light-emitting device had a driving voltage of about 5.8V at a current density of 10 mA/cm², a luminosity of 2,542 cd/m², an emission efficiency of 25.4 cd/A, and a half life-span (hr @100 mA/cm²) of about 101 hours.

Example 6

An organic light-emitting device was manufactured in the same manner as in Example 5, except that Compound 52 instead of Compound 11 was used to form the EML.

The organic light-emitting device had a driving voltage of about 5.7V at a current density of 10 mA/cm², a luminosity of 2,633 cd/m², an emission efficiency of 23.3 cd/A, and a half life-span (hr @100 MA/cm³) of about 90 hours.

Example 7

An organic light-emitting device was manufactured in the same manner as in Example 5, except that Compound 75 instead of Compound II was used to form the EML.

The organic light-emitting device had a driving voltage of about 5.2V at a current density of 10 mA/cm², a luminosity of 2,954 cd/m², an emission efficiency of 29.5 cd/A, and a half life-span (hr @100 mA/cm²) of about 94 hours.

Example 8

An organic light-emitting device was manufactured in the same manner as in Example 1, except that Compound 49 instead of Alq₃ was used to form the ETL.

The organic light-emitting device had a driving voltage of about 4.9V at a current density of 10 mA/cm², a luminosity of 5,625 cd/m², an emission efficiency of 56.3 cd/A, and a half life-span (hr @100 mA/cm²) of about 98 hours.

Example 9

An organic light-emitting device was manufactured in the same manner as in Example 8, except that Compound 80 instead of Compound 49 was used to form the ETL.

The organic light-emitting device had a driving voltage of about 5.1V at a current density of 10 mA/cm², a luminosity of 5,812 cd/m², an emission efficiency of 58.1 cd/A, and a half life-span (hr @100 mA/cm²) of about 112 hours.

Comparative Example 1

An organic light-emitting device was manufactured in the same manner as in Example 1, except that a widely known green phosphorescent host 4,4'-N,N'-dicarbazolbiphenyl (CBP), instead of Compound 3, was used to form the EML.

The organic light-emitting device had a driving voltage of about 6.5V at a current density of 10 mA/cm$^2$, a luminosity of 3,210 cd/m$^2$, an emission efficiency of 32.1 cd/A, and a half life-span (hr @100 mA/cm$^2$) of about 32 hours.

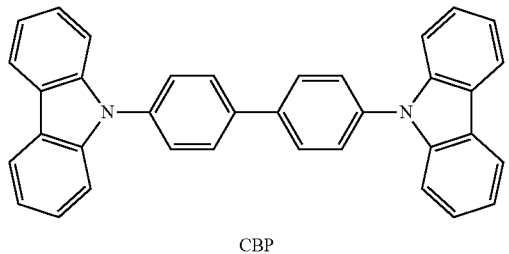 [SMILES: c1ccc2c(c1)c1ccccc1n2-c1ccc(-c2ccc(-n3c4ccccc4c4ccccc43)cc2)cc1 ; "CBP"]

CBP

Comparative Example 2

An organic light-emitting device was manufactured in the same manner as in Example 5, except that a widely known red phosphorescent host 4,4'-N,N'-dicarbazolbiphenyl (CBP), instead of Compound 11, was used to form the EML.

The organic light-emitting device had a driving voltage of about 6.8V at a current density of 10 mA/cm$^2$, a luminosity of 1,643 cd/m$^2$, an emission efficiency of 16.4 cd/A, and a half life-span (hr @100 mA/cm$^2$) of about 45 hours.

The organic light-emitting devices manufactured using the heterocyclic compounds represented by Formula 1 above according to embodiments as green or red phosphorescent hosts in the EML or as ETL materials had markedly lower driving voltages and improved I-V-L characteristics with a higher efficiency, compared to those manufactured using a widely-known materials such as CBP or Alq$_3$. In particular, the organic light-emitting devices according to the embodiments had markedly improved lifetimes. Main characteristics and lifetime characteristics of the organic light-emitting devices of Examples 1 to 9 and Comparative Examples 1 and 2 are shown in Table 2 below.

As described above, according to the one or more embodiments of the present invention, a heterocyclic compound of Formula 1 has improved charge transporting capability and improved light-emitting capability, and thus is suitable as a light emitting material or electron transporting material for fluorescent or phosphorescent devices of any color of red, green, blue, or white. Therefore, an organic light-emitting device having high efficiency, low driving voltages, high luminance, and long lifetime may be manufactured using the heterocyclic compound of Formula 1.

It should be understood that the exemplary embodiments described therein should be considered in a descriptive sense only and not for purposes of limitation. Descriptions of features or aspects within each embodiment should typically be considered as available for other similar features or aspects in other embodiments or equivalents thereof.

What is claimed is:
1. A heterocyclic compound represented by Formula 1:

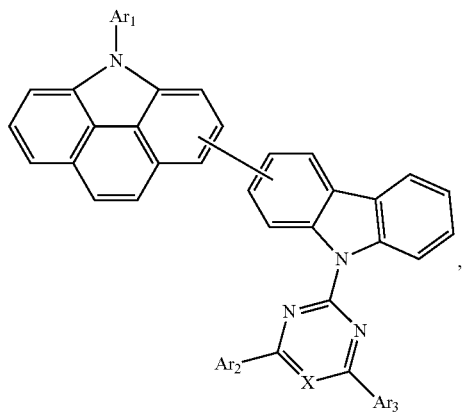

Formula 1 wherein, in Formula 1,
Ar$_1$ to Ar$_3$ are each independently selected from a hydrogen atom, a deuterium atom, a substituted or unsubstituted

TABLE 2

| | Host or ETL material | Driving voltage (V) | Current density (mA/cm$^2$) | Luminosity (cd/m$^2$) | Efficiency (cd/A) | Emission color | Lifetime LT97 (hr) |
|---|---|---|---|---|---|---|---|
| Example 1 | Compound 3 | 5.5 | 10 | 4,912 | 49.1 | Green | 71 hr |
| Example 2 | Compound 21 | 5.5 | 10 | 5,123 | 51.2 | Green | 82 hr |
| Example 3 | Compound 45 | 5.1 | 10 | 5,394 | 53.9 | Green | 69 hr |
| Example 4 | Compound 63 | 5.4 | 10 | 5,454 | 54.5 | Green | 91 hr |
| Example 5 | Compound 11 | 5.8 | 10 | 2,542 | 25.4 | Red | 101 hr |
| Example 6 | Compound 52 | 5.7 | 10 | 2,633 | 26.3 | Red | 90 hr |
| Example 7 | Compound 75 | 5.2 | 10 | 2,954 | 29.5 | Red | 94 hr |
| Example 8 | Compound 49 | 4.9 | 10 | 5,625 | 56.3 | Green | 98 hr |
| Example 9 | Compound 80 | 5.1 | 10 | 5,812 | 58.1 | Green | 112 hr |
| Comparative Example 1 | CBP | 6.5 | 10 | 3,210 | 32.1 | Green | 32 hr |
| Comparative Example 2 | CBP | 6.8 | 10 | 1,643 | 16.4 | Red | 45 hr |

C1-C60 alkyl group, a substituted or unsubstituted C3-C60 cycloalkyl group, a substituted or unsubstituted C1-C60 heteroaryl group, a substituted or unsubstituted C6-C60 aryl group, and a substituted or unsubstituted C6-C60 condensed polycyclic group; and X is N or CH.

2. The heterocyclic compound of claim 1, wherein the heterocyclic compound is represented by Formula 2:

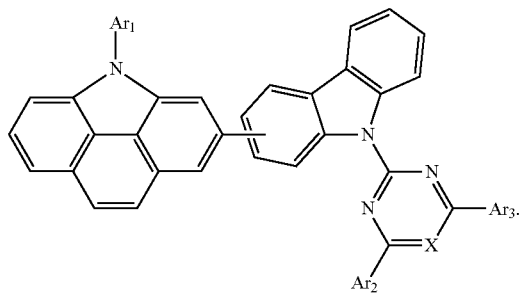

Formula 2

3. The heterocyclic compound of claim 1, wherein the heterocyclic compound is represented by Formula 3:

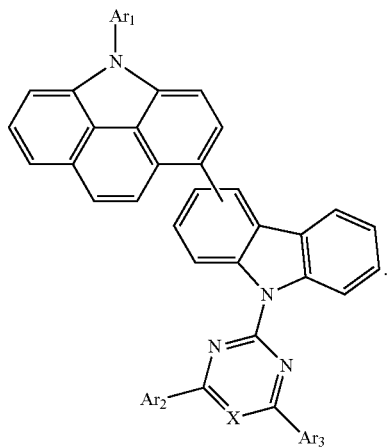

Formula 3

4. The heterocyclic compound of claim 1, wherein $Ar_1$ is selected from the group of compounds represented by Formulae 2a to 2c:

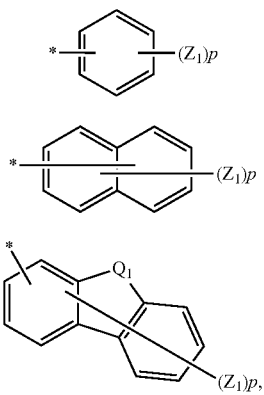

2a

2b

2c wherein, in Formulae 2a to 2c, $Q_1$ is O or S;

$Z_1$ is selected from the group consisting of a hydrogen atom, a deuterium atom, a substituted or unsubstituted C1-C20 alkyl group, C1-C20 alkylsilyl group, C1-C20 arylsilyl group, a substituted or unsubstituted C6-C20 aryl group, a substituted or unsubstituted C2-C20 heteroaryl group, a substituted or unsubstituted C6-C20 condensed polycyclic group, an amino group substituted with at least one of a C6-C20 aryl group or a C2-C20 heteroaryl group, a halogen group, a cyano group, a nitro group, a hydroxy group, and a carboxy group, wherein a plurality of $Z_1$s are the same or different;

p in Formula 2a is an integer from 1 to 5, p in Formulae 2b and 2c is an integer from 1 to 7; and

* indicates a binding site.

5. The heterocyclic compound of claim 1, wherein $Ar_2$ and $Ar_3$ are each independently selected from the group of compounds represented by Formulae 3a to 3c:

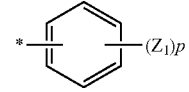

3a

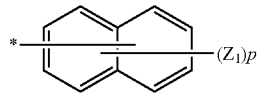

3b

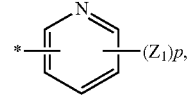

3c wherein, in Formulae 3a to 3c, $Z_1$ is selected from the group consisting of a hydrogen atom, a deuterium atom, a substituted or unsubstituted C1-C20 alkyl group, C1-C20 alkylsilyl group, C1-C20 arylsilyl group, a substituted or unsubstituted C6-C20 aryl group, a substituted or unsubstituted C2-C20 heteroaryl group, a substituted or unsubstituted C6-C20 condensed polycyclic group, an amino group substituted with at least one of a C6-C20 aryl group or a C2-C20 heteroaryl group, a halogen group, a cyano group, a nitro group, a hydroxy group, and a carboxy group, wherein a plurality of $Z_1$s are the same or different;

p in Formula 3a is an integer from 1 to 5, p in Formula 3b is an integer from 1 to 7, p in Formula 3c is an integer from 1 to 4; and

* indicates a binding site.

6. The heterocyclic compound of claim 1, wherein the heterocyclic compound is one of the compounds below:

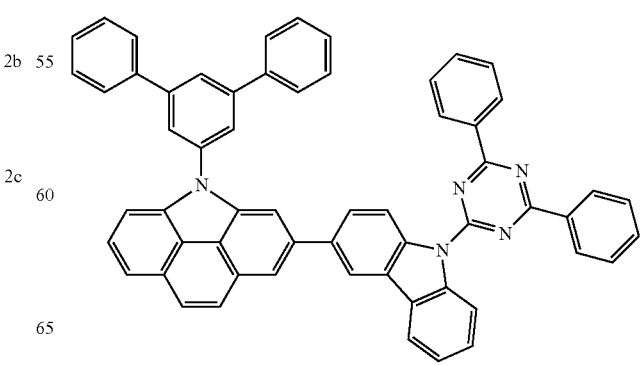

3

101
-continued
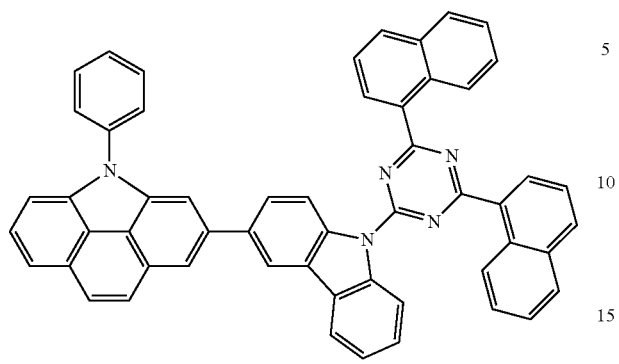
11
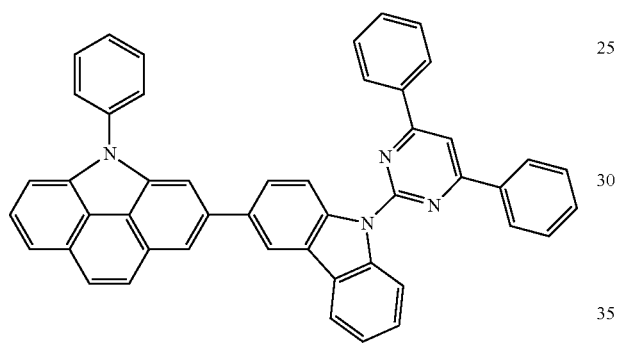
21
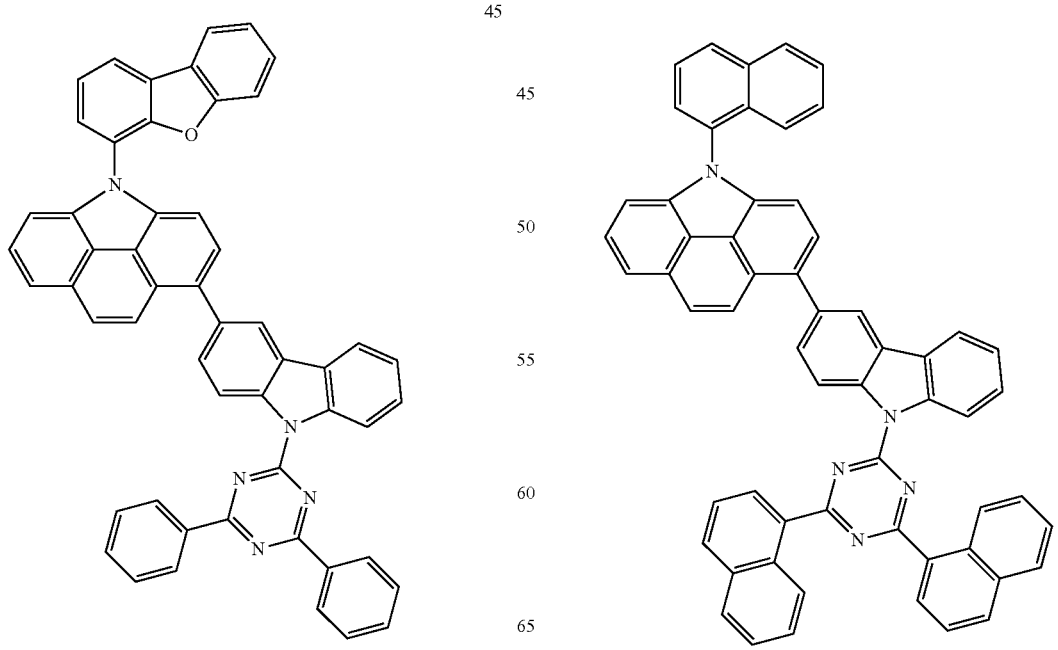
45
102
-continued
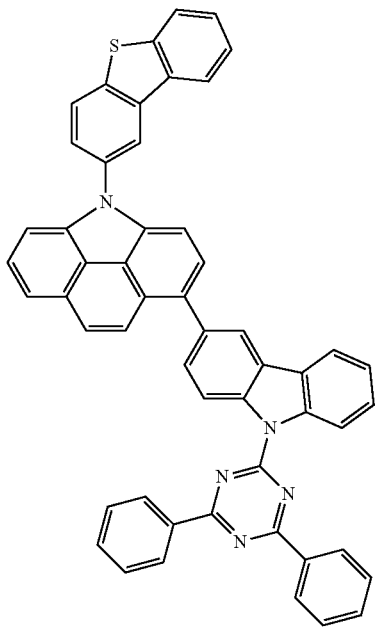
49
52

103
-continued

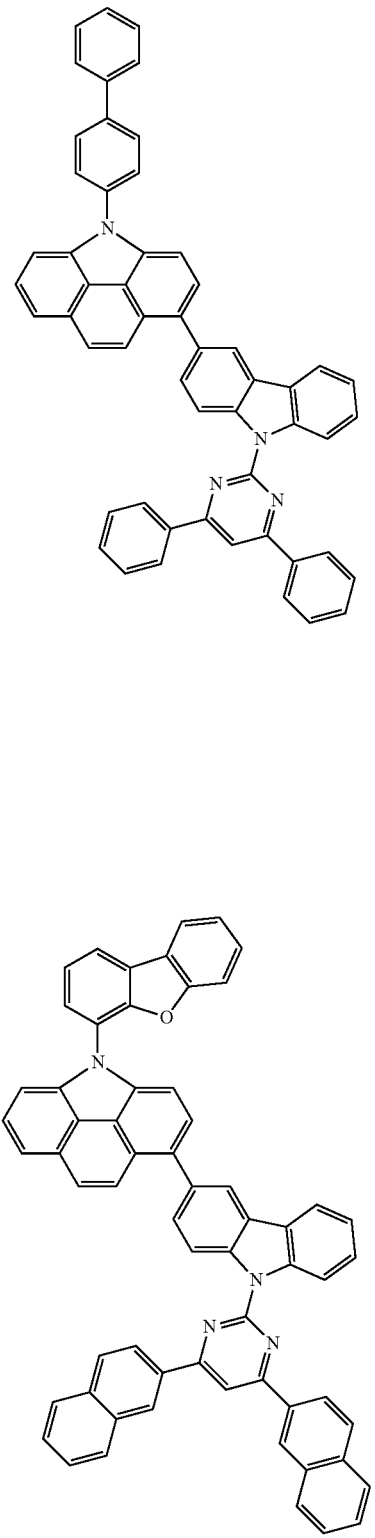

104
-continued

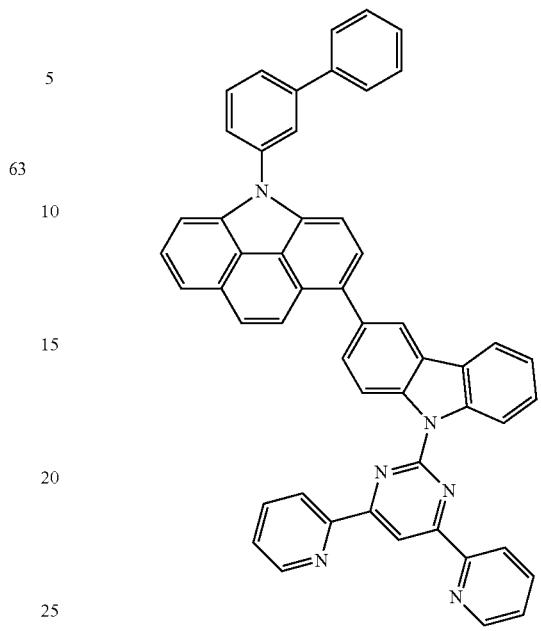

7. An organic light-emitting device comprising:
a first electrode;
a second electrode; and
an organic layer between the first electrode and the second electrode, the organic layer comprising the heterocyclic compound of claim 1.

8. The organic light-emitting device of claim 7, wherein the organic layer comprises an emission layer or an electron transport layer, wherein the emission layer or the electron transport layer comprises the heterocyclic compound.

9. The organic light-emitting device of claim 7, wherein the organic layer comprises an emission layer comprising an anthracene-based compound, an arylamine-based compound, or a styryl-based compound, and one or more of an electron injection layer, an electron transport layer, a functional layer having both electron injection and electron transport capabilities, a hole injection layer, a hole transport layer, and a functional layer having both hole injection and hole transport capabilities.

10. The organic light-emitting device of claim 7, wherein the organic layer comprises an emission layer comprising red, green, blue, and white emission layer, one of which comprises a phosphorescent compound, and one or more of an electron injection layer, an electron transport layer, a functional layer having both electron injection and electron transport capabilities, a hole injection layer, a hole transport layer, and a functional layer having both hole injection and hole transport capabilities.

11. The organic light-emitting device of claim 10, wherein at least one of the hole injection layer, the hole transport layer, and the functional layer having both hole injection and hole transport capabilities comprises a charge-generating material.

12. The organic light-emitting device of claim 11, wherein the charge-generating material is a p-type dopant.

13. The organic light-emitting device of claim 12, wherein the p-type dopant is a quinone derivative.

14. The organic light-emitting device of claim 12, wherein the p-type dopant is a metal oxide.

15. The organic light-emitting device of claim 12, wherein the p-type dopant is a cyano group-containing compound.

16. The organic light-emitting device of claim 7, wherein the organic layer comprises an electron transport layer comprising a metal complex.

17. The organic light-emitting device of claim 16, wherein the metal complex is a lithium (Li) complex.

18. The organic light-emitting device of claim 16, wherein the metal complex is lithium quinolate (LiQ) or Compound 203:

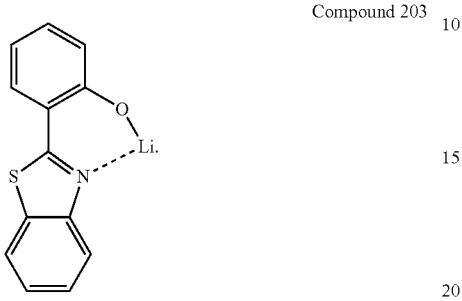

Compound 203

19. The organic light-emitting device of claim 7, wherein the organic layer is formed from the heterocyclic compound using a wet process.

20. A flat panel display device comprising the organic light-emitting device of claim 7, wherein the first electrode of the organic light-emitting device is electrically connected to a source electrode or a drain electrode of a thin-film transistor.

* * * * *